US010287602B2

(12) United States Patent
Marillonnet et al.

(10) Patent No.: US 10,287,602 B2
(45) Date of Patent: May 14, 2019

(54) RNA VIRUS-DERIVED PLANT EXPRESSION SYSTEM

(71) Applicant: Icon Genetics GmbH, München (DE)

(72) Inventors: Sylvestre Marillonnet, Halle (DE); Carola Engler, Halle (DE); Victor Klimyuk, Leipzig (DE); Yuri Gleba, Berlin (DE)

(73) Assignee: Icon Genetics GmbH, Halle (Saale) (DE)

( * ) Notice: Subject to any disclaimer, the term of this patent is extended or adjusted under 35 U.S.C. 154(b) by 257 days.

(21) Appl. No.: 14/988,092

(22) Filed: Jan. 5, 2016

(65) Prior Publication Data

US 2016/0208276 A1    Jul. 21, 2016

Related U.S. Application Data

(63) Continuation of application No. 10/578,962, filed as application No. PCT/EP2004/012743 on Nov. 10, 2004, now Pat. No. 9,267,143, which is a continuation-in-part of application No. PCT/EP03/12530, filed on Nov. 10, 2003.

(30) Foreign Application Priority Data

Jul. 7, 2004   (EP) .................................. 04016012

(51) Int. Cl.
C12N 15/84       (2006.01)
C12N 15/82       (2006.01)
C12P 21/00       (2006.01)

(52) U.S. Cl.
CPC ..... *C12N 15/8257* (2013.01); *C12N 15/8203* (2013.01); *C12N 15/8205* (2013.01); *C12N 15/8216* (2013.01); *C12P 21/00* (2013.01)

(58) Field of Classification Search
CPC .................................................. C12N 15/8257
USPC ....................................................... 435/469
See application file for complete search history.

(56) References Cited

U.S. PATENT DOCUMENTS

| 5,919,705 | A | 7/1999 | De Haan |
| 6,093,554 | A | 7/2000 | Haute et al. |
| 6,300,545 | B1 * | 10/2001 | Baszczynski ............ C12N 9/00 435/252.2 |
| 6,632,980 | B1 | 10/2003 | Yadav et al. |
| 2007/0044170 | A1 | 2/2007 | Marillonnet et al. |

FOREIGN PATENT DOCUMENTS

| WO | WO 94/16089 | 7/1994 |
| WO | WO 99/22003 | 5/1999 |
| WO | WO 00/53780 | 9/2000 |
| WO | WO 02/088369 A1 | 11/2002 |
| WO | WO 02/097080 A2 | 12/2002 |

OTHER PUBLICATIONS

Chakrabarty, R., et al., "Agrobacterium-mediated Transformation of Cauliflower: Optimization of Protocol and Development of Bt-transgenic Cauliflower," J. Biosci., 2002, pp. 495-502, vol. 27(5), Indian Academy of Sciences.
Haseloff, J., et al., "Removal of a Cryptic Intron and Subcellular Localization of Green Fluorescent Protein are Required to Mark Transgenic *Arabidopsis* Plants Brightly," Proc. Natl. Acad. Sci. USA, 1997, pp. 2122-2127, vol. 94, The National Academy of Sciences of the USA.
Koziel, M., et al., "Optimizing Expression of Transgenes with an Emphasis on Post-transcriptional Events," Plant Molecular Biology, 1996, pp. 393-405, vol. 32, Kluwer Academic Publishers, Belgium.
Mallory, Allison C., et al., "The Amplicon-plus System for High-level Expression of Transgenes in Plants," Nature Biotechnology, 2002, pp. 622-625 vol. 20.
Rose, A., "Requirements for Intron-mediated Enhancement of Gene Expression in *Arabidopsis*," RNA, 2002, pp. 1444-1453, vol. 8, RNA Society.
Simpson, C.G., et al., "Expression of a Heterologous Gene Can be Improved by Mutation of Cryptic Splice Sites," Annual Meeting of the Society for Experimental Biology, St. Andrews Scotland, UK, 1995, p. 38, vol. 46.
Simpson, C.G. and J.W.S. Brown, "Efficient Splicing of an AU-rich Antisense Intron Sequence," Plant Molecular Biology, 1993, pp. 205-211, vol. 21, Kluwer Academic Publishers, Belgium.
Knapp, ET, et al., "Conundrum of the Lack of Defective RNAs (dRNAs) Associated with *Tobamovirus* Infections: dRNAs That Can Move Are Not Replicated by the Wild-Type Virus; dRNAs That Are Replicated by the Wild-Type Virus Do Not Move," Journal of Virology, 2001, pp. 5518-5525, vol. 75(12), American Society for Microbiology.
Lough, T., et al., "Trans-Complementation of Long-Distance Movement of White Clover Mosaic Virus Triple Gene Block (TGB) Mutants Phloem-Associated Movement of TGBpl," Virology, 2001, pp. 18-28, vol. 288, Academic Press.
Abstracts of Research Outcomes in Shizuoka Prefectural Agricultural Experiment Station, 1999, vol. 43, pp. 263-164.
Baulcombe, et al., "Jellyfish green flourescent protein as a reporter for virus infections," The Plant Journal, 1995, vol. 7(6), pp. 1045-1053.

(Continued)

*Primary Examiner* — Li Zheng
(74) *Attorney, Agent, or Firm* — David M. Saravitz; Williams Mullen

(57) ABSTRACT

A process of expressing a sequence of interest in a plant, plant part, or plant cell culture, comprising: (a) providing a plant, plant part, or plant cell culture containing in cell nuclei a heterologous DNA having a sequence encoding an RNA replicon operably linked or linkable to a transcription promoter, wherein said sequence encoding an RNA replicon contains (i) sequences for replicon function of said RNA replicon, said sequences being derived from a sequence of a plant RNA virus, (ii) a sequence of interest, whereby said sequences for replicon function exhibit at selected localities of said sequences of said plant RNA virus function-conservative differences from said sequence of said plant RNA virus, said differences causing an increased frequency of replicon formation compared to an RNA replicon not exhibiting said differences; and (b) causing expression of said sequence of interest.

4 Claims, 22 Drawing Sheets

Specification includes a Sequence Listing.

(56) References Cited

OTHER PUBLICATIONS

Sakharkar, et al., "ExInt: an Exon/Intron database," Nucleic Acids Research, 2000, vol. 28(1), pp. 191-192.
Turpen et al., "Transfection of whole plants from wounds inoculated with *Agrobacterium tumefaciens* containing cDNA of tobacco mosaic virus," Journal of Virological Methods, 1993, vol. 42, pp. 227-240.
Dorokhov et al., Complete Nucleotide Sequence and genome organization of a *Tobamovirus* infecting cruciferae plants. Jun. 13, 1994, FEBS Letters 350 (1994) 5-8.
Ko et al., U-Richness is a defining feature of plant introns and may function as an intron recognition signal in maize, Plant Molecular Biology 36: pp. 573-583, 1998.
Marillonnet et al., "In planta engineering of viral RNA replicons: Efficient assembly by recombination of DNA modules delivered by *Agrobacterium*," PNAS, 2004, vol. 101(18) pp. 6852-6857.
Chen et al. "AU-rich elements: characterization and importance in mRNA degradation." 1995. Trends Biochem. Sci. 20:465-470.
Genbank Accession No. Z29370.

\* cited by examiner

RNA VIRUS-DERIVED PLANT EXPRESSION SYSTEM

CROSS REFERENCE TO RELATED APPLICATIONS

This application is a continuation of the U.S. application Ser. No. 10/578,962, which issued on Feb. 23, 2016 as U.S. Pat. No. 9,267,143; which has a 35 U.S.C § 371 (c) date of Aug. 7, 2006; which is the U.S. National Stage of PCT/EP2004/012743, filed Nov. 10, 2004 and which designates the U.S.; which is a continuation-in-part of PCT/EP2003/012530, filed Nov. 10, 2003 and which designates the U.S.; and claims the benefit under 35 U.S.C. § 119(a) of European Application No. 04016012.9 filed Jul. 7, 2004; all of which are hereby incorporated herein in their entirety by reference.

FIELD OF THE INVENTION

The present invention relates to the plant, plant parts or plant cell cultures having a heterologous DNA encoding an RNA replicon for expressing a sequence of interest. The invention also provides a process of expressing a sequence of interest in plants, plant parts or plant cell cultures. The process and vectors provide the plant cells with an increased frequency of RNA virus-derived RNA replicon formation. Said heterologous DNA or part(s) thereof can be stably incorporated into the plant nuclear chromosomal or episomal DNA or transiently delivered. The invention also provides processes of *Agrobacterium*-mediated transformation of plants with (RNA) viral vectors or (RNA) viral replicons.

BACKGROUND OF THE INVENTION

Among plant transgene expression systems, expression of a transgene under the control of a heterologous promoter has been in use for several years. Apart from such conventional plant expression systems, virus-based expression systems can be used for rapid protein production in plants (for review see: Porta & Lomonossoff, 1996, *Mol. Biotechnol.*, 5, 209-221; Yusibov et al., 1999, *Curr. Top. Microbiol. Immunol.*, 240, 81-94) and are a powerful tool for functional genomics studies (Dalmay et al., 2000, *Plant Cell*, 12, 369-379; Ratcliff et al., 2001, *Plant J.*, 25, 237-245; Escobar et al., 2003, *Plant Cell*, 15, 1507-1523). Numerous publications and patents in the field describe systems based on DNA and RNA viral vectors (Kumagai et al., 1994, *Proc. Natl. Acad. Sci. USA*, 90, 427-430; Mallory et al., 2002, *Nature Biotechnol.* 20, 622-625; Mor et al., 2003, *Biotechnol. Bioeng.*, 81; 430-437; U.S. Pat. Nos. 5,316,931; 5,589,367; 5,866,785; 5,491,076; 5,977,438; 5,981,236; WO02088369; WO02097080; WO9854342). The existing viral vector systems are usually restricted to a narrow host range in terms of their best performance and even the expression level of such vectors in their most favourable host is far below the upper biological limits of the system. An important issue of virus-based systems is the method of delivery of the viral replicon to a plant cell. The most broadly applied method of delivery for large-scale production (simultaneous production in many plants, e.g. in a farm field or a greenhouse) is the use of infectious copies of RNA viral vectors (Kumagai et al., 1995, *Proc. Natl. Acad. Sci. USA*, 92, 1679-1683). Because of a relatively high tendency of recombinant viral RNA vectors to lose the heterologous inserts during the cycles of their replication, the method requires transcription of DNA templates in vitro, and as a result is inefficient and expensive. Another approach to solve the delivery problem could be the presence of a viral RNA replicon precursor in each cell of a transgenic plant, such that it can be released upon triggering the replication process by complementing a function of the viral vector (e.g. using helper virus—U.S. Pat. No. 5,965,794) or using other regulated switch systems (e.g. site-specific recombination—U.S. Pat. No. 6,632,980).

Despite many publications in the field including patented technologies, there are still no large scale virus-based production systems that work with sufficient efficiency and yield for commercial high-yield production, predominantly due to two main reasons:

Firstly, transient plant virus-based expression systems are generally restricted to specific hosts, which may not be suitable for large scale cultivation due to their susceptibility to environmental factors. Moreover, they are generally restricted to certain parts of a plant host, thus excluding most of the plant biomass from the production process and as a result minimizes the relative yield of the recombinant product per unit of plant biomass down to a level comparable to that achievable by a conventional transcription promoter in a transgenic plant;

Secondly, attempts to scale up the virus-based production system by generating transgenic plant hosts having the viral replicon precursor stably integrated in each cell have not provided a solution either, in particular because of underperformance of said replicons in such position, "leakiness" of the gene of interest to be expressed from said replicon and lack of an efficient switch system for said vectors. Certain progress was achieved with PVX-based vectors by using suppressors of PTGS silencing as trigger of RNA replicon formation (Mallory et al., 2002, *Nature Biotechnol.*, 20, 622-625), but the system is still impractical, as there is no solution provided for an efficient control of the switch (PTGS suppressor) triggering viral vector replication. However, this system provided for an expression level of the GUS gene reaching 3% of total soluble protein (TSP), which is the best known so far for this type of system, but still no better than a conventional transgene expression system under control of a strong promoter. Another inducible system based on a plant tripartite RNA virus (Mon et al., 2001, *Plant J.*, 27, 79-86), Brome Mosaic Virus (BMV), gave a very low yield of the protein of interest (3-4 µg/g fresh weight), which is comparable with the yields provided by standard transcriptional promoters.

The low expression levels achieved so far with plant expression systems are a major reason why these systems are hardly competitive with other expression systems like bacterial, fungal, or insect cell expression systems. Low expression levels give rise to very high downstream costs for protein isolation and purification in a huge background of plant material. Therefore, costs for downstream processing quickly decrease, as the yield of the protein or product of interest per unit plant biomass increases.

There is presently no large-scale plant transgene expression system the yield and efficiency of which would be sufficiently high to compete on the market with other large-scale expression systems like bacterial, fungal, or insect cell expression systems. Such a plant expression would have to fulfill the following criteria as good as possible:

(i) high yield, including expression of the protein of interest in as many plant tissues as possible and in as many cells of said tissues;

(ii) for preventing a deleterious effect of protein expression on plant growth, expression of the protein or product of interest should be switchable such that expression can be switched on at a desired point in time.

(iii) the switching should be such that expression can be switched on simultaneously or nearly simultaneously in all tissues or cells of a plant and, at the same time, in all plants of a selected group of plants, e.g. in all plants of a selected lot of plants. Typically, the protein or product of interest accumulates in each cell producing said product or protein up to a certain point. During accumulation, however, degradative processes frequently set on that tend to reduce the yield or quality of the protein or product of interest. Therefore, there is an optimal point in time after switching on expression, where the product or protein of interest should be harvested. This optimal point in time should be reached in all tissues or cells of a plant and in all plants of a selected lot at the same time to make the overall process efficient and profitable.

Therefore, it is an object of this invention to provide a transgenic plant, plant part, or plant cell culture for a high-yield plant expression system. It is another object to provide a process of transiently expressing a sequence of interest in a plant, plant part, or plant cell culture. It is another object of the invention to provide an efficient process of expressing one or more sequences of interest in a plant, plant part of plant cell culture, whereby said process can be used efficiently on a large scale. Further, it is an object of the invention to provide a method of controlling the expression of nucleic acid sequence(s) of interest in a plant, plant part, or plant cell culture, which is of improved ecological and biological safety.

GENERAL DESCRIPTION OF THE INVENTION

The above objects are achieved by a transformed plant, plant part, or plant cell culture containing in cell nuclei a heterologous DNA having a sequence encoding an RNA replicon, said sequence being operably linked or linkable to a transcription promoter, wherein said sequence encoding an RNA replicon contains
(i) sequences for replicon function of said RNA replicon, said sequences being derived from a sequence of a plant RNA virus, and
(ii) a sequence of interest to be expressed from said RNA replicon,
whereby said sequences for replicon function correspond to sequences of said plant RNA virus and exhibit at selected localities of said sequence of said plant RNA virus function-conservative differences from said sequence of said plant RNA virus. Said differences can cause an increased frequency of replicon formation compared to an RNA replicon not exhibiting said differences. Preferably, said plant, plant part, or cells of said plant cell culture are stably transformed with said heterologous DNA.

Further, the above objects are achieved by a process of expressing a sequence of interest in a plant, plant part, or plant cell culture, comprising:
(a) providing a plant, plant part, or plant cell culture containing in cell nuclei a heterologous DNA as defined above and
(b) causing expression of said sequence of interest.
Cells of said plant, said plant part, or said plant cell culture may be stably or transiently transformed with said heterologous DNA.

The invention also provides a process of producing a transgenic plant stably transformed on a nuclear chromosome with a heterologous DNA as defined above, comprising transforming a plant or a plant part with a vector containing said heterologous DNA, selecting tissue of said plant containing on a nuclear chromosome said heterologous DNA, and regenerating a transgenic plant from said tissue.

The invention further provides a process of transiently expressing a sequence of interest in a plant, plant part, or plant cell culture, comprising:
transforming a plant, plant part, or plant cell culture with a heterologous DNA having a sequence encoding an RNA replicon operably linked or linkable to a transcription promoter, wherein said sequence encoding an RNA replicon contains
(i) sequences for replicon function of said RNA replicon, said sequences being derived from a sequence of a plant RNA virus,
(ii) a sequence of interest,
whereby said sequences for replicon function exhibit at selected localities of said sequences of said plant RNA virus function-conservative differences from said sequence of said plant RNA virus. Said differences can cause an increased frequency of replicon formation compared to an RNA replicon not exhibiting said differences.

The invention further provides a nucleic acid molecule for producing said plant, plant part, or plant cell culture of the invention or for carrying out the process of the invention. Said nucleic acid molecule is as defined in the claims and as further defined as described below with reference to the plant, plant part of plant cell culture and said process of the invention.

When the inventors of the present invention introduced a heterologous DNA encoding RNA viral replicons in nuclear chromosomes of plants or plant parts for expressing a protein of interest encoded in said RNA replicon, they found that the frequency with which RNA replicons appeared in the cytosol was very low and occurred only in a small fraction of cells containing the heterologous DNA. Accordingly, the expression level of the protein of interest was also very low. Many possible reasons for this problem were considered including positional effects of the chromosome, unsuitable transcription regulatory elements, gene silencing, defective transport of the replicon from the nucleus to the cytosol, a deleterious effect of the sequence of interest on transcription, RNA processing or replicon function etc. It was then surprisingly found that certain A/T(U)-rich sequence portions in the replicon were responsible for the low frequency of replicon formation in the cytosol. When the deleterious effect of said A/T(U)-rich sequence portions was suppressed, the frequency of replicon formation in the cytosol strongly increased, resulting in a strongly increased yield of the protein of interest.

The efficiency of the present invention is such that a new dimension in plant expression systems is attained. The expression levels achievable with the present invention are such that expenditures for downstream processing (including separation and purification of the protein of interest) are low enough to make the process of the invention competitive with other large-scale expression systems. In prior art expression systems using stably transformed plants, the expression level is low even if virus-based vectors are used, since replicons are produced in a small fraction of the cells. Replicons that spread in the plant cannot remedy this problem, as spreading is slow, notably over long distances. Therefore, expression does not proceed uniformly in the plant and degradation of the protein of interest will already take place in some parts of the plant while in others protein expression has not even started. The invention allows to trigger expression uniformly throughout the plant. The small fraction of cells that do not produce a replicon can be quickly invaded by replicons from neighbouring cells. The invention provides the first high-yield plant expression system that can be used on large scale. The invention even allows to produce two or more replicons in the same cell, whereby the probability of having both replicons in the same cells is still very high. Further, the efficiency of the expression system of the invention is such that the otherwise limiting plant specificity of RNA viruses is reduced.

The improved efficiency as described above can be achieved in combination with stable transformation as well as with transient transformation of plants, plant parts, or plant cells.

The (optionally stably) transformed plant, plant part, or plant cell culture and said nucleic acid molecule have a heterologous DNA encoding an RNA replicon. Said sequence encoding an RNA replicon contains
(i) sequences for replicon function of said RNA replicon, said sequences being derived from a sequence of a plant RNA virus, and
(ii) a sequence of interest to be expressed from said RNA replicon.

Said sequence encoding an RNA replicon contains a sequence of interest to be expressed from said RNA replicon (ii). Said sequence of interest to be expressed may lead to formation of an RNA of interest, like an RNA for RNA interference for suppressing a function of said plant. Preferably, however, said sequence of interest codes for a protein of interest and contains regulatory sequences for translating said protein of interest e.g. from said RNA replicon or from subgenomic RNA of said RNA replicon. The sequence of interest may include a sequence coding for a targeting signal for targeting the protein of interest to a particular cell compartment or for secreting said sequence of interest. Amino acid sequences for separating said protein of interest from a targeting signal may also be encoded. Said sequence of interest is a sequence that is heterologous to any sequences of said plant RNA virus, i.e. the process of the invention does not comprise a case restricted to transformation of a wild-type plant RNA virus into plants or plant leaves. Thus, said protein of interest is not a protein encoded by said plant RNA virus from which said sequences for replicon function are derived.

Said sequences for replicon function (i) of said RNA replicon correspond to sequences of said plant RNA virus inter alia in that the former may be a DNA copy of the latter. Said sequences for replicon function provide the RNA replicon with the function to replicate in the cytosol. Said sequences for replicon function typically code for one or more proteins involved in replication like an RNA-dependent RNA polymerase (replicase). Said sequences for replicon function may further code for functions of an RNA replicon like one or more proteins involved in cell-to-cell or systemic spreading of an RNA virus in a plant like a movement protein or a coat protein. Said sequences for replicon function are preferably derived from a sequence of a plant RNA virus, since plant RNA viruses are an easily accessible source for replicon functions. "Being derived" means that said sequences for replicon function are essentially a DNA copy of the corresponding sequences of said RNA virus and said DNA copy makes up a part of said heterologous DNA contained or to be introduced in cell nuclei. "Being derived" further means that said sequences for replicon function are not an exact DNA copy of the corresponding RNA sequence of said RNA virus, but exhibit function-conservative differences as described below. Since said differences are function-conservative, said sequences for replicon function preferably code for proteins capable of carrying out replicon functions similarly as they do for said RNA virus. Such function-conservative differences may, however, result in quantitative differences in the functionality of the encoded viral proteins compared to a case where such function-conservative differences are absent. In one embodiment, said heterologous DNA and said sequences for replicon function do not code for a protein required for long-distance movement like a coat protein (notably a tobamoviral coat protein). In another embodiment, said heterologous DNA lacks a movement protein. Thus, said sequences for replicon function of said heterologous DNA do not have to code for all functions of the RNA virus from which said sequences for replicon function are derived.

Said sequences for replicon function exhibit at selected localities of said sequence of said plant RNA virus function-conservative differences relative to said sequence of said plant RNA virus, said differences causing an increased frequency of replicon formation compared to an RNA replicon not exhibiting said differences. Said differences are causal for said increased frequency of replicon formation in plant cells, once the overall process has been switched on (see below). The causal connection between the increased frequency of replicon formation and said differences can be tested experimentally by comparing the frequency of replicon formation between sequences for replicon function having said differences and sequences for replicon function not having said differences. Such an experimental comparison can be made e.g. by counting protoplasts expressing said sequence of interest as described in the examples. Preferably, a sequence of interest coding for an easily detectable reporter protein like green fluorescent protein (GFP) is used for this purpose. As further described below, it is also preferred to perform the experimental comparison with RNA replicons not capable of cell-to-cell spreading.

Said function-conservative differences are introduced into said sequences for replicon function at selected localities of said sequence of said plant RNA virus. Said selected localities are localities in sequences for replicon function of said plant RNA virus that are responsible for a low probability of an RNA replicon transcribed in the nucleus to appear in the cytosol as a functional replicon. Preferably, such selected localities have a high A/T(U)-content, i.e. a high A-content and/or a high T-content (a high U-content on RNA level), or have cryptic splicing sites, i.e. sequence portions that can be recognized by the nuclear splicing machinery as splicing sites. Said selected localities may be identified in an RNA virus on which an RNA replicon is based by analyzing the RNA profile of the RNA virus as exemplified below. Further, selected localities may be identified experimentally by analyzing the RNA formed in a plant cell after transformation with a heterologous DNA encoding an RNA replicon that does not exhibit said (function-conservative) differences according to the invention. This experimental analysis may be done by RT-PCR, preferably together with sequencing of the RT-PCR products. In the RT-PCR test, the replicase is preferably rendered dysfunctional e.g. by a frame-shift mutation in order to prevent RNA replicons reaching the cytoplasm from amplifying; such amplification may lead to contamination of RNA transcripts with wild type virus or to an overrepresentation of amplified RNA replicons in the cytoplasm. In this way, undesired splicing products that indicate splicing events destroying the RNA replicon may be identified. Further, the exact sites of undesired splicing may be identified and then remedied by introducing said function-conservative differences at said selected localities.

Thus, the invention also provides a process of expressing a sequence of interest in a plant, plant part, or plant cell culture, wherein (A) a plant, plant part, or plant cell culture is provided with a heterologous DNA as defined herein but lacking said function-conservative differences, (B) testing RNA derived from said heterologous DNA for undesired splicing products in said sequences for replicon function (e.g. by RT-PCR), (C) identifying (e.g. in the sequence of a product of said RT-PCR), a selected locality as a locality of an undesired splicing event, (D) introducing a function-conservative difference (e.g. an intron) according to the invention into or near said selected locality identified in step (C) into the heterologous DNA of step (A) for producing said heterologous DNA of the invention, and expressing a sequence of interest in a plant, plant part, or plant cell culture according to the invention, e.g. from a plant stably or transiently transformed with said heterologous DNA of the invention.

Said function-conservative differences cause an increased frequency of RNA replicon formation by suppressing the deleterious effect of said selected localities on said frequency of RNA replicon formation. Said function-conservative differences may comprise a reduction of a high A/U-content in said RNA replicon by reducing a high NT content in said sequences for replicon function of said sequence encoding said RNA replicon. Said high A/U content may be reduced by at least partial deletion or at least partial replacement by G/C bases (e.g. using the degeneracy of the genetic code), provided said differences are function-conservative. Further, cryptic splicing sites flanking A/U-rich regions of said sequences derived from a plant RNA virus may be removed. Such function-conserved differences may be introduced at one or at, preferably, several selected localities.

Preferred function-conservative differences comprise the insertion of one or more introns, most preferably nuclear introns, or one or more sequences capable of forming nuclear introns near or within A/U-rich localities of said sequences being derived from sequences of said plant RNA virus. It has surprisingly been found that the introduction of introns at or near A/U-rich localities results in an increased frequency of RNA replicon formation. Several introns may be introduced and examples are given herein for various numbers of introduced introns. The effects of more than one intron are cumulative. Further, intron insertion may be combined with other function-conservative differences at other selected localities.

FIG. 8 shows an example for the introduction of sequences capable of forming a nuclear intron, albeit in the gene of interest to be expressed. In the example of FIG. 8, the intron is formed from two intron halfs upon recombinase-catalyzed flipping of a part of said heterologous DNA. This principle may also be applied to sequences for replicon function of said RNA replicon. In an embodiment wherein two different RNA replicons are formed in the same cell, recombination between said two different replicons may result in the formation of an intron from two intron halfs present on different replicons. Further, an RNA replicon may be formed by recombination between two precursors, neither of which is a replicon. Also in this case, an intron may be assembled from two intron halfs derived from different precursor molecules.

Said plant, said plant part, or said plant cell culture of the invention may be stably transformed with said heterologous DNA. Stably transformed means that they contain said heterologous DNA in cell nuclei such that said heterologous DNA is maintained in said cell nuclei as nuclear chromosomes are maintained. Said heterologous DNA may be contained in or may be an episomal element. Preferably, however, said heterologous DNA is stably incorporated in a nuclear chromosome such that it can be inherited to progeny cells or progeny plants. Methods of producing plants, plant parts, or plant cell cultures that are stably transformed are known in the art of plant biotechnology. Such methods usually require the selection of transformants for stable transformation using a selective agent and a selectable marker gene.

Preferably, all cells of said plant, said plant part or said cell culture contain in their nuclei said heterologous DNA for giving a high yield of a protein of interest. More preferably, said cells contain said heterologous DNA stably integrated in a nuclear chromosome. In the case of a plant, this means that the plant is a transgenic plant.

Said heterologous DNA having said sequence encoding said RNA replicon is operably linked or linkable to a transcription promoter. Alternatively, said sequence encoding said RNA replicon is operably linked or linkable to a transcription promoter. If said heterologous DNA or said sequence is operably linked to said transcription promoter, the transcription promoter is preferably a regulated promoter, like an inducible, tissue-specific or developmentally regulated promoter in order to make expression of said sequence of interest regulatable. More preferably, said promoter is inducible or developmentally regulated, which allows that expression is induced at a desired time or that expression is switched on when the plant reaches a defined developmental stage, respectively. For example, expression of said sequence of interest can be switched on in plant seeds if said promoter is a seed-specific promoter. The invention is of high value for providing specific tissues (e.g. seed tissues) with RNA replicons, whereby said tissues may be less suited for cell-to-cell spread of said replicon than e.g. leaf tissue. Most preferred are chemically regulated promoters, since they allow to switch on expression at will in all or in most tissues of a plant. Most importantly, chemically inducible promoters are the promoters of choice for large scale applications, since the chemical inducer can be applied to a large number of plants at the same time. Examples of regulated promoters are known in the art. Large-scale applications are applications where a chosen sequence of interest is expressed in many plants concomittantly. Such a large-scale application may be performed in a greenhouse.

Said sequence encoding an RNA replicon may alternatively be operably linkable to a transcription promoter, which allows to switch on expression of said sequence of interest by operably linking said sequence encoding an RNA replicon with a promoter. There are several ways of reducing this embodiment to practice. One option is to separate, in said heterologous DNA, said sequence encoding an RNA replicon and said promoter by a sequence block that precludes an operable linkage between said promoter and said heterologous DNA. Said sequence block may be flanked by recombination sites such that said block can be cut out by a recombinase recognizing said recombination sites. Thereby, operable linkage for transcription of said sequence encoding an RNA replicon can be established and expression may be switched on. Another option is to have a portion of a sequence necessary for transcription (e.g. a promoter or promoter portion) in flipped orientation and flanked by recombination sites. Providing a suitable recombinase may flip said sequence portion back in correct orientation, whereby an operable linkage can be established.

In one embodiment of the invention, said sequence encoding an RNA replicon has one or more segments that code together for said RNA replicon, i.e. said RNA replicon is not encoded by one continuous DNA. Instead, said RNA replicon is encoded discontinuously by two or more segments, whereby said segments may be present on the same chromosome preferably contiguous to each other. Formation of said RNA replicon may then require rearrangement of said segments, e.g. by recombination. As an example, a part of a sequence for replicon function (e.g. a part of a sequence coding for a replicase) may be present in said heterologous DNA in a flipped orientation relative to other parts of such a sequence. The flipped part may be flanked by recombination sites. Then the transcript of the heterologous DNA will not be a replicon, since said replicon function cannot be provided (e.g. because the transcript does not code for a functional replicase). Providing a site-specific recombinase recognizing the recombination sites can flip one of said segments back such that a replicon function is encoded continuously. In this embodiment, providing the recombinase may function as a switch for switching on replicon formation and expression of a sequence of interest (see further below). This embodiment is preferably performed in connection with stably transformed plants, plant parts, or plant cell cultures.

Alternatively, said segments may be present on different chromosomes. Formation of an RNA replicon will then require transcription of both segments and trans-splicing of both transcripts for assembling said RNA replicon. This embodiment may be used for quickly segregating the segments that encode together said RNA replicon in progeny plants or cells as described in detail in PCT/EP03/02986.

The process of the invention may comprise said steps (a) and (b). Step (a) may comprise stable or transient transformation of a plant, plant part or plant cell culture with said heterologous DNA of the invention. As discussed above, stable transformation of a nuclear chromosome is preferred. Preferably, the process of the invention is a process of expressing a protein of interest encoded by said sequence of interest. Step (b) comprises causing expression of said sequence of interest, e.g. switching on said expressing. Various methods of causing or switching on expression have already been mentioned. Examples include inducing an inducible promoter operably linked to said heterologous DNA; bringing said heterologous DNA under operable linkage to a promoter using recombination; establishing continuous coding of a sequence for replicon formation using recombination etc. If a recombinase is used for switching on the process of the invention, said recombinase may be provided to said plant, plant part or plant cell culture transiently, whereby said providing would act as a switch for step (b). Alternatively, said recombinase may be stably encoded in cells, and expressing of the recombinase under control of a regulated, preferably inducible, promoter. Inducing recombinase expression by inducing said promoter may then cause expression in step (b). In the case of transient transformation, step (b) may be automatically achieved by performing step (a).

Preferably, the process of the invention is performed with many plants in parallel by providing many plants according to (a) and causing expression of said sequence of interest according to (b) with all plants in one step, e.g. by applying a chemical inducer for a chemically inducible promoter to all plants for example by spraying.

In an important embodiment of the process of the invention, said plant or said plant part (e.g. leaves) are transiently transformed with said heterologous DNA of the invention for transient expression of said sequence of interest. The term "transient transformation" means the introduction of said heterologous DNA without selection of transformed cells for stable incorporation of said heterologous DNA into a plant chromosome. Transient transformation usually provides for transient expression of the gene(s) encoded by heterologous DNA. Transient transformation can be achieved by any of the transformation methods given below. However, it is preferably performed by *Agrobacterium*-mediated transient transformation of T-DNA containing said heterologous DNA of the invention. A preferred method of *Agrobacterium*-mediated transient transformation is agroinfiltration. Agroinfiltration (agro-inoculation) is most preferred. The highest fastest and highest expression levels of said sequence of interest can be obtained if entire plants (i.e. the parts above the soil including all leaves) are transformed by agroinfiltration. This can be achieved by dipping the plant upside down in the *Agrobacterium* suspension, application of vacuum, and fast release of the vacuum.

In a preferred embodiment of said process of transiently expressing a sequence of interest, said sequence encoding an RNA replicon is operably linked to a transcriptional promoter, preferably a constitutive transcriptional promoter. In another preferred embodiment, said plant belongs to the genus *Nicotiana* and said sequences for replicon function are derived from a *tobamovirus*, preferably from tobacco mosaic virus. In a particularly preferred embodiment, tobacco plants including the stem and all leaves are transiently transformed by agroinfiltration. The latter embodiment can be used for large-scale applications of the process of the invention. In large-scale applications, said process is concomitantly applied to many plants (at least 5, preferably at least 10, more preferably at least 100 plants).

The present invention may in principal be applied to any plants for which infectious RNA viruses exist. Suitable plant/RNA virus pairs may be derived from the list of RNA viruses given below. Due to the very high efficiency of replicon formation according to the invention, the plant species specificity of plant viruses is far less pronounced when this invention is practiced. Similarly, the present invention may be used with RNA replicons based on any RNA virus. RNA viruses have generally evolved outside the cell nuclei of their host plants and will have selected localities that make a replicon based on such a virus inefficient when the replicon is produced inside cell nuclei, notably if the replicon is stably encoded in a nuclear chromosome. The invention can be applied to all RNA viruses, although the level of improvement may vary between different plant RNA viruses. The most preferred plant RNA viruses the invention may be based on are tobamoviruses, notably tobacco mosaic virus, and Potexviruses such as potato virus X. In the case of tobacco mosaic virus, it will generally be the coat protein that is replaced by said sequence to be expressed. The movement protein may be removed or replaced by a sequence to be expressed. Preferably, however, an RNA replicon derived from tobacco mosaic virus should code for the movement protein and have the coat protein be replaced by said sequence to be expressed. It is highly preferred that said heterologous DNA lacks at least one open reading frame of said plant RNA virus, like a coat protein or a movement protein.

The major application of the present invention is the production of a protein of interest in plants, plant parts or plant cell cultures. Said protein of interest is encoded by said sequence of interest. Said sequence of interest is preferably heterologous to said plant RNA virus. In any event, said sequence of interest is not a sequence having or encoding functions of said RNA virus.

If the process of the invention is performed in plants, plants that do not enter the human or animal food chain are preferred, like *Nicotiana* species (e.g. *Nicotiana benthamiana*, *Nicotiana tabacum*). Plant parts are e.g. plant organs or specific tissues of plants like leaves or seeds. Herein, seeds are considered as plant parts if the process of invention is done in seeds growing or being attached to a parent plant. Seeds are, however, also considered to be plants, albeit in a certain developmental stage of a plant. Most preferably, the plants of the invention are sold or distributed as seeds, the seeds are grown to plants, and expression of said sequence of interest is induced or switched on at a desired point in said plants.

Many plant species like *Nicotiana tabacum* or *Beta vulgaris* have hitherto been impossible to transform with a viral vector or a replicon by way of *Agrobacterium*-mediated transformation. It may be surmised that the reason for this impossibility was the activation of plant defense mechanisms in response to a double challenge of the plant with two pathogens, namely *Agrobacterium* and the viral vector. It has now been found by the inventors that the use of highly diluted suspension of Agrobacteria for *Agrobacterium*-mediated transformation allows to achieve a higher transformation efficiency with viral vectors. Thus, the invention achieves a broad applicability of *Agrobacterium*-mediated viral vector transformation to many plant species. The highly diluted suspension of Agrobacteria for this embodiment has a concentration of cells of said Agrobacteria corresponding to a calculated optical density at 600 nm of at most 0.04, preferably at most 0.01, more preferably at most 0.004, and most preferably at most 0.001, whereby said calculated optical densities are defined by an least 25-fold, preferably at least 100-fold, more preferably at least 250-fold, and most preferably at least 1000-fold dilution, respectively, of a suspension of said Agrobacteria of an OD at 600 nm of 1.0. The plant species most preferably transformed according to this embodiment is *Nicotiana tabacum*.

The transformation efficiency of *Agrobacterium*-mediated (RNA) viral vector transformation can further be improved by using in T-DNA the heterologous DNA according to the invention. Thus, the invention provides a process of expressing a sequence of interest in a plant, plant part, or plant cell culture, comprising:

transforming a plant, plant part, or plant cell culture with a suspension of Agrobacteria, said Agrobacteria containing in T-DNA a heterologous DNA having a sequence encoding a replicon (preferably an RNA replicon) operably linked or linkable to a transcription promoter, wherein said sequence encoding a replicon contains (i) sequences for replicon function of said replicon, said sequences being derived from a sequence of a plant virus (preferably a plant RNA virus),
(ii) a sequence of interest to be expressed, whereby said suspension of Agrobacteria has a concentration of cells of said Agrobacteria corresponding to a calculated optical density at 600 nm of at most 0.04, preferably at most 0.01, more preferably at most 0.004, and most preferably at most 0.001, whereby said calculated optical densities are defined by an least 25-fold, preferably at least 100-fold, more preferably at least 250-fold, and most preferably at least 1000-fold dilution, respectively, of a suspension of said Agrobacteria of an OD at 600 nm of 1.0.

The inventors have found that this process not only decreases the likelihood that cells of said *Agrobacterium* strain spread in the environment, thus improving the biological safety of this process. This process also improves the protein expression efficiency presumably by decreasing the exposure and stress for said plant or said plant leaves upon infection with an *Agrobacterium* strain that is a pathogen for said plant. The inventors have surprisingly found that the efficiency of the process increases, within certain limits, with decreasing concentration of the Agrobacteria suspensions used for transforming or transfecting plants or plant parts. Notably, the ability for cell-to-cell movement of the replicons generated in cells of said plant improves with decreasing concentration of these Agrobacteria suspensions. The reasons for this unexpected phenomenon has not yet been identified. It is speculated that this phenomenon is due to a response of the plant to the infection by Agrobacteria and that this response does not occur (or occurs to a lesser extent) at lower Agrobacteria concentrations. In prior art transformation processes using Agrobacteria, much higher concentrations of Agrobacteria are used, generally in the range of an OD at 600 nm of 0.5 to 1.0.

Said plant or said plant leaves are preferably infiltrated with a suspension of cells of said *Agrobacterium* strain, said suspension having a concentration of *Agrobacterium* cells obtainable by diluting a suspension of sells of said *Agrobacterium* strain of an OD (optical density) of 1.0 at 600 nm at least 25-fold, preferably at least 100-fold, more preferably at least 250-fold, and most preferably at least 1000-fold. Such dilutions thus lead to Agrobacteria suspensions having calculated OD values at 600 nm of at most 0.04, preferably at most 0.01, more preferably at most 0.004, and most preferably at most 0.001, respectively.

This process of using Agrobacteria suspensions with calculated OD values below 0.04 can be combined with other embodiments described in this invention. Infiltration or agro-infiltration may be defined as a transformation or transfection method using a suspension of Agrobacteria, wherein a pressure difference is used for pressing Agrobacteria into plant tissue (intercellular space).

BRIEF DESCRIPTION OF THE FIGURES

FIG. 7A—*Nicotiana benthamiana*, 8 days after agroinfiltration;

FIG. 7B—*Nicotiana tabacum*, 8 days after agroinfiltration;

FIG. 7C—*Nicotiana benthamiana* protoplasts isolated 5 days after agroinfiltration. Many light spots in the right picture indicate an extremely high frequency of replicon formation and GFP expression.

DETAILED DESCRIPTION OF THE INVENTION

Figure 1:
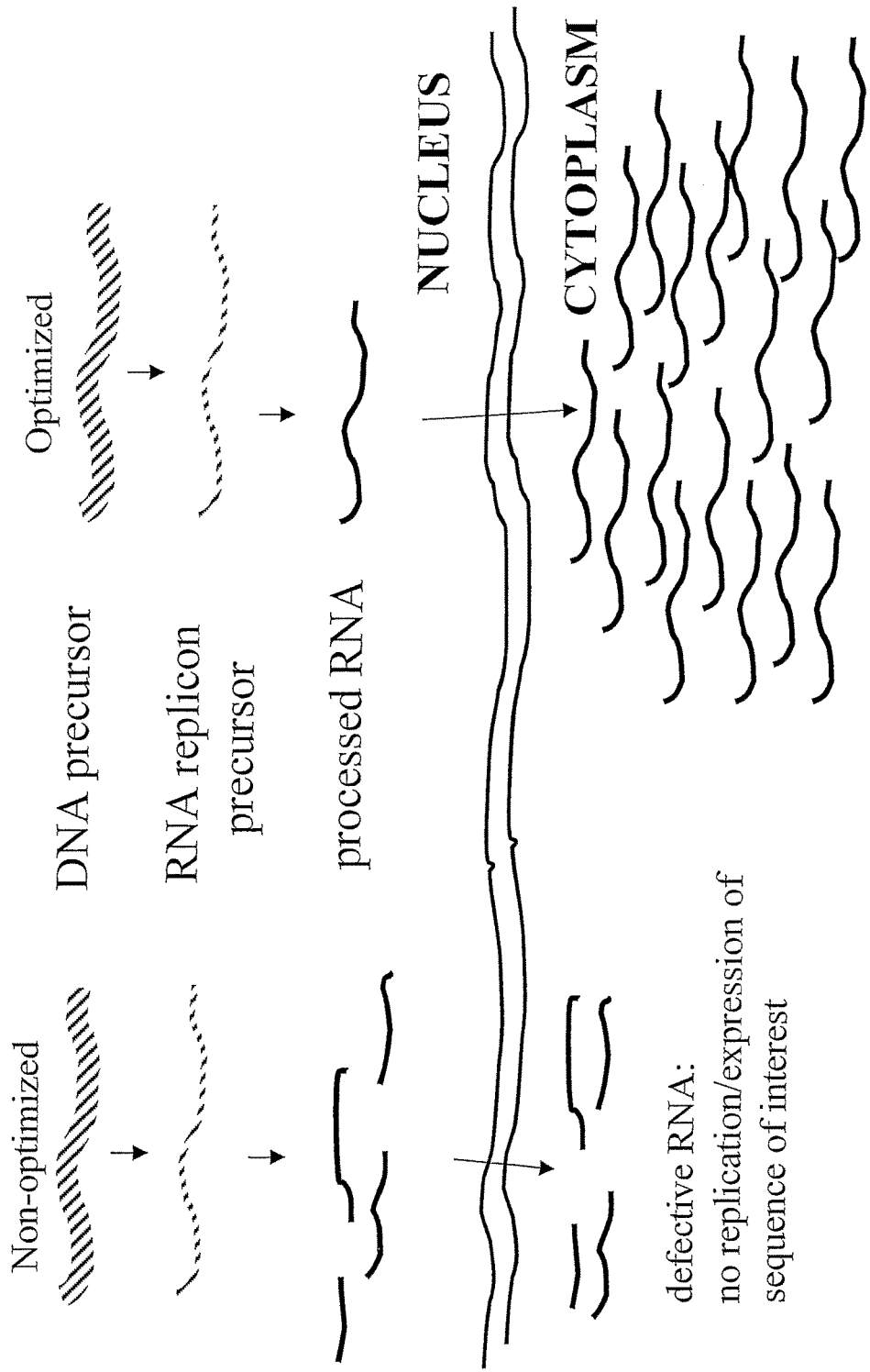
FIG. 1 depicts the general principle of the invention, based on increased frequency of RNA virus-based replicon formation.

We have surprisingly found that the incorporation of plant introns into certain regions of plant viral RNA vectors and removal or replacement of cryptic introns within sequences for replicon function can dramatically increase (at least ×10$^2$ folds) the efficiency of the appearance of said RNA replicons in the cytoplasm of host plants. Such increase in efficiency was reflected in at least one easily measurable parameter: relative proportion of cells showing replication of said vector, e.g. in increased frequency of replicon formation. Such optimisation of initiation of RNA replicon formation led to the ability of synchronized switching on of expression of a sequence of interest in a whole plant, resulting in dramatically increased yield of recombinant protein of interest in shorter time than for a non-modified vector.

Despite of publications concerning the increase of nuclear transgene expression by incorporation of introns in coding regions of recombinant DNA (Mascarenhas et al., 1990, *Plant Mol. Biol.*, 15, 913-920; Bourdon et al., 2001, *EMBO Reports*, 2, 394-398; Rose, A B., 2002, *RNA*, 8, 1444-1453; U.S. Pat. No. 5,955,330), there is no hint in the prior art showing that incorporation of introns into viral RNA replicons would have any positive effect on the frequency of viral replicon formation and subsequently, on the level of expression of a sequence of interest provided by said replicon. This effect is surprising considering that nuclear mRNA transcription and viral RNA replication take place in different sub-cellular compartments. Even if the cDNA copy of a viral replicon is placed in the nucleus, only the first copy of the viral replicon precursor is produced in nucleus and then amplified in the cytoplasm under conditions different from those in the nucleus. In the prior art, the use of introns for preventing the cytotoxic effect of "leaky" expression of viral genes in *E. coli* during cloning with wild type virus cDNAs was described (Johansen, I. E. 1996, *Proc. Natl. Acad. Sci. USA*, 93, 12400-12405; Yang et al., 1998, *Arch. Virol.*, 143, 2443-2451; Lopez-Moya & Garcia, 2000, *Virus Res.*, 68, 99-107). There is no hint that intron inclusion can increase the frequency of replicon formation from a viral cDNA clone. The results obtained for wild type RNA viruses and their cDNA copies cannot be compared with virus-derived expression vectors designed for the expression of a heterologous sequence of interest in plants, predominantly at the expense of other properties of wild type viruses like high infectivity and stability of said viruses. Infectivity is not an issue in the present invention. Notably, infectivity is not an issue in a process of expressing a sequence of interest in a stably transformed plant. Infectivity of a viral DNA vector or its transcript is also not an issue when a plant is transformed with Agrobacteria containing the DNA vector in T-DNA.

The present invention provides a method for increasing fundamentally the frequency of RNA virus-derived replicon formation, said replicons are derived upon transcription of DNA precursor and designed for the expression of sequences of interest. This method overcomes the limitations of existing viral vector-based expression systems, such as size limitation for heterologous sequences to be expressed and high instability of said vectors. Further, said method offers better biosafety characteristics, allows to design leakage-proof control over transgene expression (zero expression level in non-induced state), as such design can be an integrated part of the strategy for said RNA virus-derived replicon design. By providing high frequency of RNA virus-derived replicon formation, the approach described herein allows for a rapid initiation of the expression of a sequence of interest in a whole plant, part of plant or plant cell culture containing in cell nuclei a heterologous DNA encoding said RNA replicon. By practicing the invention, the performance of practically any plant RNA virus-derived replicon designed for the expression of a heterologous sequence of interest can be improved significantly through dramatic increase of the frequency of replicon formation.

RNA viruses belonging to different taxonomic groups are suitable for constructing RNA replicons according to this invention. A list of RNA viruses to which this invention can be applied, is presented below. Taxa names in quotes (and not in italic script) indicate that this taxon does not have an ICTV international approved name. Species (vernacular) names are given in regular script. Viruses with no formal assignment to genus or family are indicated):
RNA Viruses:
ssRNA Viruses: Family: Bromoviridae, Genus: *Alfamovirus*, Type species: alfalfa mosaic virus, Genus: *Ilarvirus*, Type species: tobacco streak virus, Genus: *Bromovirus*, Type species: brome mosaic virus, Genus: *Cucumovirus*, Type species: cucumber mosaic virus;

Family: Closteroviridae, Genus: *Closterovirus*, Type species: beet yellows virus, Genus: *Crinivirus*, Type species: Lettuce infectious yellows virus, Family: Comoviridae, Genus: *Comovirus*, Type species: cowpea mosaic virus, Genus: *Fabavirus*, Type species: broad bean wilt virus 1, Genus: *Nepovirus*, Type species: tobacco ringspot virus;

Family: Potyviridae, Genus: *Potyvirus*, Type species: potato virus Y, Genus: *Rymovirus*, Type species: ryegrass mosaic virus, Genus: *Bymovirus*, Type species: barley yellow mosaic virus;

Family: Sequiviridae, Genus: *Sequivirus*, Type species: parsnip yellow fleck virus, Genus: *Waikavirus*, Type species: rice tungro spherical virus; Family: Tombusviridae, Genus: *Carmovirus*, Type species: carnation mottle virus, Genus: *Dianthovirus*, Type species: carnation ringspot virus, Genus: *Machiomovirus*, Type species: maize chlorotic mottle virus, Genus: *Necrovirus*, Type species: tobacco necrosis virus, Genus: *Tombusvirus*, Type species: tomato bushy stunt virus, Unassigned Genera of ssRNA viruses, Genus: *Capillovirus*, Type species: apple stem grooving virus;

Genus: *Carlavirus*, Type species: carnation latent virus; Genus: *Enamovirus*, Type species: pea enation mosaic virus, Genus: *Furovirus*, Type species: soil-borne wheat mosaic virus, Genus: *Hordeivirus*, Type species: barley stripe mosaic virus, Genus: *Idaeovirus*, Type species: raspberry bushy dwarf virus;

Genus: *Luteovirus*, Type species: barley yellow dwarf virus; Genus: *Marafivirus*, Type species: maize rayado fino virus; Genus: *Potexvirus*, Type species: potato virus X; Genus: *Sobemovirus*, Type species: Southern bean mosaic virus, Genus: *Tenuivirus*, Type species: rice stripe virus, Genus: *Tobamovirus*, Type species: tobacco mosaic virus, Genus: *Tobravirus*, Type species: tobacco rattle virus, Genus: *Trichovirus*, Type species: apple chlorotic leaf spot virus; Genus: Tymovirus, Type species: turnip yellow mosaic virus; Genus: *Umbravirus*, Type species: carrot mottle virus; Negative ssRNA Viruses: Order: Mononegavirales, Family: Rhabdoviridae, Genus: *Cytorhabdovirus*, Type Species: lettuce necrotic yellows virus, Genus: *Nucleorhabdovirus*, Type species: potato yellow dwarf virus;

Negative ssRNA Viruses: Family: Bunyaviridae, Genus: *Tospovirus*, Type species: tomato spotted wilt virus;

dsRNA Viruses: Family: Partitiviridae, Genus: *Aiphacryptovirus*, Type species: white clover cryptic virus 1, Genus: *Betacryptovirus*, Type species: white clover cryptic virus 2, Family: Reoviridae, Genus: *Fijivirus*, Type species: Fiji disease virus, Genus: *Phytoreovirus*, Type species: wound tumor virus, Genus: *Oryzavirus*, Type species: rice ragged stunt virus;

Unassigned Viruses:

Genome: ssRNA, Species Garlic viruses A, B, C, D, Species grapevine fleck virus, Species maize white line mosaic virus, Species olive latent virus 2, Species: ourmia melon virus, Species *Pelargonium* zonate spot virus.

The general principle of the invention is shown in FIG. 1. It is known that plant RNA viruses (an exception are viroids—small non-coding RNAs amplifying in plant cell nuclei—for a review see Diener, T. O., 1999, *Arch. Virol. Suppl.*, 15, 203-220; Flores, R., 2001, *CR Acad. Sci. III*, 324, 943-952) never occur in the plant nucleus, but in the cytoplasm. Therefore, the sequences of RNA viruses might not be adapted to withstand nuclear RNA processing events due to the presence of motifs that might be involved in complex series of processing steps including transport of processed RNA in cytoplasm, in which pre-mRNAs, rRNA and tRNA precursors are involved. The processing events, such as 5' end capping, splicing, 3' end generation, polyadenylation, degradation, base and sugar modification as well as editing (in plastids and mitochondria) are intensively studied. However, many elements of such events still remain unclear. The most dramatic changes to pre-mRNA in the nucleus happen during pre-mRNA splicing, the process by which intervening RNA sequences (introns) are removed from the initial transcript and exons are concomitantly ligated. Splicing is mediated by the splicesome, a complex structure comprising uridilate-rich small nuclear ribonucleoprotein particles. The splicesome carries out the splicing reaction in two consecutive steps: the first one—cleavage at the 5' splice site of upstream exon/intron junction leading to lariat formation, and second step—cleavage at the 3' splice site of intron/downstream exon junction followed by upstream and downstream exons ligation (for review see: Kramer, A., 1996, *Annu. Rew. Biochem.*, 65, 367-409; Simpson, G G. & Filipowicz, W. 1996, *Plant. Mol. Biol.*, 32, 1-41). The 5' and 3' splice site dinucleotides (5'/GU; AG/3') flanking the intron sequences are highly conserved in higher plants and single G replacement might abandon the splicing activity at the site concerned. It is surprising that despite of a high conservation of splice sites between plants and animals, heterologous introns in plants are usually not spliced or spliced incorrectly (van Santen, V L. et al., 1987, *Gene*, 56, 253-265; Wiebauer, K., Herrero, J. J., Filipowicz, W. 1988, *Mol. Cel. Biol.*, 8, 2042-2051). Considering that plant viral RNAs were not under evolutionary pressure to resist nuclear RNA processing machinery, these RNAs are very likely to become subject of such processing, including splicing, once they are placed into the nuclear environment. This situation is completely different from that of RNA transcripts encoded by nuclear genes, as the latter transcripts are evolutionary adapted to preserve their functionality, despite of series of RNA modifications taking place in the nucleus. However, such modifications can have dramatic consequences for viral RNA replicon formation. Re-engineering of the plant virus in order to make expression vectors for heterologous genes might further add to the instability of RNA virus-based replicons, as it would add further elements that might interact with RNA sequences of viral origin, producing defective RNA that is unable to replicate. Our invention addresses these problems by subjecting the expression vector to modifications that significantly increase the frequency of functional RNA replicon formation, when the expression vector is introduced as a DNA precursor into plants or plant cells to provide for transient expression or for stable integration into plant chromosomal DNA. We believe that modifications of virus-derived sequences shall be the most profound solution for increasing the efficiency of RNA virus-based replicons. In this invention we predominantly focus on modifications (said function-conservative differences) within the plant RNA virus derived sequences, as they are crucial for increasing the efficiency of RNA replicon formation.

Figure 2A:
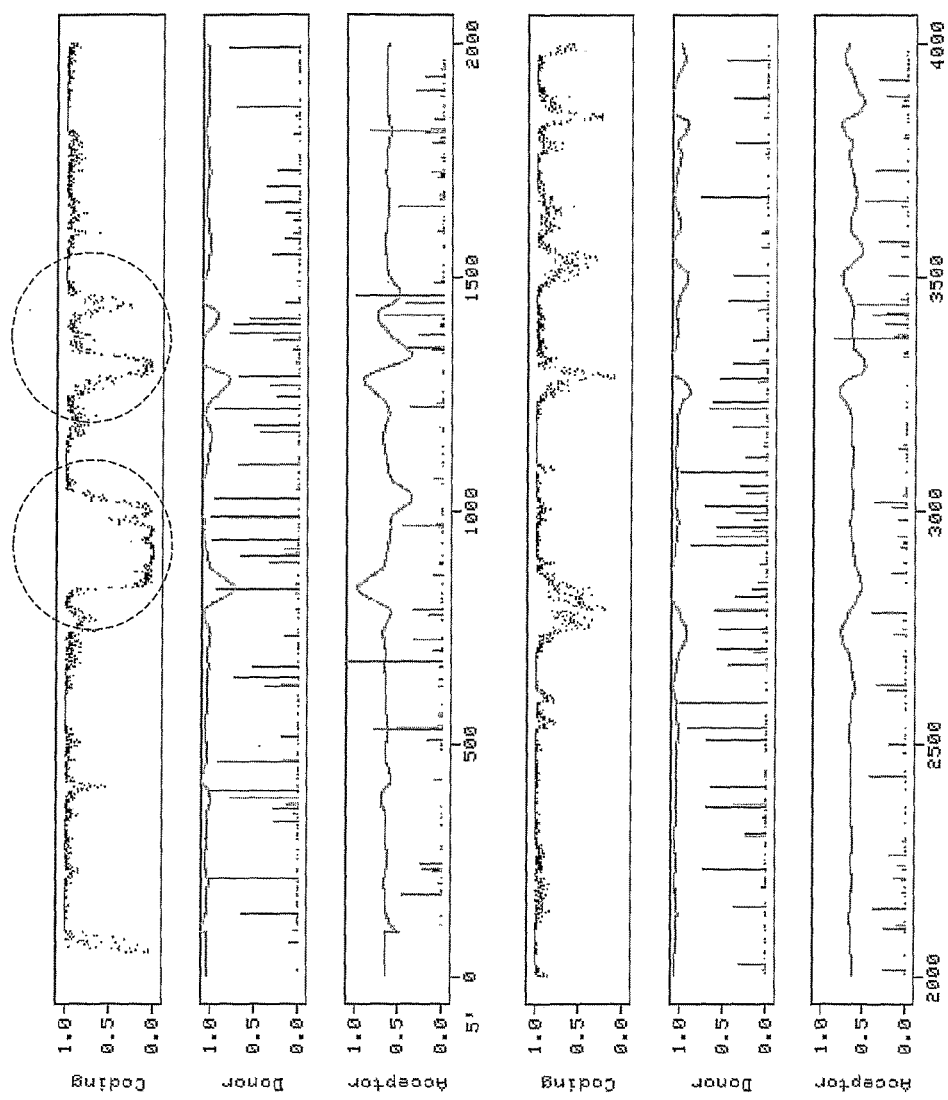
FIGS. 2A and 2B show the intron prediction profile of transcribed region of vector pICH8543. Nucleotide numbers are given on the horizontal axis. The vertical axis shows the probability for corresponding sequence/sequence region to be a coding sequence (coding), to serve as donor site (Donor) or as acceptor site (Acceptor). Circled parts correspond to selected localities where said function conservative differences should be introduced.
Figure 2B:
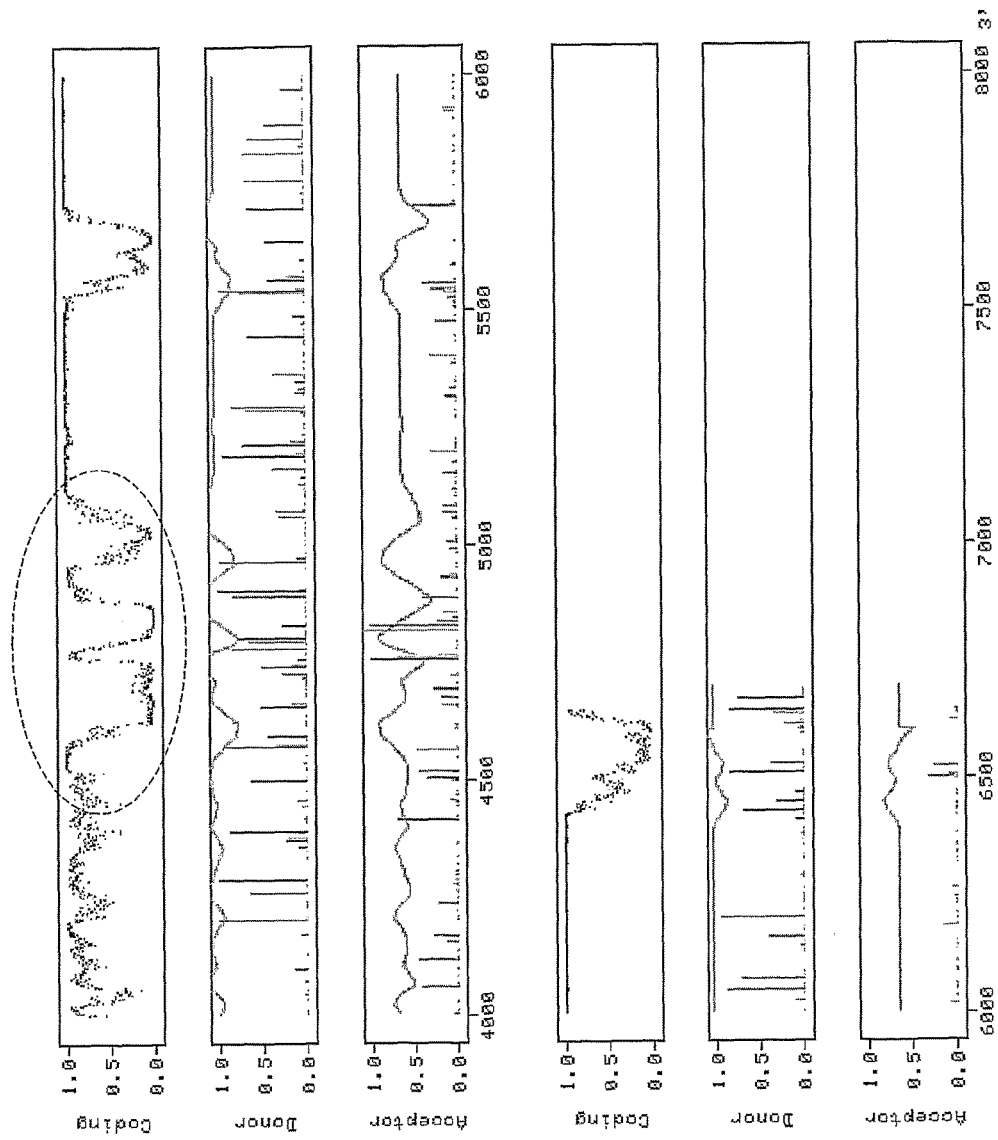
Figure 6A:
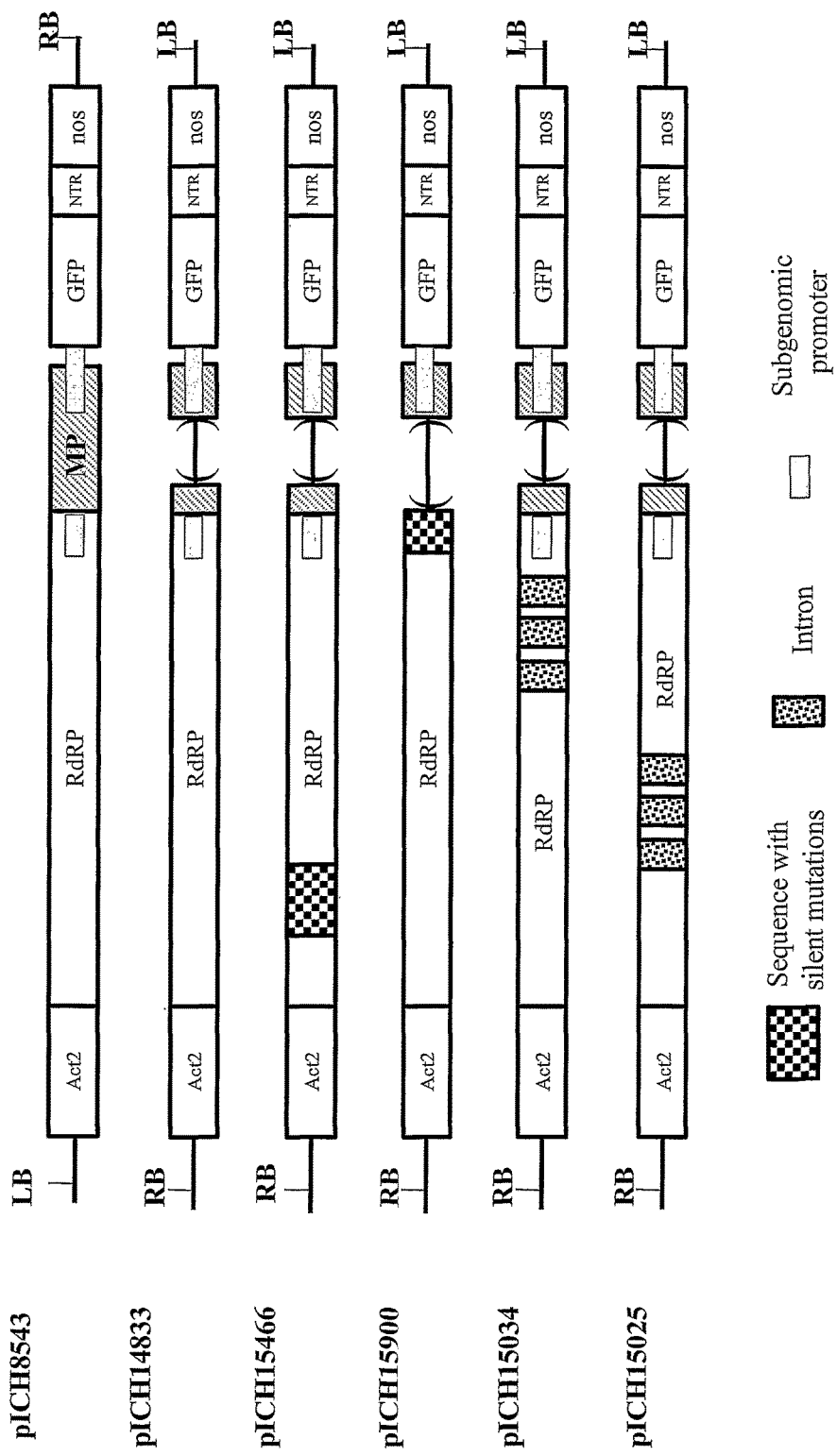
FIGS. 6A and 6B are schematic representations of the T-DNA regions of vectors with and without function-conservative differences according to the invention.

Surprisingly, our first attempt to find evidence that potentially problematic regions do exist, was successful and even more surprisingly, we obtained experimental confirmation by finding unexpectedly an improvement of orders of magnitude. An analysis of the sequence derived from the RNA virus of expression vector pICH8543 (EXAMPLE 1, FIG. 6A) using the NetgeneII server program (http://www.cbs.dtu.dk/services/NetGene2/) for the presence of cryptic introns and RNA splicing sites showed the presence of intron-like regions that might be spliced by the nuclear RNA processing machinery (see circled regions in FIG. 2). There are many other programs that can be used to identify potentially problematic regions (said selected localities) within plant viral RNA sequences, such as exon/intron prediction program (http://genes.mit.edu/GENSCAN.html) or splicing signal prediction program (http://125.itba.mi.cnr.it/~webgene/wwwspliceview.html) for variety of organisms.

Figure 3:
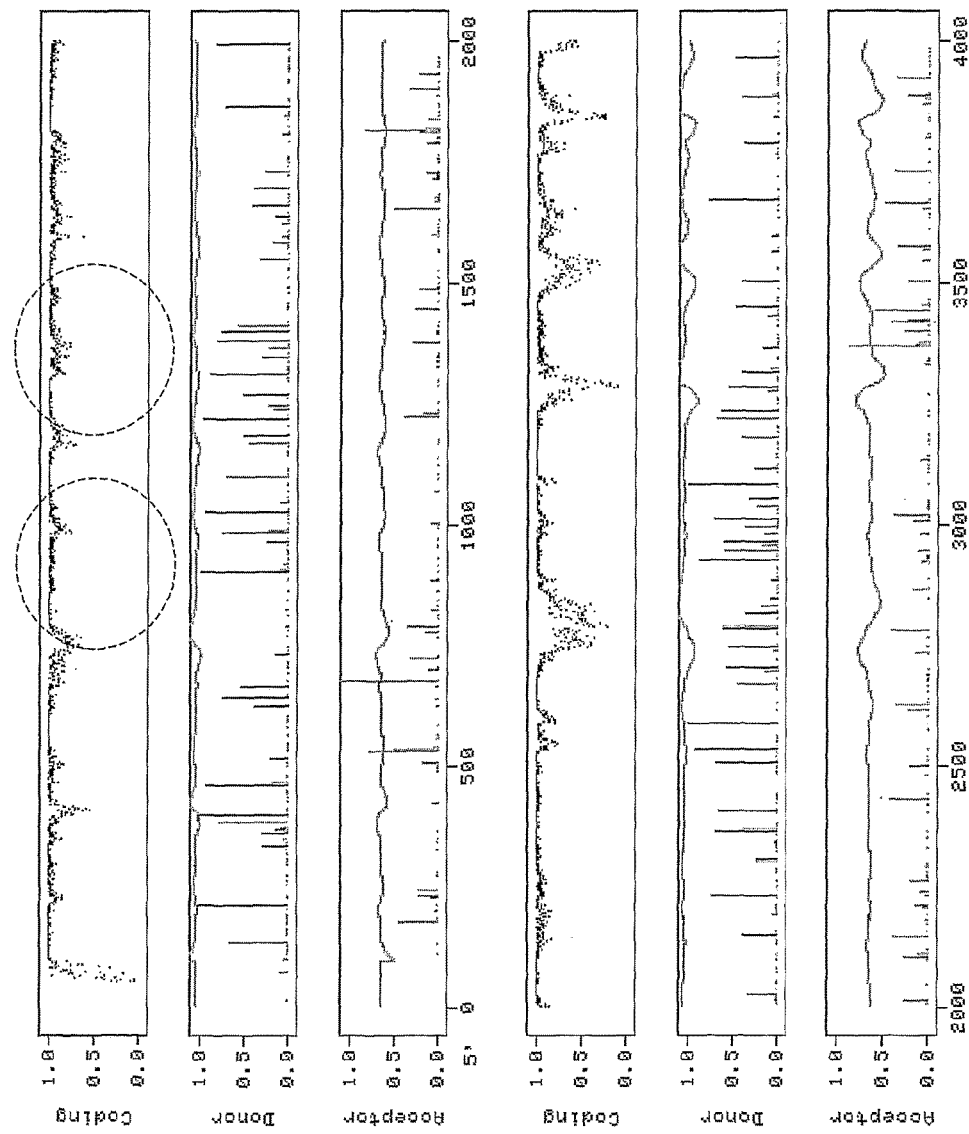
FIG. 3 shows the intron prediction profile of the first half of the transcribed region of vector pICH15466. The circled regions were modified (compare FIG. 2A) with function-conservative differences according to the invention.
Figure 4:
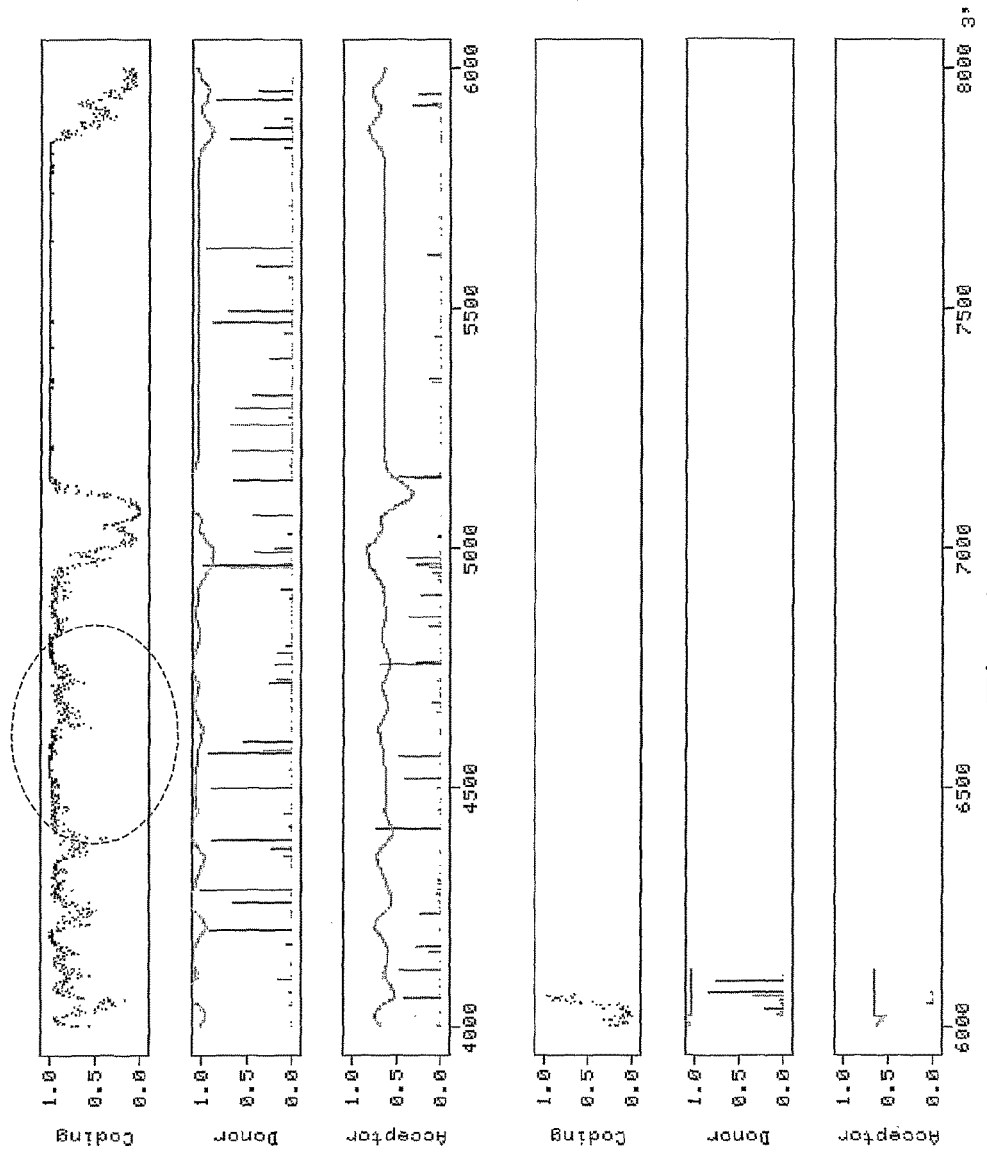
FIG. 4 shows the intron prediction profile of the second half of the transcribed region of pICH1590. The circled regions were modified (compare with FIG. 2B) with function-conservative differences according to the invention.

Considering that all existing programs are not ideal and are subject to mistakes, the potential problematic regions can also be determined experimentally. This can be done by analyzing the transcripts derived from a DNA vector under test in a nuclear environment with the help of such a routine technique as RT-PCR (Frohman, M A., 1989, *Methods Enzymol.*, 218, 340-356) or its more advanced version suitable for precise quantification of the concentration of different transcripts called real-time PCR (Gibson et al., 1996, *Genome Res.*, 6, 995-1001), preferably followed by sequencing of the PCR-amplified products. The function-conservative differences of the invention change dramatically the RNA profile, for example by replacing intron-like sequences with exon-like ones, e.g. by introducing silent mutations with replacement of A/U-rich regions (intron-like) with G/C-rich regions (exon-like) (see FIG. 3, circled regions). Plant introns, unlike exons, are usually A/T(U) rich (Lorkovic, Z J. et al., 2000, *Trends Plant Sci.*, 5, 160-167; Brown, J W. & Simpson, C G. 1998, *Annu. Rev. Plant Physiol. Plant Mol. Biol.*, 49, 77-95; Csank, C. et al., 1990, *Nucl. Acid Res.*, 18, 5133-5141; Goodall & Filipowicz, 1989, *Cell*, 58, 473-483), but there are exceptions, for example when in monocotyledonous plants G/C rich introns were found (Goodall & Filipowicz, 1989, *Cell*, 58, 473-483; Goodall & Filipowicz, 1991, *EMBO J.*, 10, 2635-2644). For practicing this invention, selected localities of high A/T(U) content include not only sequence stretches of at least 20 nucleotides in length with at least 55%, preferably at least 65%, most preferably 80% or a higher of A/T(U) content, but also shorter stretches ("islands") of 6-19 nucleotides in a row of purely A/T(U)-containing sequences. Herein, localities of high A/U content include sequences which are more A- than U-rich, sequences which are A-rich, sequences which are more U- than A-rich, and sequences which are U-rich. Additionally, any transcribed sequence of interest can be tested for post-transcriptional modifications that cause a change in nucleic acids sequences (e.g. RNA splicing) by RT-PCR (Frohman, M A. 1989, *Methods Enzymol.*, 218, 340-356). It is a trivial task for those familiar with the art to use RT-PCR for detecting the regions within RNA that are subject to post-transcriptional modifications like deletions of sequences from the original RNA transcript. In EXAMPLE 2 we demonstrate that the modification of A/U rich region increases the number of GFP expressing cells at least 10-fold. This is clearly demonstrated in FIG. 7 by comparing the areas agroinfiltrated with pICH15466 (modified vector, FIG. 6A) and pICH14833 (control vector, FIG. 6A). Removing the movement protein (MP) allows for an accurate count of primary cells possessing functional RNA replicons, as cell-to-cell movement from the site of primary infection to neighbouring cells does not take place. In EXAMPLE 3, the modification of another U-rich intron-like region containing many cryptic splice sites (FIG. 2B) and covering the subgenomic promoter of the movement protein (MP) was performed (FIG. 4, circled). This modification gave a dramatic effect on the increase of the frequency of replicon formation from viral vector pICH1590. As it was established in protoplast counting experiments (EXAMPLE 3), the increase was approximately 100-fold in comparison with unmodified vector pICH14833 for both tested *Nicotiana* species—*N. benthamiana* and *N. tobacco* (see the corresponding infiltrated areas in FIG. 7, A, B). In general, by using the approaches described in this invention, the frequency of RNA replicon formation can be increased approx. 300-fold, i.e. increasing the proportion of cells with functional replicons from about 0.2% (control vector) to more than 50% (modified vector). We believe this is not the limit and reaching a frequency of 100% is very realistic.

Figure 7A:
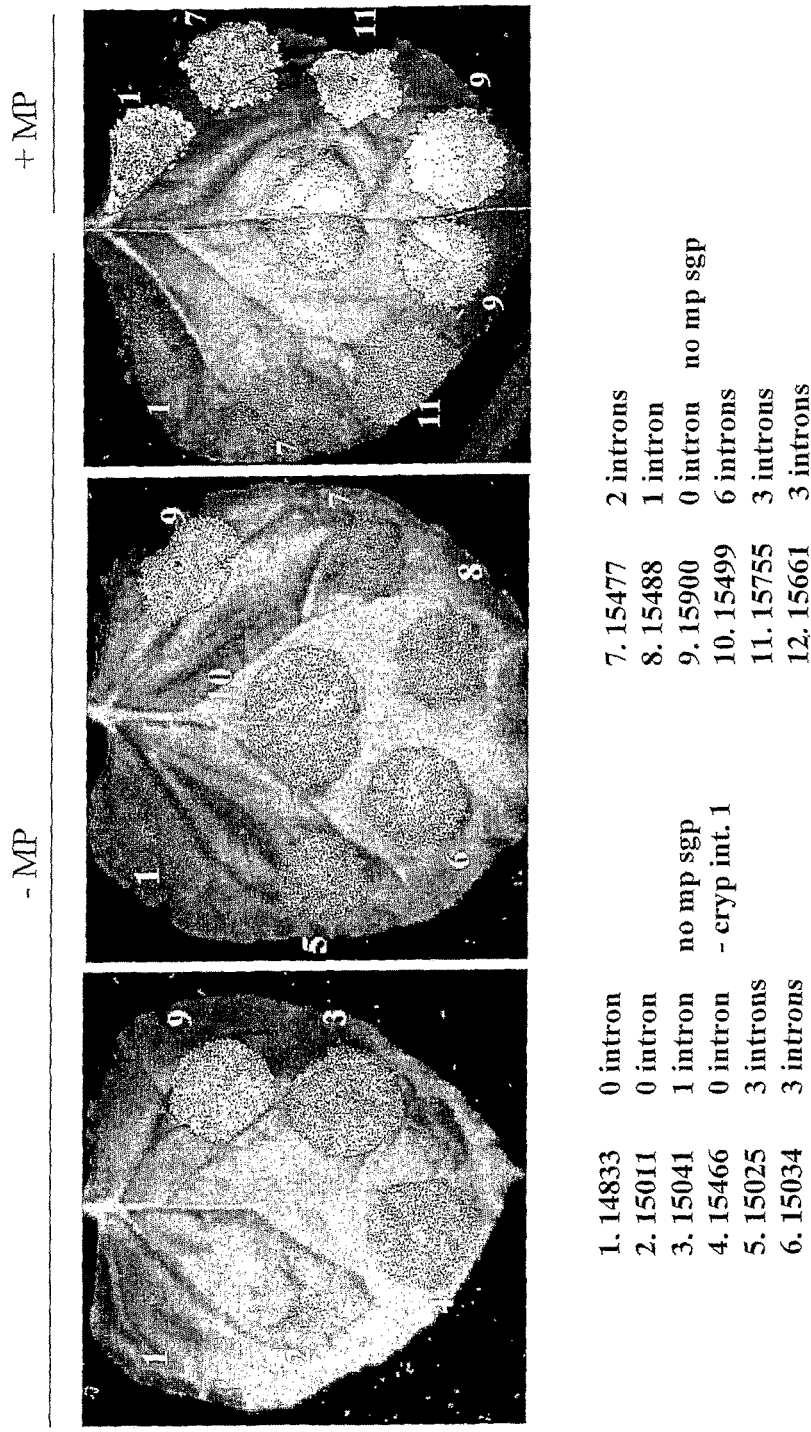
FIGS. 7A, 7B, and 7C show GFP expression after agroinfiltration of viral constructs in *Nicotiana benthamiana* and *Nicotiana tabacum* leaves. The vector (pICH) identification number for each infiltrated area is indicated.
Figure 7B:
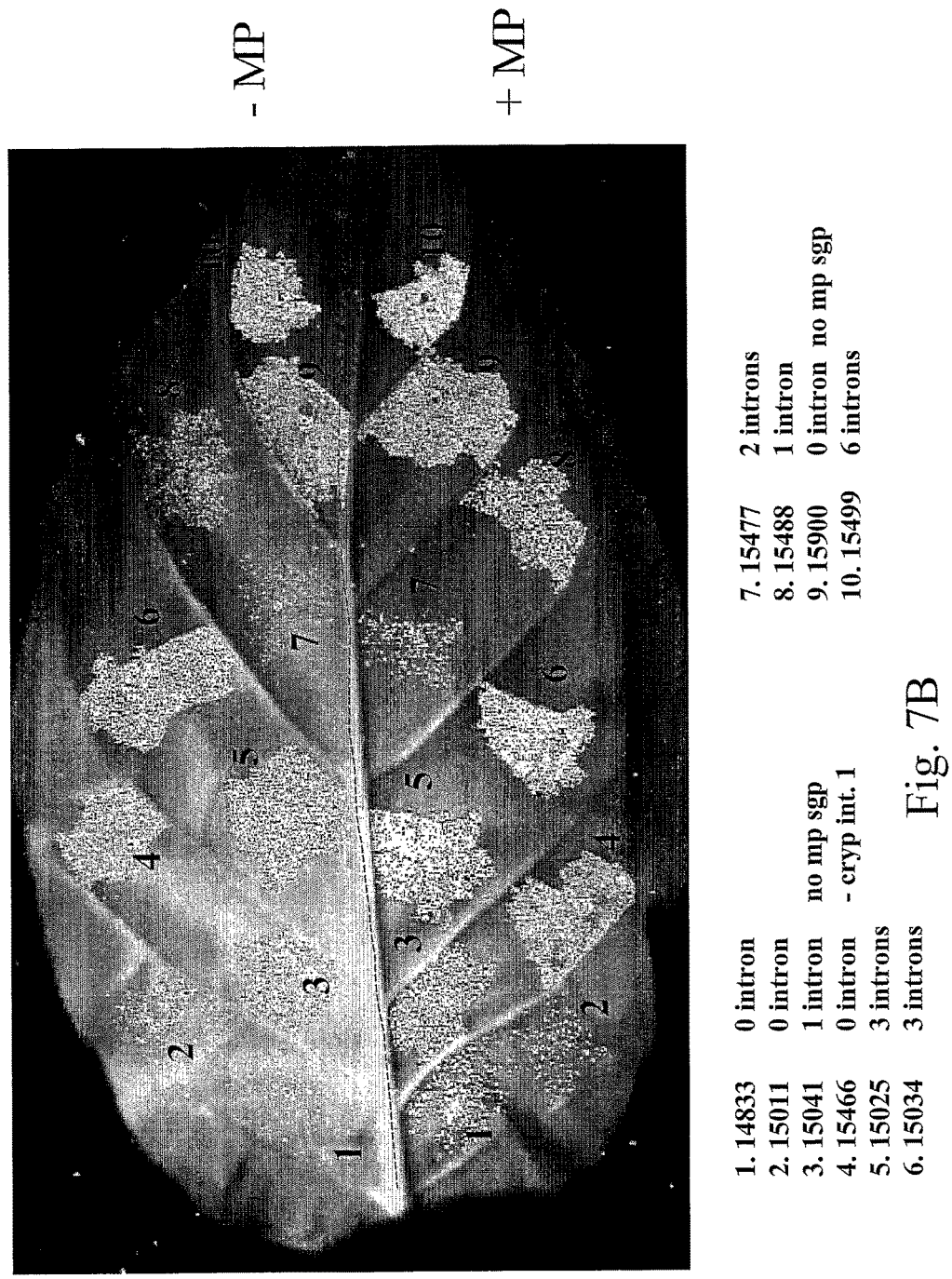
Figure 7C:
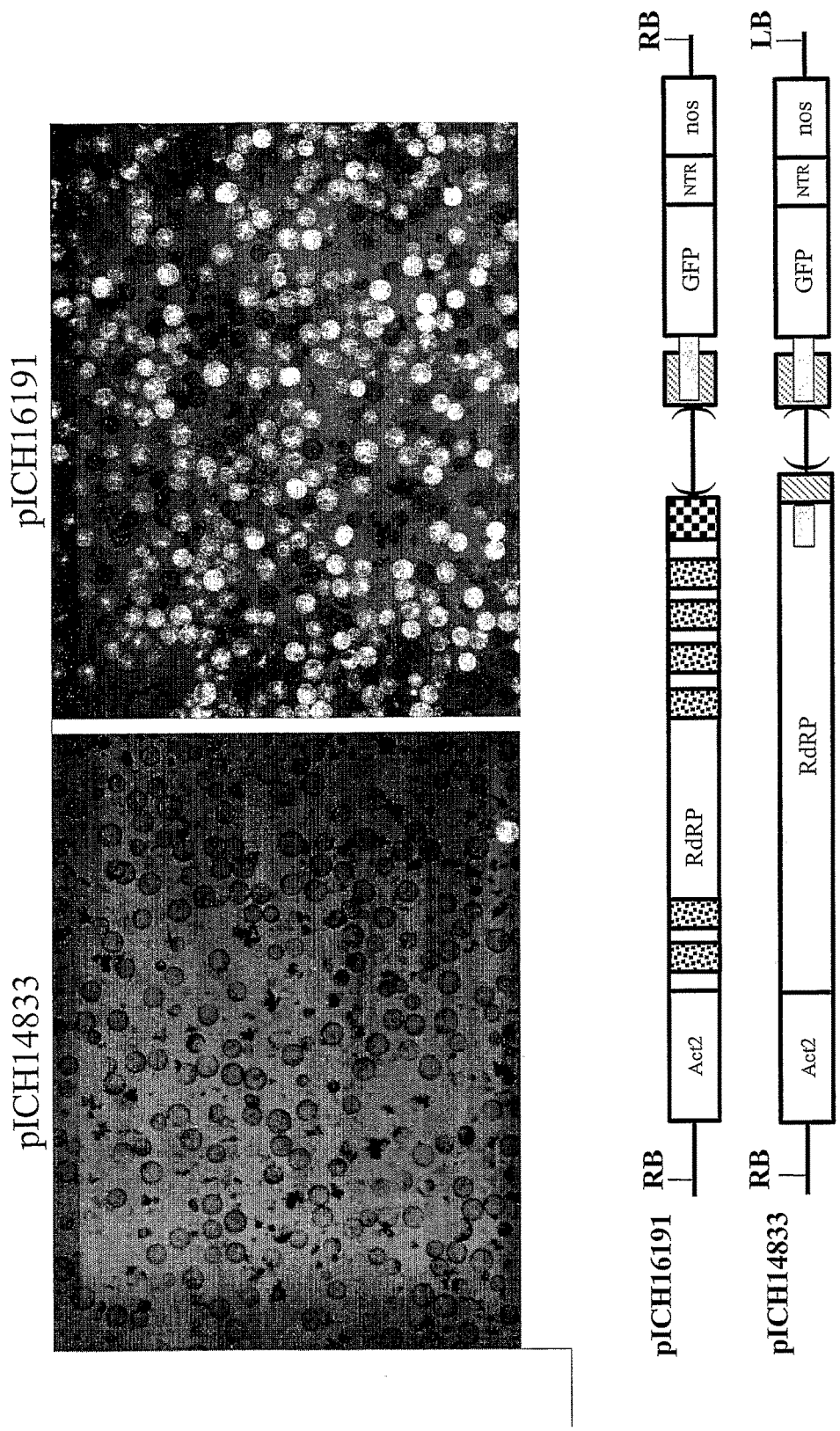

Such a high efficiency of replicon formation opens the door for expressing two or more different genes from two different RNA replicons within the same plant cell, e.g. co-expressing different genes by using plant RNA virus based vectors. The achievement of synchronized release of two or more replicons at same time in the same cell is crucial for such co-expression, as the principle "first come, first served" is especially true for viral vectors. Systemic or cell-to-cell movement does not help, as different viral vectors do normally not overlap in their areas of spread or such overlap is insignificant. Simple calculations demonstrate the importance of the technology described in this invention for achieving co-expression of two sequences of interest in the same plant cell from two replicons. In the case of a non-optimised viral vector with a frequency of functional replicon formation of only 0.2% of all cells, the proportion of cells co-expressing two genes from two different RNA replicons will be 0.2×0.2=0.04%, while for the construct with increased frequency of functional RNA replicon formation (50% or ½ of all cells), said proportion of cells will be 0.5×0.5=0.25 or 25%, e.g. about 625-fold higher. With some of the best performing vectors (e.g. pICH16191, FIG. 7C) the proportion of cells having the functional replicon reaches ca. 90% (FIG. 7C, top right). This means that using such a vector for expressing two different sequences of interest from two independent replicons, co-expression can take place in about 80% of all cells. It appears very likely that the technology can be further improved and that 100% co-expression can be reached.

It is worth to note that function-conservative differences in heterologous sequences of interest to be expressed from said RNA replicon might also be used to increase the frequency of RNA replicon formation, notably in combination with differences in sequences for replicon function. For example, modifications within said sequences of interest can be introduced that are necessary for formation and/or processing of said replicon.

Figure 5A:
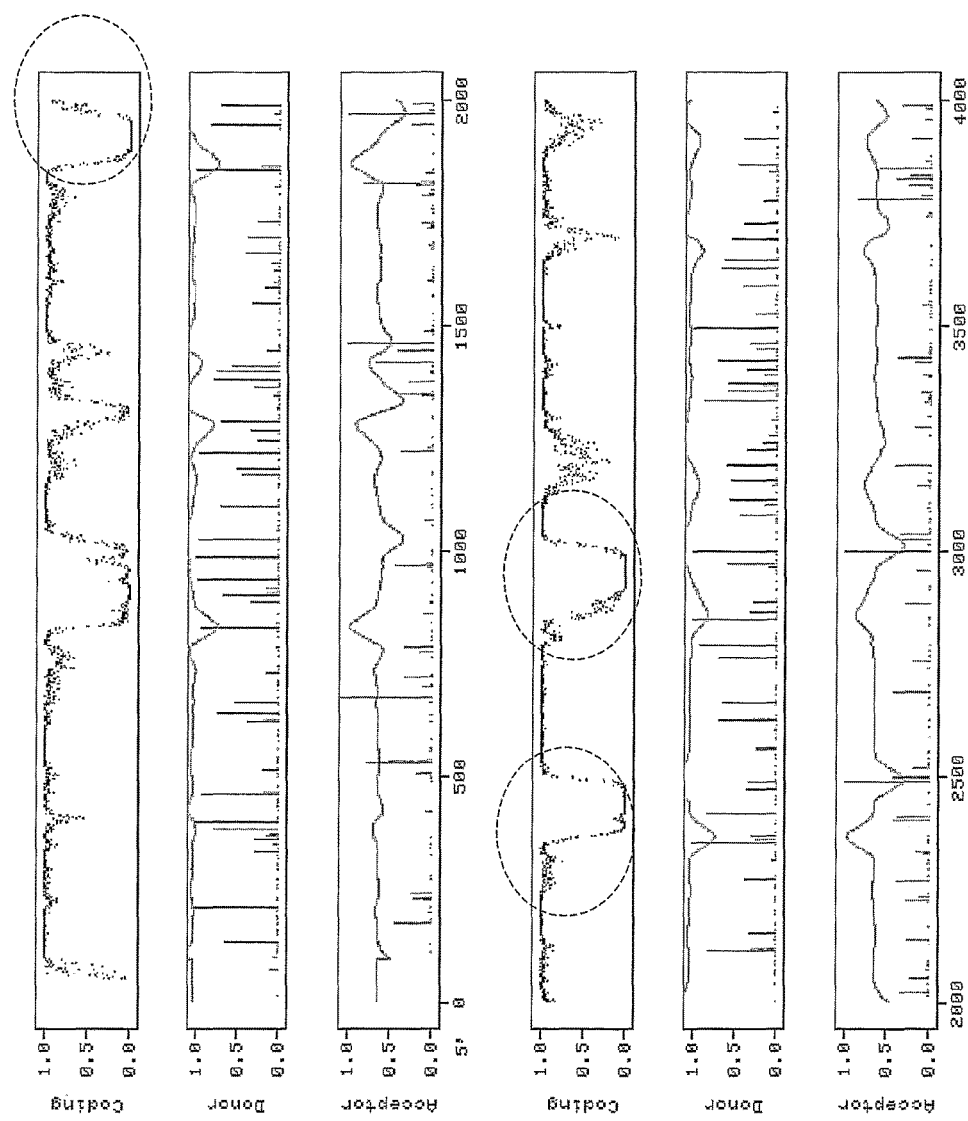
FIGS. 5A and 5B show the intron prediction profile of the transcribed region of pICH15499. The circled regions correspond to six inserted plant nuclear introns.
Figure 5B:
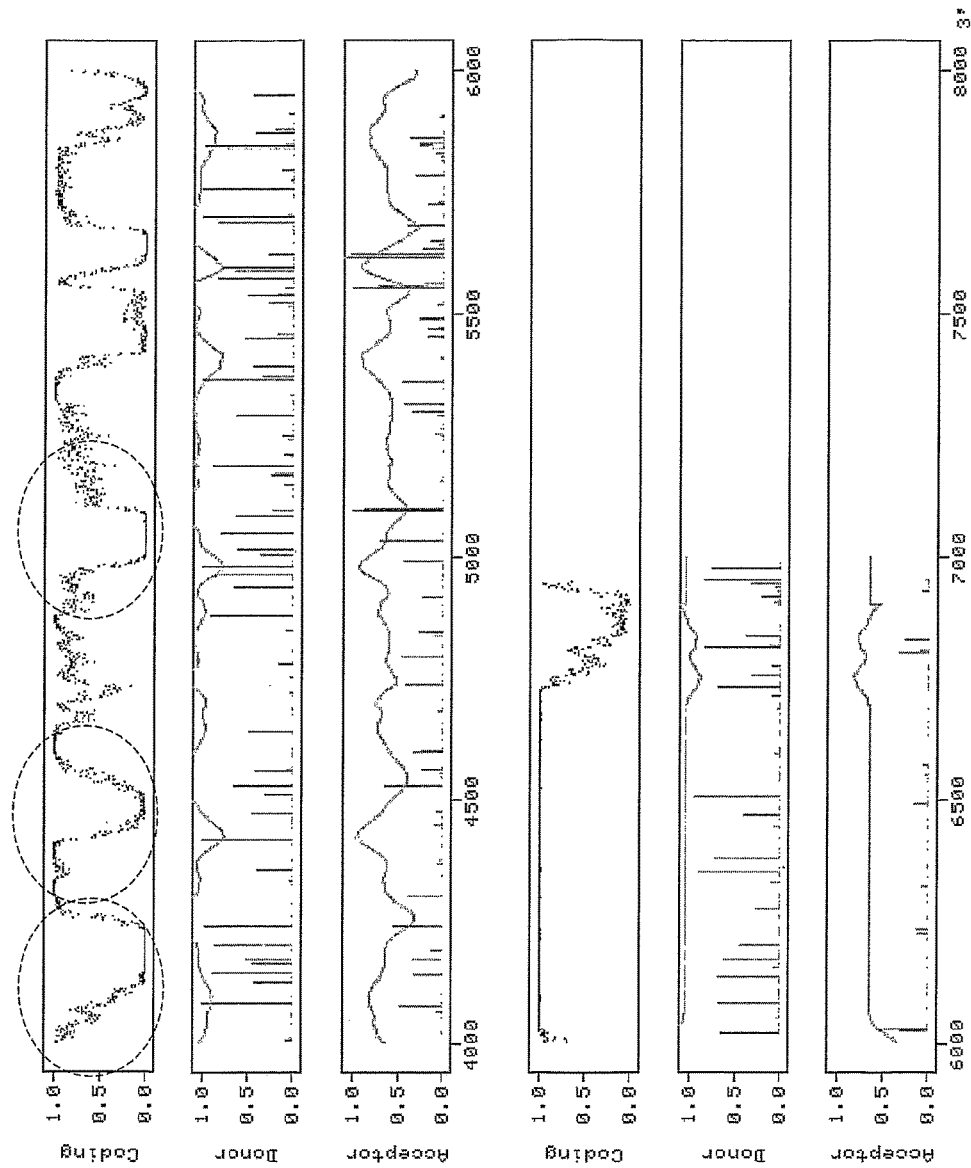
Figure 6B:
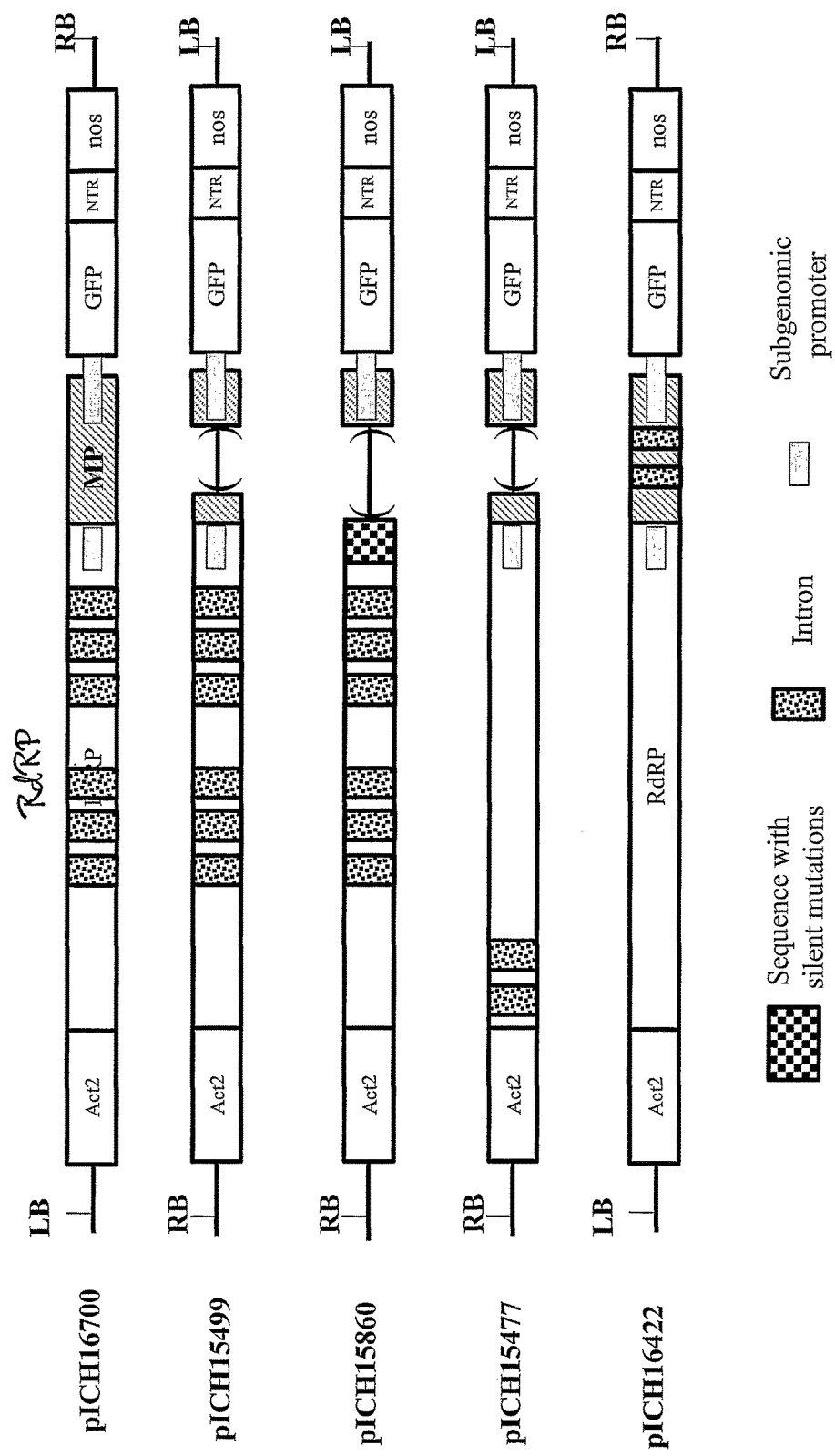

In an important embodiment of this invention, the frequency of replicon formation is improved by inserting nuclear introns in said sequences for replicon function (EXAMPLE 4). The incorporation of introns into the coding region of viral RNA-dependent RNA polymerase (RdRP) (EXAMPLES 4 and 8) resulted in a significant (at least 50-fold) increase in the frequency of replicon formation from (FIG. 7A,B) vectors carrying function-conservative differences as defined herein (pICH15034, pICH15025, pICH15499 in FIG. 6 A,B). The RNA profile for a vector containing 6 inserted introns from *Arabidopsis* is shown in FIG. 5. In another example (EXAMPLE 7), insertion of introns in MP sequences increases the frequency of replicon formation at least 100 times.

Many nuclear introns can be used to practice this invention. Examples of such introns include but are not limited to the introns from rice tpi Act1, and salT genes (Rethmeier et al., 1997, *Plant J.*, 12, 895-899; Xu et al., 1994, *Plant Physiol.*, 100, 459-467; McElroy et al., 1990, *Plant Cell*, 2, 163-171); from the maize Adh1, GapA1, actin and Bz1 genes (Callis et al., 1987, *Genes Dev.*, 1, 1183-11200; Donath et al., 1995, *Plant Mol. Biol.*, 28, 667-676; Maas et al., 1991, *Plant Mol. Biol.*, 16, 199-207; Sinibaldi & Mettler, 1992, in W E Cohn, K Moldave, eds, *Progress in Nucleic Acids Research and Molecular Biology*, vol 42, Academic Press, New York, pp 229-257), from *petunia* rubisco gene SSU301 (Dean et al., 1989, *Plant Cell*, 1, 201-208), *Arabidopsis* A1 EF1α, UBQ10, UBQ3, PAT1 genes (Curie et al., 1993, *Mol. Gen. Genet.* 228, 428-436; Norris et al., 1993, *Plant Mol. Biol.*, 21, 895-906; Rose & Last, 1997, *Plant J.*, 11, 455-464) and many others. Synthetic introns can also be used for this invention. The smallest usable introns or their parts may be limited to splice donor and acceptor sites which usually flank the internal intron sequences. Preferably, the introns should have a size of at least 50 nt., more preferably a size of 100 to 200 nt., but actually there are no limitations regarding the size of the introns. However, the size of the construct should be kept suitable for manipulations. The origin of the intron, its structure and size may be selected individually depending on the nature of the vector. Transient expression experiments may be used for testing the efficiency of a chosen intron or the corresponding intron parts.

The modifications described above have a cumulative effect, e.g. if intron insertion(s) are combined with a modification of the MP subgenomic promoter, the increase in frequency of replicon formation can be approx. 300-fold (EXAMPLE 5). The preferred regions for intron insertions in order to have an increase in the frequency of RNA replicon formation are called selected localities herein. Such localities may contain "intron-like" structures. This is confirmed by the insertion of introns in MP, actually in close proximity to such a problematic region as the MP subgenomic promoter (EXAMPLE 7). A 100-fold increase in frequency of replicon formation was observed. Insertion of introns into "exon-like" regions does not have such a pronounced effect as insertion in said intron-like regions (EXAMPLE 6).

The experiments discussed above were done with transient expression systems based on *Agrobacterium*-mediated DNA precursor delivery into plant cells. However, the most useful application of this invention will be for transgenic plants with a DNA precursor of said RNA replicon stably incorporated into a plant nuclear chromosome. This allows to overcome many limitations of plant viral vector-based systems, such as the restrictions to the maximal size of heterologous sequences viral vectors can tolerate. As the DNA precursor will be present in each cell of the transgenic plant, there is no absolute requirement for systemic movement or for cell to cell movement of the RNA replicon (replicon spreading). This can be compensated by the high efficiency of formation and transport of the RNA replicons of the invention into the cytoplasm. However, the ability of the vector for cell-to-cell movement can be of an additional value, as RNA replicon formation does not always occur in all cells.

Different methods may be used for providing a plant cell with said heterologous DNA. Said vectors may be transformed into plant cells by a Ti-plasmid vector carried by *Agrobacterium* (U.S. Pat. Nos. 5,591,616; 4,940,838; 5,464,763) or particle or microprojectile bombardment (U.S. Pat. No. 5,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of the method for vector delivery may depend on the plant species to be transformed. For example, microprojectile bombardment is generally preferred for monocot transformation, while for dicots, *Agrobacterium*-mediated transformation gives better results in general.

In the examples described below, we used *Agrobacterium*-mediated delivery of vectors (said heterologous DNA) into *Nicotiana* cells. However, said vectors may be introduced into the plants in accordance with any of the standard techniques suitable for stable or transient transformation of the plant species of interest. Transformation techniques for dicotyledonous are well known in the art and include *Agrobacterium*-based techniques and techniques which do not require *Agrobacterium*. Non-*Agrobacterium* techniques involve the uptake of exogenous genetic material directly by protoplasts or cells. These techniques include PEG or electroporation mediated uptake, particle bombardment-mediated delivery and microinjection. Examples of these techniques are described in Paszkowski et al., *EMBO J* 3, 2717-2722 (1984), Potrykus et al., *Mol. Gen. Genet.* 199, 169-177 (1985), Reich et al., Biotechnology 4:1001-1004 (1986), and Klein et al., *Nature* 327, 70-73 (1987). In each case, the transformed cells are regenerated to whole plants using standard techniques.

*Agrobacterium*-mediated transformation is a preferred technique for the transformation of dicotyledons because of its high transformation efficiency and its broad utility with many different species. The many crop species which may be routinely transformed by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (*Brassica*), U.S. Pat. No. 4,795,855 (poplar)).

*Agrobacterium* transformation typically involves the transfer of the binary vector carrying the foreign DNA of interest into an appropriate *Agrobacterium* strain which may depend on the complement of vir genes carried by the host *Agrobacterium* strain either on a co-resident plasmid or chromosomally (Uknes et al., *Plant Cell* 5:159-169 (1993). The transfer of the recombinant binary vector to *Agrobacterium* may be accomplished by a triparental mating procedure using *E. coli* carrying the recombinant binary vector, a helper *E. coli* strain which carries a plasmid such as pRK2013, which is able to mobilize the recombinant binary vector to the target *Agrobacterium* strain. Alternatively, the recombinant binary vector may be transferred to *Agrobacterium* by DNA transformation (Hofgen & Willmitzer, Nucl. Acids Res. 16, 9877 (1988)).

Transformation of the target plant species by recombinant *Agrobacterium* usually involves co-cultivation of the *Agrobacterium* with explants from the plant following protocols known in the art. Transformed tissue carrying an antibiotic or herbicide resistance marker present between the binary plasmid T-DNA borders may be regenerated on selectable medium. This allows the generation of transgenic plants stably transformed on a nuclear chromosome with in T-DNA containing said heterologous DNA of the invention.

In the examples of this invention, in parallel with stable agro-transformation we used agro-inoculation, a method of *Agrobacterium*-mediated delivery of T-DNA for transient expression of gene(s) of interest (Vaquero et al., 1999, *Proc. Natl. Acad. Sci. USA*, 96, 11128-11133). Agro-inoculation is an extremely useful tool not only for small-to-middle scale recombinant protein production systems, but as an element of a vector optimisation system, allowing to obtain fast results with different variants of constructs.

The invention can also be used for large-scale/industrial production of recombinant proteins. Overnight cultures of *Agrobacterium* were used in our experiments. The overnight culture was prepared for agro-infiltration, as described in the prior art (Marillonnet et al., 2004, *Proc. Natl. Acad. Sci. USA.*, 101, 6853-6857). Usually, an overnight culture reaches an optical density (O.D.) of 3-3.5 units at a wavelength 600 nm and is diluted 3-5 times before agro-infiltration, yielding in general 5-9×10⁹ colony forming units (Turpen et al., 1993, *J. Virol. Methods*, 42, 227-240). We have found that a 10², preferably a 10³ and more preferably a 10⁴ fold dilution of auch an overnight culture works very efficiently, especially in combination with sequences for replicon function having said function-conservative differences as described herein. Surprisingly, the vectors in infiltrated tobacco leaves further improved their performance giving better yield of GFP with increasing dilutions of the transforming Agrobacteria. For example, a 10³-fold dilution gave better result than a 10²-fold dilution. A 10²-fold dilution provides better GFP yield than a 10-fold dilution. A possible explanation for this phenomenon is the negative effect of highly concentrated *Agrobacterium* suspension on the function of a viral vector, e.g. on cell-to-cell movement, possibly as the result of a plant response to high concentrations of pathogenic bacteria. This phenomenon is of special value for large-scale industrial protein expression processes, as it allows to reduce the amount of agrobacteria required for recombinant protein production via agro-infiltration by at least one order of magnitude compared to prior art processes.

In EXAMPLE 9 of this invention, a DNA precursor of an inactivated viral RNA-based replicon is stably incorporated into chromosomal DNA. Said replicon is optimised according to the invention. In addition, the replicon contains a structure preventing expression of the sequence of interest. Expression as well as formation of the functional RNA replicon can be triggered by flipping one part of the construct with the help of site-specific recombination. Said flipping can lead to the formation of two introns as well as to the assembly of a functional sequence of interest. The system described in EXAMPLE 9 shows not only the optimisation of a viral vector but also the solution for avoiding "leakiness" of constructs stably integrated into chromosomal DNA, including the "leaky" expression of the gene of interest from said construct. In many applications, it is crucial to have zero level expression in the uninduced state, especially for cytotoxic proteins or for achieving high biosafety standards with plant expression systems for expressing technical or pharmaceutical proteins.

Transcription of the heterologous DNA and/or of said recombinase can be under the control of an inducible or any other regulated (e.g. developmentally regulated) promoter. Inducible promoters can be divided into two categories according to their induction conditions: those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847,102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 6,063,985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol.*, 11, 146-151) and Padidam, M (2003, *Curr. Opin. Plant Biol.*, 6, 169-177). Other examples of inducible promoters are promoters which control the expression of pathogenesis-related (PR) genes in plants. These promoters can be induced by treatment of a plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662).

Figure 9:
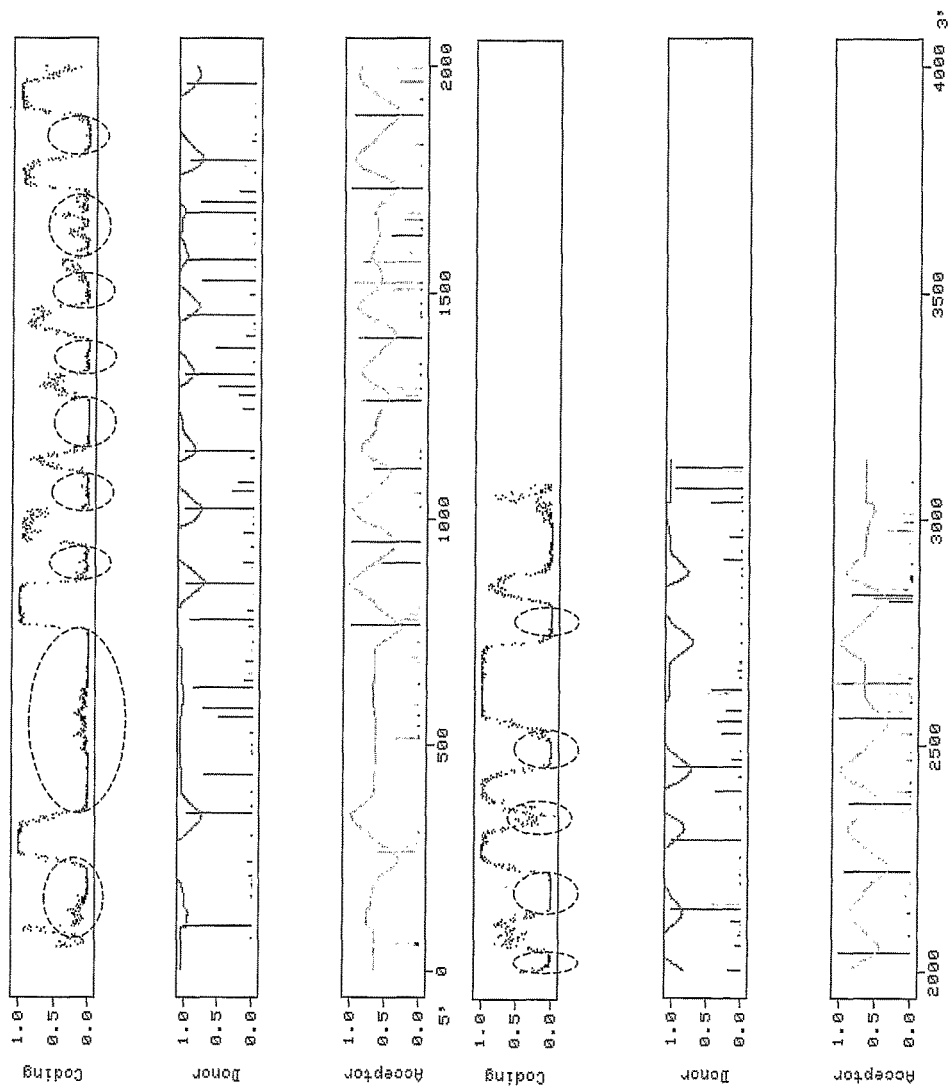
FIG. 9 shows an intron prediction profile for *Arabidopsis thaliana* meiosis-specific gene AtDMC1 (GenBank Acc. No U76670), using the direct strand (+ strand). The intron-coding regions are circled.
Figure 10A:
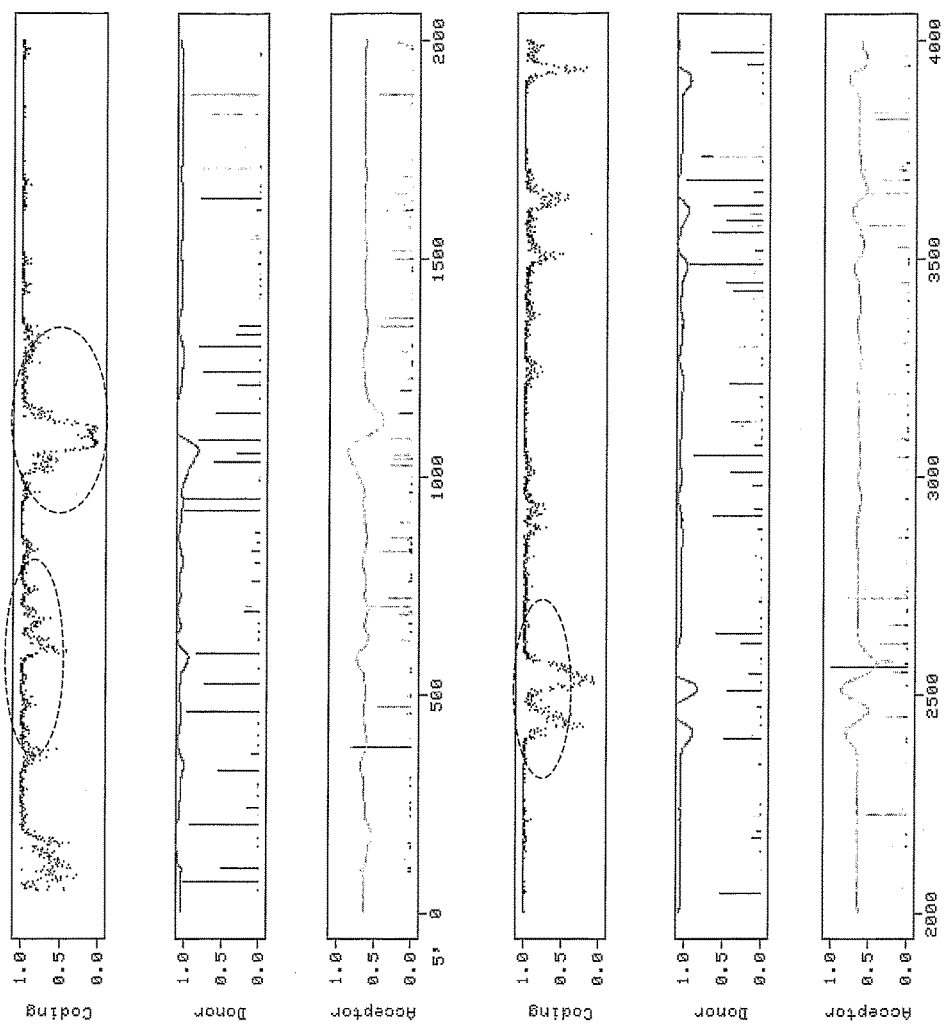
FIGS. 10A and 10B show the prediction of potential problematic regions (circled) within the direct strand (+ strand) of Potato Virus X (PVX) genome (GenBank Acc. No. AF172259).
Figure 10B:
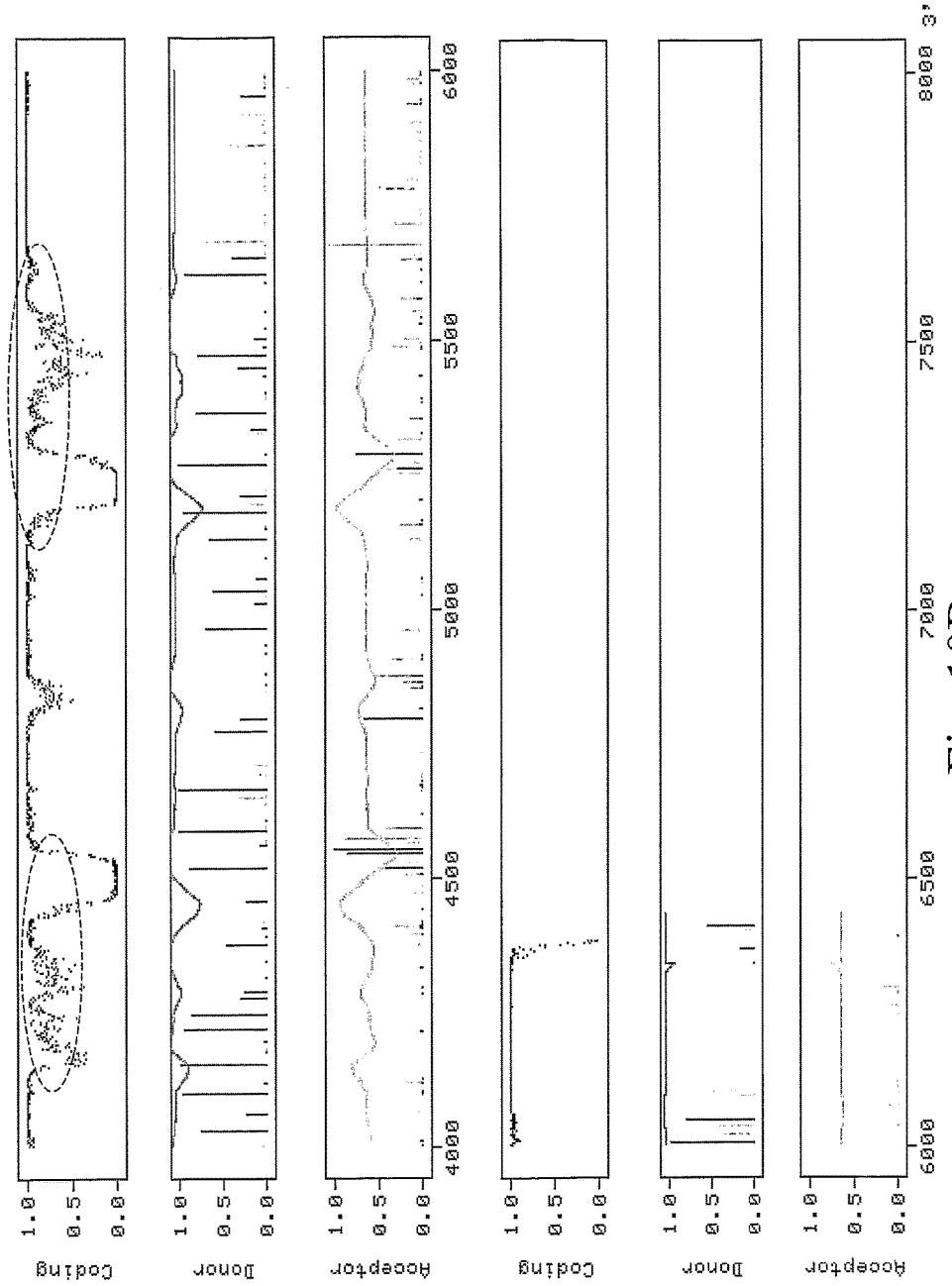
Figure 11A:
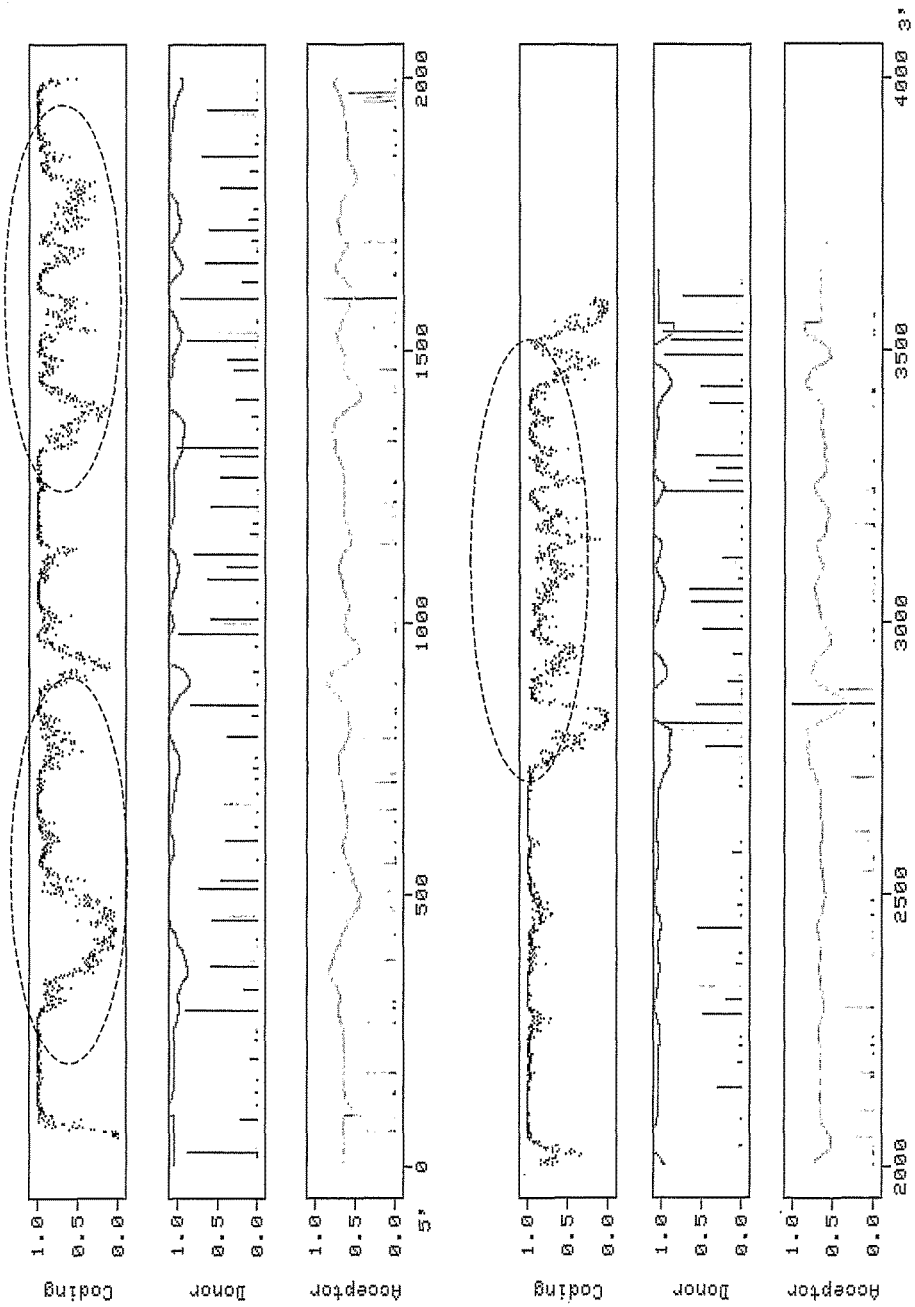
FIGS. 11A, 11B, and 11C show the prediction of potential problematic regions (circled) of the direct strand (+ strand) of alfalfa mosaic virus genomes of RNA1 (GenBank Acc. No K02703), RNA2 (GenBank Acc. No K02702) and RNA3 (GenBank Acc. No L00163), respectively.
Figure 11B:
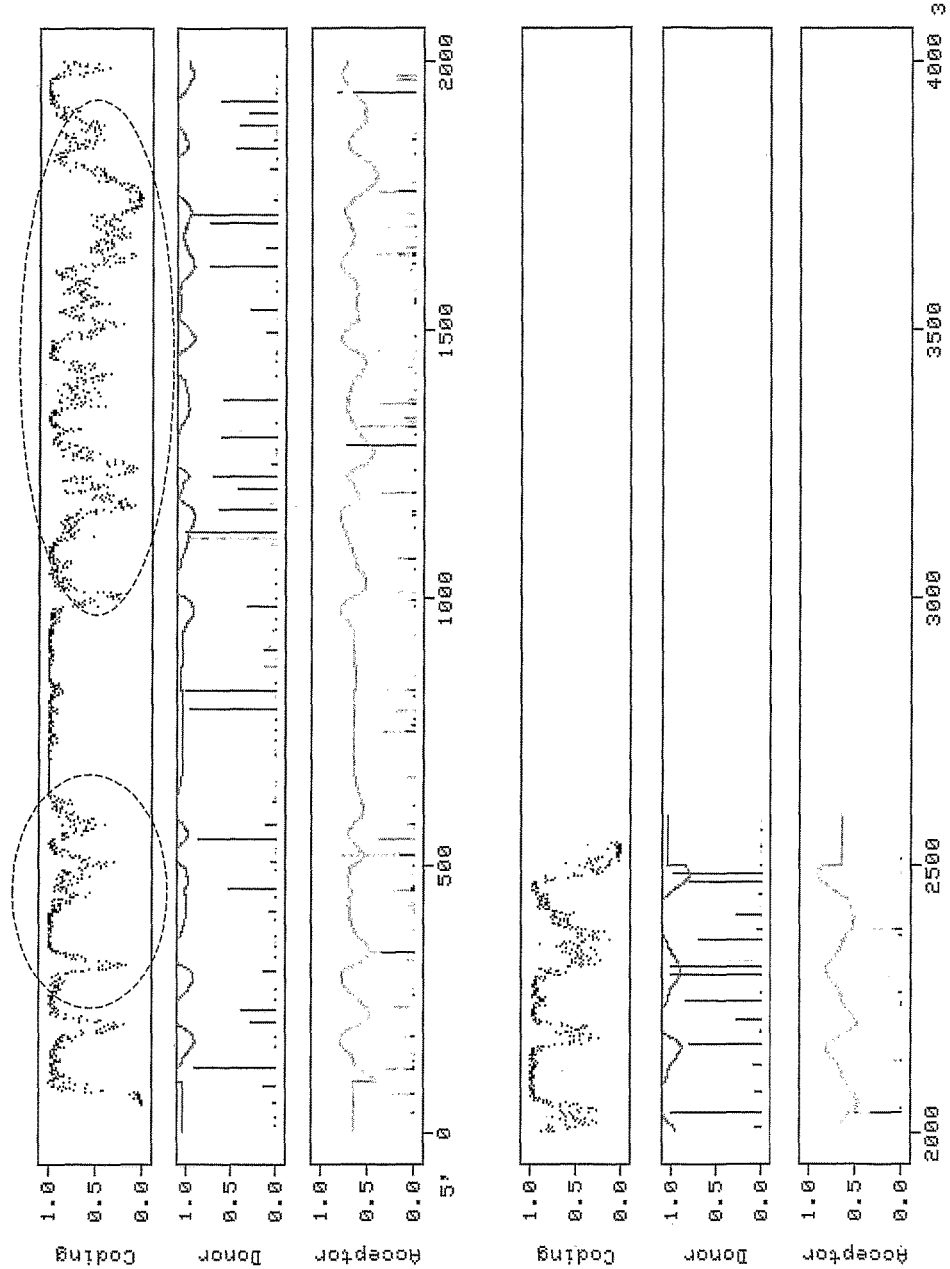
Figure 11C:
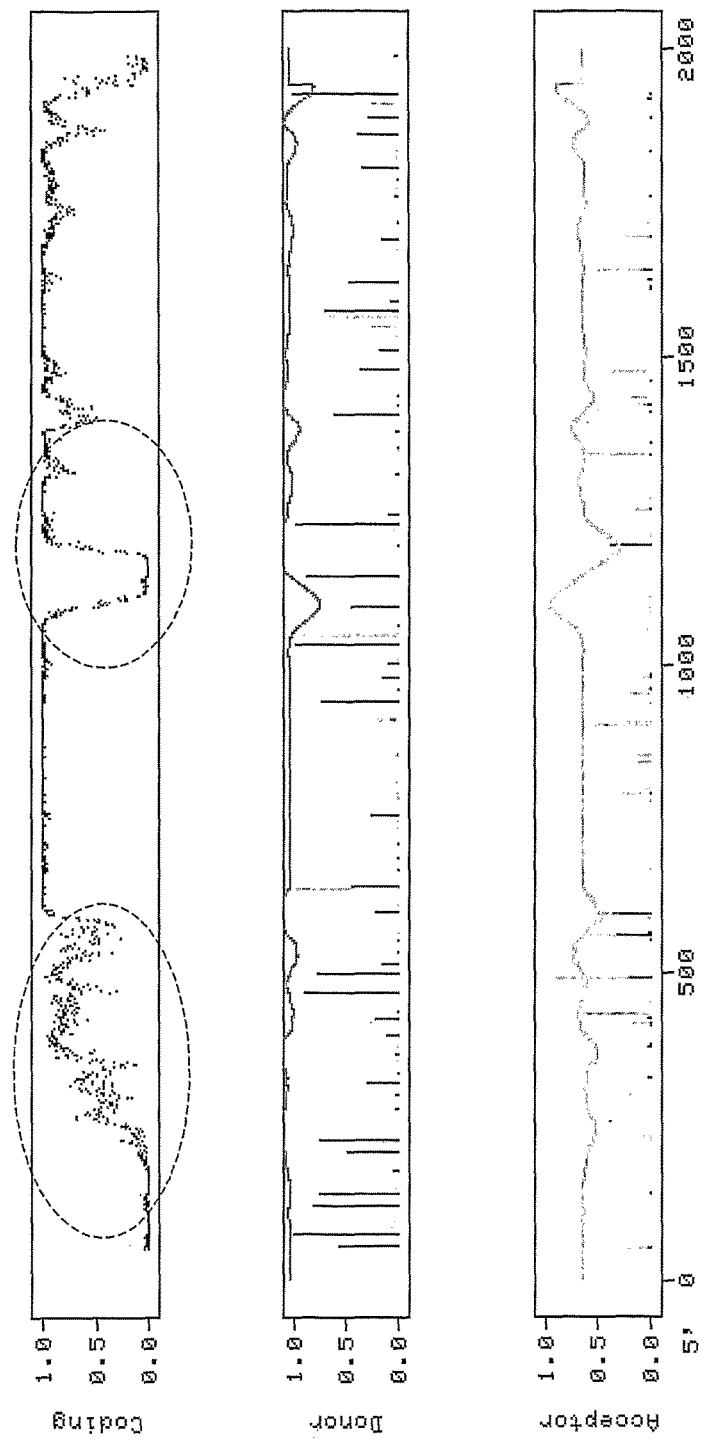

This invention is not limited to TMV-based vectors described in examples 1-9, but can be extended to replicons based on other plant RNA viruses. The analysis of other plant viral RNA sequences (EXAMPLE 10, FIGS. 10, 11) shows selected localities very similar to those described for TMV and the sequences of pre-mRNA of plant nuclear genes (FIG. 9). This is strong evidence supporting the suggestion that, using the approaches described in this invention, practically any plant RNA virus-derived replicon can be improved fundamentally by removing/replacing problematic regions and/or inserting nuclear introns.

The present invention is preferably carried out with higher multi-cellular plants, parts thereof, or cell cultures thereof. Plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing this invention include, but not restricted to, representatives of Gramineae, Compositeae, Solanaceae and Rosaceae.

Further preferred species for the use in this invention are plants from the following genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea,* and the Olyreae, the Pharoideae and many others.

Most preferred plants for this invention are plants that do not enter the animal or human food chain like *Nicotiana* species, e.g. *Nicotiana benthamiana* and *Nicotiana tabacum*.

Proteins of interest, their fragments (functional or non-functional) and their artificial derivatives that can be expressed in plants or plants cells using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), oil modifying enzymes (like fatty acids desaturases, elongases etc), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, enzymes involved in the synthesis of polyhydroxylalkanoates (PHA), acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, *potyvirus* coat protein, CMV coat protein, TMV coat protein, *luteovirus* replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, proteins having an enzymatic activity in fatty acids biosynthesis and modifications, e.g. the peroxysomal β-oxidation of fatty acids in plant cells, acyl-CoA oxidase, 3-ketoacyl-CoA thiolase, lipase, maize acetyl-CoA-carboxylase, etc.; 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4-D monooxygenase, acetolactate synthase or acetohydroxyacid synthase (ALS, AHAS), polygalacturonase, Taq polymerase, bacterial nitrilase, many other enzymes of bacterial or phage origin including restriction endonucleases, methylases, DNA and RNA ligases, DNA and RNA polymerases, reverse transcriptases, nucleases (DNases and RNases), phosphatases, transferases etc.

The present invention can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Human or animal health protein may be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsin, trypsinogen, al-antitrypsin (AAT), human serum albumin, glucocerebrosidases, native cholera toxin B, thrombin, human gastric lipase, granulocyte-macrophage colony stimulating factor (GM-CMF), serpin, lactoferrin, lysozyme, oleosin, prothrombin, alpha-galactosidase, as well as function-conservative proteins like fusions, mutant versions and synthetic derivatives of the above proteins.

The content of International patent application PCT/EP03/12530 and European patent application 04016012.9 are incorporated herein by reference in their entireties.

EXAMPLES

The following examples are presented to illustrate the present invention. Modifications and variations may be made without departing from the spirit and scope of the invention.

Example 1

Construction of a TMV-Based RNA Vector

Cloned cDNAs of the crucifer-infecting *tobamovirus* (cr-TMV; Dorokhov et al., 1994, *FEBS Lett.* 350, 5-8) and of the turnip vein-clearing virus (TVCV; Lartey et al., 1994, *Arch. Virol.* 138, 287-298) were obtained from Prof. Atabekov from Moscow University, Russia. A viral vector containing a green fluorescence protein (GFP) gene was made in several cloning steps. The resulting construct, pICH8543 (FIG. 6A), contains in sequential order: a 787 bp fragment from the *Arabidopsis* actin 2 promoter (ACT2, ref An et al, 1996, GenBank accession AB026654, by 57962 to 58748), the 5' end of TVCV (GenBank accession BRU03387, bp 1 to 5455), a fragment of cr-TMV (GenBank accession Z29370, by 5457 to 5677, with thymine 5606 changed to cytosine to remove the start codon of the coat protein, CP), sequences "taa tcg ata act cga g", a synthetic GFP (sGFP) gene, cr-TMV 3' nontranslated region (3' NTR; GenBank accession Z29370, bp 6078 to 6312), and finally the nopaline synthase (Nos) terminator. The entire fragment was cloned between the T-DNA left (LB) and right (RB) borders of pICBV10, a $Carb^R$ pBIN19-derived binary vector. pICH8543 was transformed into *Agrobacterium* strain GV3101 and infiltrated into a *Nicotiana benthamiana* leaf. Foci of GFP fluorescence that appeared at 3 dpi grew and became confluent. Surprisingly, even though most cells in the infiltrated area finally expressed GFP due to viral replication and movement, only a fraction of the cells initiated viral replication, as detected by a number of independent GFP expressing foci. It became clear that the limiting factor is not DNA delivery to plant cells, since infiltration of *Nicotiana benthamiana* leaves with a GFP gene under control of the 35S promoter leads to GFP expression in almost every cell in the infiltrated area (not shown).

To confirm this observation, we made a viral vector construct containing a mutation in the MP. This construct, called pICH14833, is similar to pICH8543 but differs by a deletion of 389 bp in the MP gene, upstream of the EcoRI site present in the MP. The sequence of the NcoI to EcoRI fragment that includes this deletion is given in the annex as SEQ ID No. 1. The entire viral construct (from the ACT2 promoter to the Nos terminator) was cloned between the T-DNA left and right borders of pICBV49, a pBIN19-derived $Kan^R$ binary vector. Due to the deletion in the MP, replicons produced from this construct cannot move from cell to cell but are able to replicate autonomously within a cell. Cell to cell movement can be restored when MP is provided in trans, e.g. from a constitutive promoter such as the cauliflower mosaic virus 35S promoter.

To make an MP expression construct, the TVCV MP gene was amplified by PCR from cloned TVCV cDNA (GenBank accession Z29370, by 4802 to 5628) and subcloned in a binary vector under control of the 35S promoter. The resulting construct, called pICH10745 (not shown), and pICH14833 were transformed into *Agrobacterium* strain GV3101 and various dilutions of an overnight culture were infiltrated in *Nicotiana benthamiana* leaves as described by English and colleagues (1997, *Plant J.*, 12, 597-603), except that the infiltration media lacked acetosyringone. Infiltration of pICH14833 alone led to the appearance of a few GFP expressing cells within the infiltrated area. By counting protoplasts prepared from the infiltrated area, we found that only one to three protoplasts expressed GFP from a total of 500 protoplasts (0.2 to 0.6%). Coinfiltration of pICH14833 and pICH10745 led to the formation of GFP-expressing foci that grew from each initial GFP-expressing cell. Ultimately, due to cell-to-cell movement, a large proportion of cells in the infiltrated area expressed GFP (FIG. 7A).

RNA viruses such as tobamoviruses replicate in the cytoplasm and never enter the nucleus. Therefore, they have evolved in an environment where they are not exposed to the nuclear pre-mRNA processing machinery. As a result, it is not surprising that RNA replicon transcripts generated in the nucleus from artificial viral constructs may not be recognized and processed properly by the RNA processing machinery. Moreover, RNA replicons from viral vectors are very large: approximately 7,000 nt in the case of the replicon based on TMV. Very few plant genes have such a large size and the majority of such genes contains introns that facilitate processing of the pre-mRNAs, export from the nucleus, and that improve the stability of the processed transcripts. We therefore hypothesized that modifications of the pre-mRNAs that would increase the efficiency of accurate processing and of export of correctly processed transcripts from the nucleus to the cytosol would lead to an increase of the number of cells that would initiate viral replication. It turned out that there are two approaches can be used to make RNA virus-based vectors that can more efficiently initiate viral replication after DNA delivery to the nucleus: (1) one approach is the removal of sequence features that might induce unwanted processing events (such as alternative splicing events using cryptic splice sites, or premature termination events); (2) a second approach is the addition of introns to increase the amount of properly processed transcripts, to improve export of the RNA from the nucleus to the cytoplasm, and/or to improve stability of the transcripts.

Example 2

Removal of Intron-Like Sequences Increases the Frequency of Viral RNA Replicon Formation in the Cytoplasm We analyzed the sequence of the RNA replicon from pICH4351 using the Netgenell server program (http://www.cbs.dtu.dk/services/NetGene2/) and noticed several intron-like sequence features that might induce alternative splicing events. One such feature is a 0.6 kb uridine-rich region (corresponding to nt 827 to 1462 in GenBank accession BRU03387) at the beginning of the RdRP (FIG. 2A). This region was replaced in pICH14833 bp a PCR-mutagenized sequence that differs from the original sequence by a 54 nucleotide substitution (sequence given in the annex as SEQ ID No. 2; cf. FIG. 3). The 52 nucleotide substitutions were made to replace T-rich sequences by more GC-rich sequences. All nucleotide substitutions were made silent so as not to change the RdRP protein sequence. This mutagenized fragment also contains two nucleotide substitutions (at position 829 and 1459; coordinates relative to GenBank accession BRU03387) that were introduced to remove putative cryptic splice donor and acceptor sites, respectively. To test the effect of these mutations, the resulting clone pICH15466 (FIG. 6A) was agroinfiltrated in *N. benthamiana* leaves with or without pICH10745 (movement protein in trans). Eight days after infiltration, a 10-fold increase in the number of GFP expressing cells was observed in the area infiltrated with pICH15466 (compared to pICH14833, FIG. 7). This suggests that removal of intron-like sequences from the viral amplicon prevents unwanted alternative splicing events and results in more efficient initiation of viral replication. Coinfiltration of pICH15466 and pICH10745 leads to cell-to-cell movement of the modified replicon at a similar speed as a non-modified replicon. This shows that the modification of the RNA sequence did not affect cell to cell movement of the viral vector.

Example 3

Removal of Intron-Like Sequences in the MP Subgenomic Promoter

A second potentially problematic region corresponds to the MP subgenomic promoter (FIG. 2B). This region is very T-rich and resembles intron sequences very closely. As a consequence, many cryptic splice donor and acceptor sites are predicted in nearby sequences by intron prediction programs. Unfortunately, modifications cannot be made easily to this region without affecting subgenomic promoter function. We decided to completely mutagenize the entire region without regard for the subgenomic promoter, and to provide MP in trans to compensate for the expected loss of MP expression. As MP will not be expressed from this construct, we also deleted most of MP sequence except for the 3' sequences that contain the CP subgenomic promoter which is required to drive expression of the gene of interest. We therefore replaced a 383 bp fragment in pICH14833 (bp 4584 to 5455 in GenBank accession BRU03387) by a 297 bp mutagenized fragment (SEQ ID No. 3). The resulting construct pICH15900 (FIG. 6A) was agroinfiltrated in *Nicotiana benthamiana* leaves with or without pICH10745. Interestingly, a huge increase in the number of cells initiating replication was detected in comparison to leaf areas infiltrated by pICH14833. By counting GFP-expressing protoplasts prepared from infiltrated leaf areas, we estimate that this modification results in a 80 to 100-fold increase in the number of cells initiating viral replication compared to the unmodified pICH14833. pICH15900 was coinfiltrated with pICH10745 (p35S-MP expression cassette) and an increase in GFP fluorescence was detected due to cell to cell movement. This increase was however very limited because so many cells already expressed GFP even in the absence of cell-to-cell movement. A 1000-fold dilution (corresponding approximately to a calculated OD of 0.004 at 600 nm) of the *agrobacterium* suspension containing pICH15900 coinfiltrated with a 5-fold diluted suspension of agrobacteria containing pICH10745 (corresponding approximately to a calculated OD of 0.8 at 600 nm) gave rise to separate GFP expression foci. Fluorescent foci were as bright and of the same size as control foci obtained with pICH14833. This tells us that the modification in pICH15900 and the delivery of MP in trans do not compromise functionality of the replicon regarding the level of replication, expression of the gene of interest and cell-to-ell movement. The same constructs (pICH14933 and pICH15900, with or without pICH10745) were coinfiltrated to *Nicotiana tabacum* leaves. The modifications in pICH15900 lead to a similar increase in the number of cells initiating replication (in comparison to pICH14833) as they did in *N. benthamiana*.

Example 4

Addition of Introns Improves the Frequency of Formation of Functional RNA Rep/Icons in the Cytoplasm We tested whether the addition of introns into viral pro-replicon sequences would increase the frequency of initiation of replication. Two constructs were made, pICH15025 and pICH15034 (FIG. 6A), each containing three different *Arabidopsis thaliana* introns in two different regions of the RdRP. pICH15025 was designed to contain introns in the middle of the RdRP, while pICH15034 contains introns in the 3' end of the RdRP, upstream of the MP subgenomic promoter. The introns were amplified by PCR from *Arabidopsis* genomic DNA and incorporated into viral sequences using PCR with primers overlapping the planned intron/exon junctions. The fragments containing the introns were subcloned into pICH14833 as an Aval HindIII fragment (SEQ ID No. 4 in the annex) to make pICH15025 or as a Pst1 NcoI fragment (SEQ ID No. 5 in the annexe) to make pICH15034.

Both constructs were separately agroinfiltrated into *N. benthamiana* leaves and compared to pICH14833. Both constructs significantly increased the number of cells initiating viral replication (FIG. 7A). This increase was estimated to be on the order of a 50-fold improvement relative to pICH14833. Both constructs were also coinfiltrated with an MP expressing clone, and cell-to-cell movement was found to be identical to clones without introns. Both constructs were also tested in *N. tabacum*, and a similar improvement was observed as in *N. benthamiana* (FIG. 7B).

A third clone was made, pICH15499, which contained all 6 introns (FIG. 5, 6B, 7A, 7B). This construct was tested in *N. benthamiana* and *N. tabacum*. This construct was more efficient than each individual construct with 3 introns, but the improvement was however less than additive.

Example 5

Addition of Introns and Removal of Intron-Like Sequences Increases the Frequency of the Formation of Functional RNA Replicons in the Cytoplasm Removing intron-like features and adding additional introns in one construct showed that both types of modifications can contribute to improve initiation of viral replication. We subcloned the 6 introns of pICH15499 into pICH15900, which contains the mutagenized MP subgenomic promoter region. The resulting clone pICH15860 (FIG. 6B) was infiltrated into *N. benthamiana* leaves and found to work significantly better than either parental clones within the range of approximately 50% to 90% of all protoplasts expressing GFP (FIG. 7). The best performing construct contains introns within the RdRP region and modified MP subgenomic promoter region (pICH16191, FIG. 7C). In comparison to a clone without any modification, this represents an 80- to 300-fold improvement. This construct was also coinfiltrated with a MP-expressing construct (pICH10745) and it was found that the modifications did not compromize cell-to-cell movement or replication.

Example 6

Not all Intron Additions Increase the Frequency of Appearance of Functional RNA Replicons in the Cytoplasm We inserted two different *Arabidopsis* introns at the beginning of the RdRP, resulting in clone pICH15477 (the sequence of this region is shown as SEQ ID No. 6 in the annex). The sequence in this region already looks very "exon-like" (e.g. GC-rich without cryptic splice sites) before the addition of introns. No improvement on replication of viral initiation was seen with this construct. Therefore, not any addition of an intron will result in an improvement of the viral vector. It appears that the position chosen for intron insertion or mutagenesis is an important parameter. For example, all intron insertions or nucleotide substitutions that were made in regions near problematic structures such as the MP subgenomic promoter resulted in large improvements, while insertions of introns into sequences that are already "exon-like" did not.

Example 7

Insertion of Introns in MP Sequences Increase the Frequency of Viral Replicon Formation We first made a frameshift in the MP by digestion with the restriction enzyme AvrII, filling and religation. We then inserted two introns in the MP. The resulting clone pICH16422 (FIG. 6B) was infiltrated in *Nicotiana benthamiana* leaves. An about 100-fold increase in the number of cells containing the functional viral replicon was detected.

Example 8

Insertion of Introns into a MP Containing Vector Improves the Frequency of Initiation of Viral Replication of Autonomous Functional Clones A Kpn1 EcoRI fragment was subcloned from pICH15499 into pICH8543. The resulting clone, 16700 (FIG. 6B) contained a complete viral vector with 6 introns in the RdRP. This clone was infiltrated in *N. benthamiana* leaf and efficiently initiated replication. This clone was also able to move from cell to cell without the need to provide additional MP in trans.

Example 9

Activation of an Inactive Replicon Stably Integrated on a Chromosome

Figure 8:
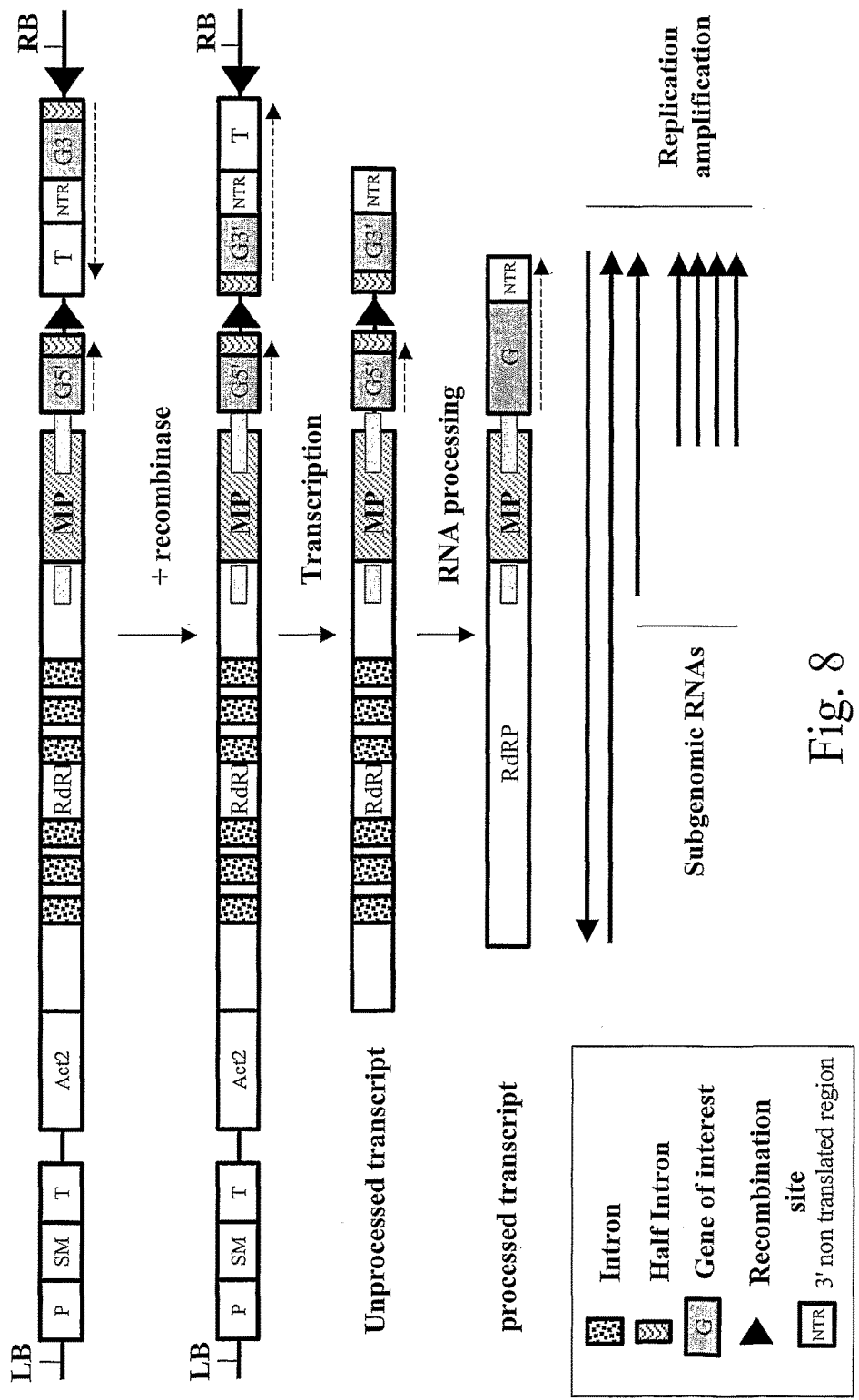
FIG. 8 is a schematic representation of an RNA virus-based replicon precursor designed according to the present invention, which gives zero expression level of the gene of interest (GFP, indicated by G) in the non-induced state.
P—transcription promoter; T—transcription termination region; SM—selectable marker gene; Ac2—promoter of *Arabidopsis* ACTIN2 gene; RdRP viral RNA-dependent RNA polymerase; MP—viral movement protein; NTR—viral 3' non-translated region.

It is also possible to stably transform intron-containing viral vector constructs in transgenic plants. To avoid deleterious viral replication that would inhibit plant growth, an inactive clone (pro-replicon) can be made by having a part of the vector present in antisense orientation (FIG. 8). Incorporation of recombination sites and of intron sequences at the extremities of the inverted fragment allow this fragment to be 'flipped' in the correct orientation by using an appropriate recombinase. Recombination sites will be completely eliminated from the replicon by splicing. Introns in the pro-replicon allow efficient initiation of replication after recombination and transcription. In one specific example, the recombination sites are located within the gene of interest and downstream of the pro-replicon. Such a configuration prevents any gene expression before recombination. Other configurations can be considered where the recombination sites are located in other areas of the pro-replicon such as in the RdRP and upstream of the promoter. Intron sequences at the recombination site have the advantage of allowing to completely remove the recombination site from the replicon, but also increases the efficiency of viral replication, as described before.

Figure 12:
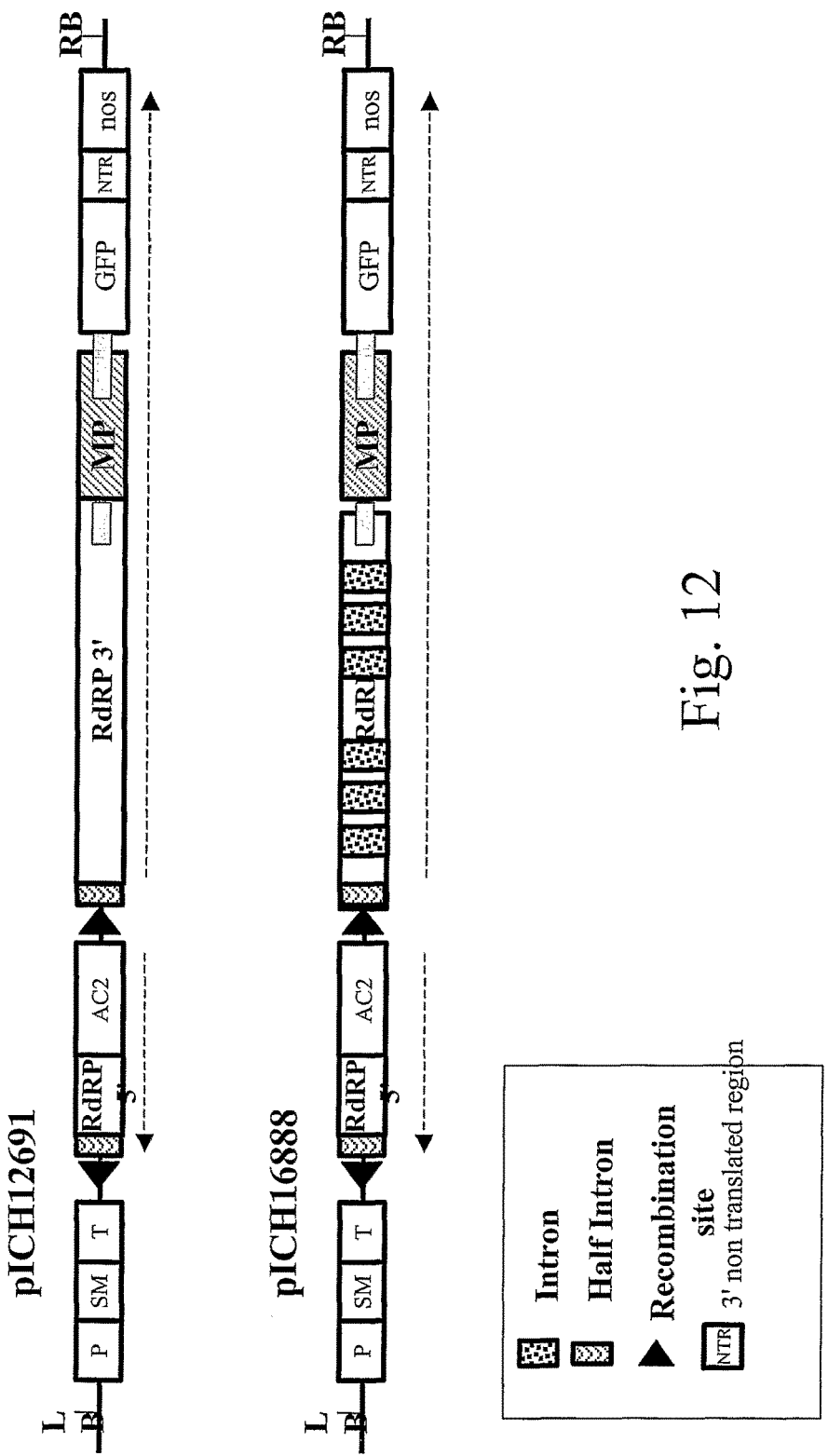
FIG. 12 depicts T-DNA regions of constructs pICH12691 and pICH16888.
P—transcription promoter; T—transcription termination region; SM—selectable marker gene; Ac2—promoter of *Arabidopsis* ACTIN2 gene; RdRP viral RNA-dependent RNA polymerase; MP—viral movement protein; NTR—viral 3' non-translated region.
Figure 13:
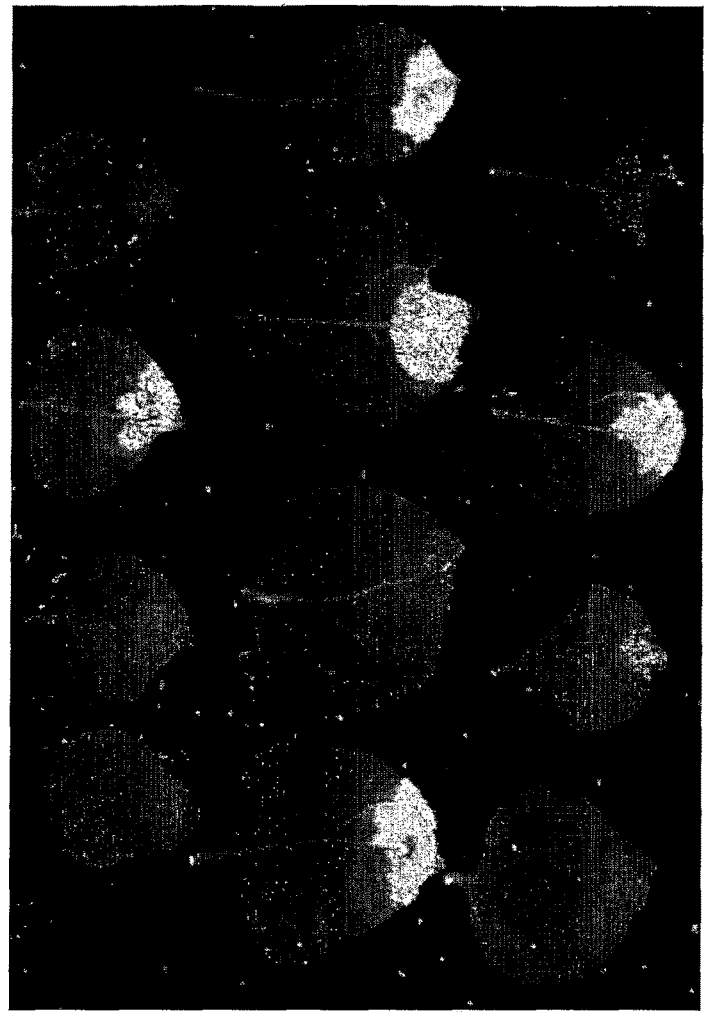
FIG. 13 shows leaves under UV light of different stably transformed *N. benthamiana* lines carrying the T-DNA regions of either pICH12691 (left panel) or pICH16888 (right panel). The leaves were agro-infiltrated with vectors (pICH10881 or pICH14313) providing integrase.
Figure 13:
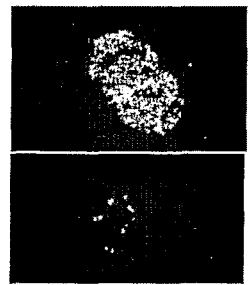

The flipped part can be located at the 3' end of the vector (as shown in FIG. 8), in the middle or at the 5' end, as shown in FIG. 12. Two constructs were made, pICH12691 (containing only one intron at the recombination site) and pICH16888 containing 6 additional introns in the RdRP. The sequence of the entire T-DNA region of pICH12691 is given in SEQ ID No. 7. pICH16888 is similar to pICH12691, but, in addition, contains the three introns described above in pICH15025 (SEQ ID No. 4) and the three introns described in pICH15034 (SEQ ID No. 5) inserted in the same position as in these constructs, respectively. Both pICH12691 and pICH16888 were stably transformed in Nicotiana benthamiana using Kanamycin selection as follows. The constructs pICH12691 and pICH16888 were separately immobilized into A. tumefaciens (GV3101) and were separately used for Agrobacterium-mediated leaf discs transformation of Nicotiana plants as described by Horsh and colleagues (1985, Science, 227, 1229-1231) with minor modifications. Leaf discs were co-cultivated for 30 min in an agrobacterial suspension in Murashige and Skoog (MS) basal medium supplemented with 1 mg/L of alpha-naphthaleneacetic acid (NAA), 0.5 mg/L 6-benzaminopurine (BAP), 200 microM acetosirengone (AS), pH5.5-5.6. Then leaf discs were placed on sterile Whatman® filter paper for removal of excessive liquid and transferred onto solid co-cultivation medium (0.8% agar prepared on MS supplemented as described above) for 48 hours cultivation in darkness at 22-23° C. After co-cultivation, leaf discs were placed on selective regeneration medium (0.8% agar prepared on MS supplemented with 1 mg/L BAP, 0.1 mg/L NAA, 1 mg/L MES (pH pH 5.7-5.8), 300 mg/L cefataxim, 50 mg/L kanamycin). After 3-6 weeks of cultivation on regeneration medium, the shoots regenerated from kanamycin-resistant plant cells were transferred onto rooting selective medium (0.8% agar prepared on MS supplemented with 300 mg/L cefotaxim, 200 mg/L timentin to facilitate the elimination of agrobacterium, 50 mg/L kanamycin, pH 5.7-5.8). Regenerated transformants were transferred to a glasshouse and tested by infiltration with a syringe without needle with an agrobacterium suspension containing an integrase expression construct (pICH10881: actin2 promoter—PhiC31 integrase; or pICH14313: Zea maize transposable element Spm promoter-PhiC31 integrase). More pICH16888 transformants exhibited viral replication foci after infiltration with the integrase construct than transformants of pICH12691 (FIG. 13). In addition, transformants of pICH16888 displayed more viral initiation foci per infiltration.

Example 10

Plant Viral RNA Sequences Contain Potentially Unstable Regions

The analysis of RNA profile of selected plant RNA viruses as well as one well characterised plant gene (At-DMC1) was performed by using the Netgenell server program (http://www.cbs.dtu.dk/services/NetGene2/). The RNA profile shown in FIG. 9 for AtDMC1 clearly reflects the presence of 14 introns (circled), previously identified by comparing the cDNA and genomic DNA sequences. It is evident that RNA profiles of two plant viruses have regions (see the FIGS. 10, 11) which might cause problems for the stability of said RNA, if they are placed in plant nuclear environment. We have analysed the RNA profiles of several other representatives of plant RNA viruses (not shown), such as Brome Mosaic Virus, different strains of TMV, and many others. All of them have potential problematic regions that might compromise the efficiency of plant RNA virus-based replicon formation if delivered into the plant cell as DNA precursors.

Example 11

Optimized Vectors Work in Other Species

A fully optimized construct containing the mutagenized region (described in pICH15466) and 16 introns (including the six introns of pICH15860, the two introns of pICH16422 and eight additional introns) was made. In summary this construct contains introns inserted at the following positions (given relative to TVCV sequence, GenBank accession BRU03387): nt 209, nt 828, nt 1169, nt 1378, nt 1622, nt 1844, nt 2228, nt 2589, nt 2944, nt 3143, nt 3381, nt 3672, nt 3850, nt 4299, nt 5287, nt 5444.

This construct was tested for expression in Beta vulgaris. Infiltration of the entire plant was performed as described next. Agrobacteria carrying pICH18711 were inoculated to 300 ml of LB containing 50 µg/ml Rifampicin and 50 µg/ml Kanamycin (selection for the binary vector) and grown until saturation. The bacteria were pelleted at 4800 g for 10 min and resuspended in 3 l of infiltration buffer (10 mM MES pH 5.5, 10 mM MgSO$_4$) in order get a 10-fold dilution relative to the saturated Agrobacterium culture. A beaker containing the infiltration solution was placed in an exsiccator (30 mm diameter), with the aerial parts of a plant dipped in the solution. A vacuum was applied for two minutes using a Type PM 16763-860.3 pump from KNF Neuberger (Freiburg, Germany), reaching from 0.5 to 0.9 bar. The plants were returned to the greenhouse under standard conditions.

Figure 14:
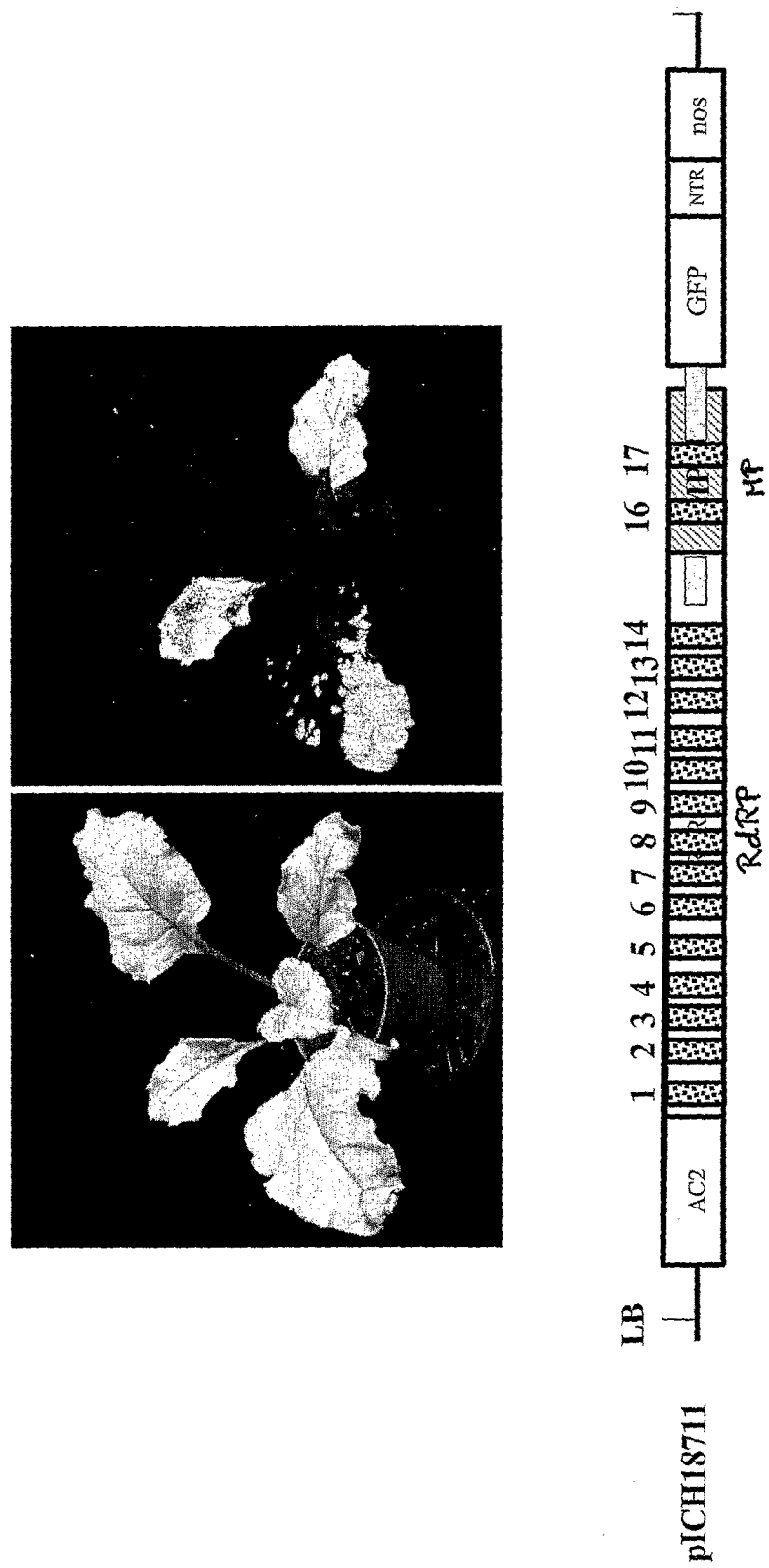
FIG. 14 shows leaves of *Beta vulgaris* one week after agro-infiltration with pICH18711 at day light (left) and UV (right) illumination. Light patches in the right photograph indicate GFP fluorescence. Introns (spotted boxes) in the construct shown at the bottom are numbered.

GFP expression was high in leaves of the plants infiltrated with pICH18711 (FIG. 14). In contrast, only a few small spots could be seen in control plants infiltrated with pICH16700 containing no intron (not shown).

ANNEX

```
SEQ ID No. 1 (NcoI-EcoRI fragment of pICH14833):
ccatggacaaagtgataaaggcagcttttgtggagacgatagcctgatttacattcctaaaggtttagacttgcctgatattcaggcggg
cgcgaacctcatgtggaacttcgaggccaaactcttcaggaagaagtatggttacttctgtggtcgttatgttattcaccatgatagagga
gccattgtgtattacgatccgcttaaactaatatctaagttaggttgtaaacatattagagatgttgttcacttagaagagttacgcgagtctt
tgtgtgatgtagctagtaacttaaataattgtgcgtatttttcacagttagatgaggccgttgccgaggttcataagaccgcggtaggcggt
tcgttttgcttttgtagtataattaagtatttgtcagataagagattgtttagagatttgttctttgtttgataatgtcgatagtctcgtacgaaccta
aggtgagtgatttcctcaatctttcgaagaaggaagagatcttgccgaaggctctaacgaggttagaattc SEQ ID No. 2 (part of pICH15466):
ggagataacctgagcttcttcttccataatgagagcactctcaattacacccacagcttcagcaacatcatcaagtacgtgtgcaagac
gttcttccctgctagtcaacgcttcgtgtaccacaaggagttcctggtcactagagtcaacacttggtactgcaagttcacgagagtggat
acgttcactctgttccgtggtgtgtaccacaacaatgtggattgcgaagagttttacaaggctatggacgatgcgtggcactacaaaaa
gacgttagcaatgcttaatgccgagaggaccatcttcaaggataacgctgcgttaaacttttggttcccgaaagtgagagacatggttat
cgtccctctctttgacgcttctatcacaactggtaggatgtctaggagagaggttatggtgaacaaggacttcgtctacacggtcctaaat
```

-continued

ANNEX cacatcaagacctatcaagctaaggcactgacgtacgcaaacgtgctgagcttcgtggagtctattaggtctagagtcataattaacgg
tgtcactgccaggtctgaatgggacacagacaaggcaattctaggtccattagcaatgacattcttcctgatcacgaagctgggtcatgt
gcaagat SEQ ID No. 3 (part of pICH15900):
gcggacgatacgtgatccaccatgatagaggagccattgtgtattacgatccgcttaaactaatatctaagctcggctgcaagcacatc
agagacgtcgtgcacttagaagagttacgcgagtctttgtgcgacgtagctagtaacttgaacaactgcgcctacttctcacagttagat
gaggccgttgctgaggtccacaagactgcggtcggaggctccttcgcgttctgtagcatcatcaaatacttgtcagacaagaggctgtt
cagggacctgttcttcgtctgagttgacg SEQ ID No. 4 (part of pICH15025): (contains 3 Introns shown underlined in italics)
Cccgagctatactgtaccttcgccgaccgattggtactacagtacaagaaggcggaggagttccaatcgtgtgatcttccaaacctct
agaagagtcagagaagtactacaacgcattatccgagctatcagtgcttgagaatctcgactcttttgacttagaggcgtttaagacttta
tgtcagcagaagaatgtggacccggatatggcagcaaag
*gtaaatcctggtccacacttttacgataaaaacacaagattttaaactatgaactgatcaataatcattcctaaaagaccacacttttgtttt*
*gtttctaaagtaatttttactgttataacag*
gtggtcgtagcaatcatgaagtcagaattgacgttgcctttcaagaaacctacagaagaggaaatctcggagtcgctaaaaccagga
gaggggtcgtgtgcagagcataaggaagtgttgagcttacaaaatgatgctccgttcccgtgtgtgaaaaatctagttgaaggttccgt
gccggcgtatggaatgtgtcctaagggtggtggtttcgacaaattggatgtggacattgctgatttccatctcaagagtgtagatgcagtt
aaaaagggaactatgatgtctgcggtgtacacagggtctatcaaagttcaacaaatgaagaactacatagattacttaagtgcgtcgct
ggcagctacagtctcaaacctctgcaag
*gtaagaggtcaaaaggtttccgcaatgatccctctttttttgttctctagtttcaagaatttgggtatatgactaacttctgagtgttccttgatg*
*catatttgtgatgagacaaatgtttgttctatgttttag*
gtgcttagagatgttcacggcgttgacccagagtcacaggagaaatctggagtgtgggatgttaggagaggacgttggttacttaaac
ctaatgcgaaaagtcacgcgtggggtgtggcagaagacgccaaccacaagttggttattgtgttactcaactgggatgacggaaagc
cggttgtgatgagacatggttcagggtggcggtgtcaagcgattccttgatatattcggatatgggaaaacttaagacgctcacgtcttg
cagtccaaatggtgagccaccggagcctaacgccaaagtaattttggtcgatggtgttcccggttgtggaaaaacgaaggagattatc
gaaaag
*gtaagttctgcatttggttatgctccttgcatttttaggtgttcgtcgctcttccatttccatgaatagctaagatttttttctctgcattcattctt*
*cttgcctcagttctaactgtttgtggtattttttgttttaattattgctacag* gtaaacttctctgaagacttgattttagtccctgggaaggaagctt SEQ ID No. 5 (part of pICH15034): (contains 3 Introns shown underlined in italics)
ctgcag
*gtaaaatattggatgccagacgatatctttcttttgatttgtaactttttcctgtcaaggtcgataaattttatttttttggtaaaaggtcgataatt*
*tttttttggagccattatgtaattttcctaattaactgaaccaaaattatacaaaccag*
gtttgctggaaaatttggttgcaatgatcaaaagaaacatgaatgcgccggatttgacagggacaattgacattgaggatactgcatct
ctggtggttgaaaagttttgggattcgtatgttgacaaggaatttagtggaacgaacgaaatgaccatgcaagggagagcttctccag
*gtaaggacttctcatgaatattagtggcagattagtgttgttaaagtctttggttagataatcgatgcctcctaattgtccatgttttactggtttt*
*ctacaattaaag*
gtggctttcgaaacaagagtcatctacagttggtcagttagcggactttaactttgtggatttgccggcagtagatgagtacaagcatatg
atcaagagtcaaccaaagcaaaagttagacttgagtattcaagacgaatatcctgcattgcagacgatagtctaccattcgaaaaag
atcaatgcgattttcggtccaatgttttcagaacttacgaggatgttactcgaaaggattgactcttcgaagtttctgttctacaccagaaag
acacctgcacaaatagaggacttctttttctgacctagactcaacccaggcgatgaaattctggaactcgacatttcgaagtacgataa
gtcacaaaacgagttccattgtgctgtagagtacaagatctgggaaaagttaggaattgatgagtggctagctgaggtctggaaacaa
g
*gtgagttcctaagttccattttttgtaatccttcaatgttattttaacttttcagatcaacatcaaaattaggttcaattttcatcaaccaaataat*
*attttttcatgtatatatag*
gtcacagaaaaacgaccttgaaagattatacggccggaatcaaaacatgtctttggtatcaaaggaaaagtggtgatgtgacaaccttt
tattggtaataccatcatcattgccgcatgtttgagctcaatgatccccatgg SEQ ID No. 6 (fragment of pICH15477, containing 1 Intron shown in underlined italics)
Gttttagttttattgcaacaacaacaacaaattacaataacaacaaacaaatacaaacaacaacaacatggcacaatttcaacaa
acaattgacatgcaaactctccaagccgctgcgggacgcaacagcttggtgaatgatttggcatctcgtcgcgtttacgataatgcagt
cgaggagctgaatgctcgttccagacgtcccaag
*gtaaaacaactttcattcacatatatgaatactttttgtcattgagtacgaagaagacacttactacttgttgatgaaagtttccgcctttata*
*cttatctatatcattttcatcatttcaaactagtatgaaattaggtgatgtttatatgatatcatggaacattaatctatagggaaactgttttgag*
*ttagttttgtataatattttttccctgtttttgatgttag*
gttcatttctccaaggcagtgtctacgggaacagacactgattgcaacaaacgcatatccggagttcgagatttcctttactcatacgcaat
ccgctgtgcactccttggccggaggccttcggtcacttgagttggagtatctcatgatgcaagttccgttcggctctctgacctacgacatc
ggcggaaacttctccgcgcacctcttcaaaggtaattttcttttctctactcaattttctccaagatccaatatttgaagactgatctatagttaa
aattaatctctactccattcttgttacctcaggtcgcgattacgttcactgctgcatgc:
gttttagttttattgcaacaacaacaacaaattacaataacaacaaacaaatacaaacaacaacaacatggcacaatttcaacaaa
caattgacatgcaaactctccaagccgctgcgggacgcaacagcttggtgaatgatttggcatctcgtcgcgtttacgataatgcagtc
gaggagctgaatgctcgttccagacgtcccaaggtaaaacaactttcattcacatatatgaatactttttgtcattgagtacgaagaaga
cacttactacttgttgatgaaagtttccgcctttatacttatctatatcattttcatcatttcaaactagtatgaaattaggtgatgtttatatgatat
catggaacattaatctatagggaaactgttttgagttagttttgtataatattttttccctgtttttgatgttaggttcatttttccaaggcagtgtctac
ggaacagacactgattgcaacaaacgcatatccggagttcgagatttcctttactcatacgcaatccgctgtgcactccttggccggag
gccttcggtcacttgagttggagtatctcatgatgcaagttccgttcggctctctgacctacgacatcggcggaaacttctccgcgcacct
cttcaaaggtaattttcttttctctactcaattttctccaagatccaatatttgaagactgatctatagttaaaattaatctctactccattcttgttac
ctcaggtcgcgattacgttcactgctgcatgc SEQ ID No. 7: T-DNA region of pICH12691, wherein sequence segments have the following
function:
Nucleotides 1 to 25: Left border (opposite strand),
Nucleotides 86 to 1484: Nos promoter-NPTII coding sequence-Nos terminator (on the opposite
strand),
Nucleotides 1506 to 1552: AttP recombination site (opposite strand), -continued

ANNEX

Nucleotides 1553 to 1599: intron 5' part (opposite strand),
Nucleotides 1600 to 2022: TVCV RdRP 5' end (opposite strand),
Nucleotides 2023 to 2809: *Arabidopsis* actin 2 promoter (opposite strand),
Nucleotides 2836 to 2903: AttB recombination site,
Nucleotides 2904 to 2959: intron 3' part,
Nucleotides 2960 to 7991: TVCV RdRP 3' part-MP 5' part,
Nucleotides 7992 to 8168: cr-TMV MP 3' end.
Nucleotides 8248 to 8967: GFP coding sequence
Nucleotides 8961 to 9215: cr-TMV 3' untranslated region,
Nucleotides 9234 to 9497: Nos terminator,
Nucleotides 9549 to 9473: T-DNA right border (opposite strand):

```
tggcaggatatattgtggtgtaaacaaattgacgcttagacaacttaataacacattgcggacgtttttaatgtactggggtggatgcagg
tcgatctagtaacatagatgacaccgcgcgcgataatttatcctagtttgcgcgctatattttgttttctatcgcgtattaaatgtataattgcg
ggactctaatcataaaaacccatctcataaataacgtcatgcattacatgttaattattacatgcttaacgtaattcaacagaaattatatg
ataatcatcgcaagaccggcaacaggattcaatcttaagaaactttattgccaaatgtttgaacgatctgcttgactctagatccagagtc
ccgctcagaagaactcgtcaagaaggcgatagaaggcgatgcgctgcgaatcgggagcggcgataccgtaaagcacgaggaa
gcggtcagcccattcgccgccaagctcttcagcaatatcacgggtagccaacgctatgtcctgatagcggtccgccacacccagccg
gccacagtcgatgaatccagaaaagcggccattttccaccatgatattcggcaagcaggcatcgccatgagtcacgacgagatcctc
gccgtcgggcatacgcgccttgagcctggcgaacagttcggctggcgcgagcccctgatgctcttcgtccagatcatcctgatcgaca
agaccggcttccatccgagtacgtgctcgctcgatgcgatgtttcgcttggtggtcgaatgggcaggtagccggatcaagcgtatgcag
ccgccgcattgcatcagccatgatggatactttctcggcaggagcaaggtgagatgacaggagatcctgccccggcacttcgcccaa
tagcagccagtcccttcccgcttcagtgacaacgtcgagcacagctgcgcaaggaacgcccgtcgtggccagccacgatagccgc
gctgcctcgtcctggagttcattcagggcaccggacaggtcggtcttgacaaaaagaaccgggcgcccctgcgctgacagccggaa
cacggcggcatcagagcagccgattgtctgttgtgcccagtcatagccgaatagcctctccacccaagcggccggagaacctgcgt
gcaatccatcttgttcaatcatgcgaaacgatccagatccggtgcagattatttggattgagagtgaatatgagactctaattggataccg
aggggaatttatggaacgtcagtggagcatttttgacaagaaatatttgctagctgatagtgaccttaggcgacttttgaacgcgcaata
atggtttctgacgtatgtgcttagctcattaaactccagaaacccgcggctgagtggctccttcaacgttgcggttctgtcagttccaaacg
taaaacggcttgtcccgcgtcatcggcggggtcataacgtgactcccttaattctccgctcatggtaccagcttctcgagcgaccctac
gcccccaactgagagaactcaaaggttaccccagttggggcacaacaaaaatcaaatctaaatttgtgtaattatgaaaatgaaactt
acctttgaagaggtgcgcggagaagtttccgccgatgtcgtaggtcagagagccgaacggaacttgcatcatgagatactccaactc
aagtgaccgaaggcctccggccaaggagtgcacagcggattgcgtatgagtaaaggaaatctcgaactccggatatgcgtttgttgc
aatcagtgtctgttccgtagacactgccttggagaaatgaaccttgggacgtctggaacgagcattcagctcctcgactgcattatcgta
aacgcgacgagatgccaaatcattcaccaagctgttgcgtcccgcagcggcttggagagtttgcatgtcaattgtttgttgaaattgtgcc
atgttgttgttgtttgtatttgtttgttgttattgtaatttgttgttgttgttgcaataaaactaaaacttcaaagcggagaggaaaatatatgaattt
atataggcgggtttatctcttacaactttattttcggcctttcaaaaaaataattaaaatcgacagacacgaatcatttcgaccacaggtaa
agataacgtgacctggctgtcagacagccttttccctcgtgttaactaatttttaaactaattaatcatctcagcccttggattagttcttttgctt
tgatggcttcatgactgtgacctgctcgatccgcgtgttacatgacagctccgtttttttagtggttaacttaaaccgagtcaatccaggcaa
cgttagtcgtcgtcgtggttggcttgttcaattagatttcatacaattcaacgtaatttaattcgttttctattagaattgtatcataattattcag
accgtgaaagaaagtgtctttcatgatgtgtttatggatatttatacaataagatacaatgtttcatcatattcactattcacgattagtatgta
cattaaataatggctactactacatccgaactcgtcaaaacgattctgaatcaattatacatatgctgactcttgcatacataaaaaatag
ttgtttaaattttgtctaactaatgtttggtataagtataatgttgagttgagataccaattacatcgagtctagccattttgtcgtgccatattcgt
caaaactttcttacataatgataacctagatctagatgagatatgtatcaatgtatttgagatcataattaagttcgttctaaattttgtcgaaa
cgcgtggtacgctgcagaattgctcgaagccgcggtgcgggtgccagggcgtgcccttgggctccccgggcgcgtactccacctcac
ccatcttttattacatgtttgaacttcaacaatttatgactttttgttcttattgttgcaggtcgcgattacgttcactgctgcatgcctaatctggat
gtacgtgacattgctcgccatgaaggacacaaggaagctatttacagttatgtgaatcgtttgaaaaggcagcagcgtcctgtgcctga
ataccagagggcagctttcaacaactacgctgagaacccgcacttcgtccattgcgacaaacctttccaacagtgtgaattgacgaca
gcgtatggcactgacacctacgctgtagctctccatagcatttatgatatccctgttgaggagttcggttctgcgctactcaggaagaatgt
gaaaacttgtttcgcggcctttcatttccatgagaatatgcttctagattgtgatacagtcacactcgatgagattggagctacttttcagaa
gtccggtgataatttaagtttttctttcataatgagagcactctcaattacacccacagttttagtaatataattaagtatgtgtgtaaaacgtt
ctttcctgctagtcaacggtttgtgtatcataaggagttttagttactagagtcaacacttggtactgtaagtttacgagagtggatacttttac
tcttttccgtggtgtgtaccataataatgtggattgcgaagagttttacaaggctatggacgatgcgtggcactacaaaaagacgttagca
atgcttaatgccgagaggaccatcttcaaggataacgctgcgttaaactttggttcccgaaagtgagagacatggttatcgtccctctctt
tgacgcttctatcacaactggtaggatgtctaggagagagattatggtgaacaaggatttcgtttatacggtcctaaatcacataaaaac
gtatcaagctaaggctttaacttacgcaaatgttctgtcctttgtggagtctattaggtctagagtgataattaacggtgtcactgccaggtct
gaatgggacacagacaaggcaattctaggtccattagcaatgacattttttccttataacaaagttgggtcatgtgcaggatgaaataatc
ctgaaaaagttccagaagttcgacagaaccaccaatgagctgatttggacaagtctctgcgatgccctgatggggttattccctcggt
caaggagacgcttgtgcgcggtggttttgtgaaagtagcagaacaagccttagagataaaggttcccgagctatactgtacctttgccg
acagattggtactacagtacaagaaggcggaggagttccaatcgtgtgatctttccaaacctctagaagagtcagagaagtactaca
acgcattatccgagctatcagtgcttgagaatctcgactcttttgacttagaggcgtttaagactttatgtcagcagaagaatgtggaccc
ggatatggcagcaaaggtggtcgtagcaatcatgaagtcagaattgacgttgcctttcaagaaacctacagaagaggaaatctcgga
gtcgctaaaaccaggagaggggtcgtgtgcagagcataaggaagtgttgagcttacaaaatgatgctccgttcccgtgtgtgaaaaat
ctagttgaaggttccgtgccggcgtatggaatgtgtcctaagggtggtgtttcgacaaattggatgtggacattgctgatttccatctcaa
gagtgtagatgcagttaaaaagggaactatgatgtctgcggtgtacacagggtctatcaaagttcaacaaatgaagaactacatagat
tacttaagtgcgtcgctggcagctacagtctcaaacctctgcaaggtgcttagagatgttcacggcgttgacccagagtcacaggaga
aatctggagtgtgggatgttaggagaggacgttggttacttaaacctaatgcgaaaagtcacgcgtggggtgtggcagaagacgcca
accacaagttggttattgtgttactcaactgggatgacggaaagccggtttgtgatgagacatggttcagggtggcggtgtcaagcgatt
ccttgatatattcggatatgggaaaacttaagacgctcacgtcttgcagtccaaatggtgagccaccggagcctaacgccaaagtaatt
ttggtcgatggtgttcccggttgtggaaaaacgaaggagattatcgaaaaggtaaacttctctgaagacttgattttagtccctgggaag
gaagcttctaagatgatcatccggagggccaaccaagctggtgtgataagagcggataagagcaatgttagaacggtggattccttct
tgatgcatccttctagaagggtgtttaagaggttgtttatcgatgaaggactaatgctgcatacaggttgtgtaaatttcctactgctgctatct
caatgtgacgtcgcatatgtgtatggggacacaaagcaaattccgttcatttgcagagtcgcgaactttccgtatccagcgcattttgcaa
aactcgtcgctgatgagaaggaggttagaagagttacgctcaggtgcccggctgatgttacgtatttccttaacaagaagtatgacggg
gcggtgatgtgtaccagcgcggtagagagatccgtgaaggcagaagtggtgagaggaaagggtgcattgaacccaataaccttac
cgttggagggtaaaattttgaccttcacacaagctgacaagttcgagttactggagaagggttacaaggatgtgaacactgtgcacga
ggtgcaaggggagacgtacgagaagactgctattgtgcgcttgacatcaactccgttagagatcatatcgagtgcgtcacctcatgtttt
ggtggcgctgacaagacacacaacgtgttgtaaatattacaccgttgtgttggacccgatggtgaatgtgatttcagaaatggagaagt
```

ANNEX

```
tgtccaatttccttcttgacatgtatagagttgagcgggggtccaatagcaattacagatcgatgcagtattcagggacagcaacttgttt
gttcagacgcccaagtcaggagattggcgagatatgcaattttactatgacgctcttcttcccggaaacagtactattctcaatgaatttga
tgctgttacgatgaatttgagggatatttccttaaacgtcaaagattgcagaatcgacttctccaaatccgtgcaacttcctaaagaacaa
cctattttcctcaagcctaaaataagaactgcggcagaaatgccgagaactgcaggtttgctggaaaatttggttgcaatgatcaaaag
aaacatgaatgcgccggatttgacagggacaattgacattgaggatactgcatctctggtggttgaaaagttttgggattcgtatgttgac
aaggaatttagtggaacgaacgaaatgaccatgacaagggaaagttttctagatggctttcgaaacaagagtcatctacagttggtc
agttagcggactttaactttgtggatttgccggcagtagatgagtacaagcatatgatcaagagtcaaccaaagcaaaagttagacttg
agtattcaagacgaatatcctgcattgcagacgatagtctaccattcgaaaaagatcaatgcgattttcggtccaatgttttcagaactta
cgaggatgttactgaaaggattgactcttcgaagtttctgttctacaccagaaagacacctgcacaaatagaggacttcttttctgacct
agactcaacccaggcgatgaaattctggaactcgacatttcgaagtacgataagtcacaaaacgagttccattgtgctgtagagtac
aagatctgggaaagttaggaattgatgagtggctagctgaggtatggaaacaaggacacagaaaaacgaccttgaaagattatac
ggccggagtcaaaacatgtctttggtatcaaagaaaagtggtgattgcaaccctttattggtaataccatcatcattgcagcctgtttg
agctcaatgatccccatggacaaagtgataaaggcagcttttgtggagacgatagcctgatttacattcctaaaggttttagacttgcctg
atattcaggcgggcgcgaacctcatgtggaacttcgaggccaaactcttcaggaagaagtatggttacttctgtggtcgttatgttattca
ccatgatagaggagccattgtgtattacgatccgcttaaactaatatctaagttaggttgtaaacatattagagatgttgttcacttagaag
agttacgcgagtcttttgtgatgtagctagtaacttaaataattgtgcgtattttcacagttagatgaggccgttgccgaggttcataaga
ccgcggtaggcggttcgtttgctttttgtagtataattaagtatttgtcagataagagattgtttagagatttgttctttgtttgataatgtcgatag
tctcgtacgaacctaaggtgagtgatttcctcaatctttcgaagaaggaagagatcttgccgaaggctctaacgaggttaaaaaccgtg
tctattagtactaaagatattatatctgtcaaggagtcggagactttgtgtgatatagatttgttaatcaatgtgccattagataagtatagat
atgtgggtatcctaggagcgtgtttttaccggagagtgactgtcgtagtcgttaaaggtggagtgacgataagtgtgatagataagc
gtctggtgaactcaaaggagtgcgtgattggtacgtacagagccgcagccaagatgtaagaggttccagttcaaattgttccaaatta
ctttgtgtccaccgtggacgcaaagaggaagccgtggcaggttcatgttcgtatacaagacttgaagattgaggcgggttggcagccg
ttagctctggaagtagtttcagttgctatggtcaccaataacgttgtcatgaagggtttgagggaaaaggtcgtcgcaataaatgatccg
gacgtcgaaggtttcgaaggtgtggttgacgaatcgtcgattcggttgcagcattttaaagtagatgaggccgttgacaactttaaaagaaggaaaaa
gaaggttgaagaaaagggtgtagtaagtaagtataagtacagacggagaagtacgccggtcctgattcgtttaatttgaaagaaga
aaacgtcttacaacattacaaacccgaataatcgataactcgagtatttttacaacaattaccaacaacaacaaacaacaaacaaca
ttacaattacatttacaattatcatggtgagcaagggcgaggagctgttcaccggggtggtgcccatcctggtcgagctggacggcgac
gtaaacggccacaagttcagcgtgtccggcgagggcgagggcgatgccacctacggcaagctgaccctgaagttcatctgcacca
ccggcaagctgcccgtgccctggcccaccctcgtgaccaccctcagctacggcgtgcagtgcttcagccgctaccccgaccacatga
agcagcacgacttcttcaagtccgccatgcccgaaggctacgtccaggagcgcaccatcttcttcaaggacgacggcaactacaag
acccgcgccgaggtgaagttcgagggcgacaccctggtgaaccgcatcgagctgaagggcatcgacttcaaggaggacggcaa
catcctggggcacaagctggagtacaactacaacagccacaacgtctatatcatgccgacaagcagaagaacggcatcaaggt
gaacttcaagatccgccacaacatcgaggacggcagcgtgcagctcgccgaccactaccagcagaacacccccatcggcgacg
gccccgtgctgctgcccgacaaccactacctgagcacccagtccgccctgagcaaagaccccaacgagaagcgcgatcacatgg
tcctgctggagttcgtgaccgccgccgggatcactcacggcatggacgagctgtacaagtaaagcggccccctagagcgtggtgcgc
acgatagcgcatagtgtttttctctccacttgaatcgaagagatagacttacggtgtaaatccgtaggggtggcgtaaaccaaattacgc
aatgttttgggttccatttaaatcgaaacccccttatttcctggatcacctgttaacgcacgtttgacgtgtattacagtgggaataagtaaaa
gtgagaggttcgaatcctcctaacccgggtagggccagcggccgctctagctagagtcaagcagatcgttcaaacatttggca
ataaagtttcttaagattgaatcctgttgccggtcttgcgatgattatcatataatttctgttgaattacgttaagcatgtaataattaacatgta
atgcatgacgttatttatgagatgggtttttatgattagagtcccgcaattatacatttaatacgcgatagaaaacaaaatatagcgcgca
aactaggataaattatcgcgcgcggtgtcatctatgttactagatcgaccagcttagatcagattgtcgtttcccgccttcagtttaaactat
cagtgtttgacaggatatattggcgggtaaac
```

The invention claimed is:

1. A process of expressing a sequence of interest in a plant, plant part, or plant cell culture, comprising:

transforming a plant, plant part, or plant cell culture with a suspension of Agrobacteria, said Agrobacteria containing in T-DNA a heterologous DNA having a sequence encoding a replicon operably linked or linkable to a transcription promoter, wherein said sequence encoding a replicon contains (i) sequences that have a replicon function of a plant RNA viral replicon, and (ii) a sequence of interest, wherein said suspension of Agrobacteria has a concentration of cells of said Agrobacteria corresponding to a calculated optical density at 600 nm of at most 0.004, wherein said calculated optical density is defined by an at least 250-fold dilution of a suspension of said Agrobacteria of an OD at 600 nm of 1.0.

2. The process of claim 1, wherein said suspension of Agrobacteria has a concentration of cells of said Agrobacteria corresponding to a calculated optical density at 600 nm of at most 0.001, wherein said calculated optical density is defined by an at least 1000-fold dilution of a suspension of said Agrobacteria of an OD at 600 nm of 1.0.

3. The process of claim 1, which is a process of transiently expressing said sequence of interest and comprises transient transformation of said plant, plant part, or plant cell culture with a nucleic acid molecule containing said heterologous DNA.

4. The process of claim 1, wherein said transforming is done by infiltrating said plant or said plant part with said suspension of Agrobacteria.

* * * * *

SEQUENCE LISTING

<160> NUMBER OF SEQ ID NOS: 8

<210> SEQ ID NO 1
<211> LENGTH: 538
<212> TYPE: DNA
<213> ORGANISM: Artificial Sequence
<220> FEATURE:
<223> OTHER INFORMATION: NcoI-EcoRI fragment of pICH14833

<400> SEQUENCE: 1

| | | |
|---|---|---|
| ccatggacaa agtgataaag gcagcttttt gtggagacga tagcctgatt tacattccta | 60 |
| aaggtttaga cttgcctgat attcaggcgg gcgcgaacct catgtggaac ttcgaggcca | 120 |
| aactcttcag gaagaagtat ggttacttct gtggtcgtta tgttattcac catgatagag | 180 |
| gagccattgt gtattacgat ccgcttaaac taatatctaa gttaggttgt aaacatatta | 240 |
| gagatgttgt tcacttagaa gagttacgcg agtctttgtg tgatgtagct agtaacttaa | 300 |
| ataattgtgc gtattttca cagttagatg aggccgttgc cgaggttcat aagaccgcgg | 360 |
| taggcggttc gtttgctttt tgtagtataa ttaagtattt gtcagataag agattgttta | 420 |
| gagatttgtt ctttgtttga taatgtcgat agtctcgtac gaacctaagg tgagtgattt | 480 |
| cctcaatctt tcgaagaagg aagagatctt gccgaaggct ctaacgaggt tagaattc | 538 |

<210> SEQ ID NO 2
<211> LENGTH: 636
<212> TYPE: DNA
<213> ORGANISM: Artificial Sequence
<220> FEATURE:
<223> OTHER INFORMATION: part of pICH15466

<400> SEQUENCE: 2

```
ggagataacc tgagcttctt cttccataat gagagcactc tcaattacac ccacagcttc    60
agcaacatca tcaagtacgt gtgcaagacg ttcttccctg ctagtcaacg cttcgtgtac   120
cacaaggagt tcctggtcac tagagtcaac acttggtact gcaagttcac gagagtggat   180
acgttcactc tgttccgtgg tgtgtaccac aacaatgtgg attgcgaaga gttttacaag   240
gctatggacg atgcgtggca ctacaaaaag acgttagcaa tgcttaatgc cgagaggacc   300
atcttcaagg ataacgctgc gttaaacttt tggttcccga agtgagagaa catggttatc   360
gtccctctct ttgacgcttc tatcacaact ggtaggatgt ctaggagaga ggttatggtg   420
aacaaggact tcgtctacac ggtcctaaat cacatcaaga cctatcaagc taaggcactg   480
acgtacgcaa acgtgctgag cttcgtggag tctattaggt ctagagtcat aattaacggt   540
gtcactgcca ggtctgaatg ggacacagac aaggcaattc taggtccatt agcaatgaca   600
ttcttcctga tcacgaagct gggtcatgtg caagat                             636
```

<210> SEQ ID NO 3
<211> LENGTH: 297
<212> TYPE: DNA
<213> ORGANISM: Artificial Sequence
<220> FEATURE:
<223> OTHER INFORMATION: part of pICH15900

<400> SEQUENCE: 3

```
gcggacgata cgtgatccac catgatagag gagccattgt gtattacgat ccgcttaaac    60
taatatctaa gctcggctgc aagcacatca gagacgtcgt gcacttagaa gagttacgcg   120
agtctttgtg cgacgtagct agtaacttga acaactgcgc ctacttctca cagttagatg   180
aggccgttgc tgaggtccac aagactgcgg tcggaggctc cttcgcgttc tgtagcatca   240
tcaaatactt gtcagacaag aggctgttca gggacctgtt cttcgtctga gttgacg      297
```

<210> SEQ ID NO 4
<211> LENGTH: 1419
<212> TYPE: DNA
<213> ORGANISM: Artificial Sequence
<220> FEATURE:
<223> OTHER INFORMATION: part of pICH15025

<400> SEQUENCE: 4

```
cccgagctat actgtacctt cgccgaccga ttggtactac agtacaagaa ggcggaggag    60
ttccaatcgt gtgatctttc caaacctcta gaagagtcag agaagtacta caacgcatta   120
tccgagctat cagtgcttga gaatctcgac tcttttgact tagaggcgtt taagacttta   180
tgtcagcaga agaatgtgga cccggatatg gcagcaaagg taaatcctgg tccacacttt   240
tacgataaaa acacaagatt ttaaactatg aactgatcaa taatcattcc taaaagacca   300
cacttttgtt ttgtttctaa agtaattttt actgttataa caggtggtcg tagcaatcat   360
gaagtcagaa ttgacgttgc cttttcaagaa acctacagaa gaggaaatct cggagtcgct   420
aaaaccagga gagggtcgt gtgcagagca taaggaagtg ttgagcttac aaaatgatgc    480
```

| | |
|---|---|
| tccgttcccg tgtgtgaaaa atctagttga aggttccgtg ccggcgtatg gaatgtgtcc | 540 |
| taagggtggt ggtttcgaca aattggatgt ggacattgct gatttccatc tcaagagtgt | 600 |
| agatgcagtt aaaaagggaa ctatgatgtc tgcggtgtac acagggtcta tcaaagttca | 660 |
| acaaatgaag aactacatag attacttaag tgcgtcgctg gcagctacag tctcaaacct | 720 |
| ctgcaaggta agaggtcaaa aggtttccgc aatgatccct cttttttgt ttctctagtt | 780 |
| tcaagaattt gggtatatga ctaacttctg agtgttcctt gatgcatatt tgtgatgaga | 840 |
| caaatgtttg ttctatgttt taggtgctta gagatgttca cggcgttgac ccagagtcac | 900 |
| aggagaaatc tggagtgtgg gatgttagga gaggacgttg gttacttaaa cctaatgcga | 960 |
| aaagtcacgc gtggggtgtg gcagaagacg ccaaccacaa gttggttatt gtgttactca | 1020 |
| actgggatga cggaaagccg gtttgtgatg agacatggtt cagggtggcg gtgtcaagcg | 1080 |
| attccttgat atattcggat atgggaaaac ttaagacgct cacgtcttgc agtccaaatg | 1140 |
| gtgagccacc ggagcctaac gccaaagtaa ttttggtcga tggtgttccc ggttgtggaa | 1200 |
| aaacgaagga gattatcgaa aaggtaagtt ctgcatttgg ttatgctcct tgcattttag | 1260 |
| gtgttcgtcg ctcttccatt tccatgaata gctaagattt tttttctctg cattcattct | 1320 |
| tcttgcctca gttctaactg tttgtggtat ttttgtttta attattgcta caggtaaact | 1380 |
| tctctgaaga cttgatttta gtccctggga aggaagctt | 1419 |

<210> SEQ ID NO 5
<211> LENGTH: 1159
<212> TYPE: DNA
<213> ORGANISM: Artificial Sequence
<220> FEATURE:
<223> OTHER INFORMATION: part of pICH15034

<400> SEQUENCE: 5

| | |
|---|---|
| ctgcaggtaa aatattggat gccagacgat attctttctt ttgatttgta acttttcct | 60 |
| gtcaaggtcg ataaattta ttttttttgg taaaaggtcg ataatttttt tttggagcca | 120 |
| ttatgtaatt ttcctaatta actgaaccaa aattatacaa accaggtttg ctggaaaatt | 180 |
| tggttgcaat gatcaaaaga aacatgaatg cgccggattt gacagggaca attgacattg | 240 |
| aggatactgc atctctggtg gttgaaaagt tttgggattc gtatgttgac aaggaattta | 300 |
| gtggaacgaa cgaaatgacc atgacaaggg agagcttctc caggtaagga cttctcatga | 360 |
| atattagtgg cagattagtg ttgttaaagt ctttggttag ataatcgatg cctcctaatt | 420 |
| gtccatgttt tactggtttt ctacaattaa aggtggcttt cgaaacaaga gtcatctaca | 480 |
| gttggtcagt tagcggactt taactttgtg gatttgccgg cagtagatga gtacaagcat | 540 |
| atgatcaaga gtcaaccaaa gcaaaagtta gacttgagta ttcaagacga atatcctgca | 600 |
| ttgcagacga tagtctacca ttcgaaaaag atcaatgcga ttttcggtcc aatgttttca | 660 |
| gaacttacga ggatgttact cgaaaggatt gactcttcga agtttctgtt ctacaccaga | 720 |
| aagacacctg cacaaataga ggacttcttt tctgacctag actcaaccca ggcgatggaa | 780 |
| attctggaac tcgacatttc gaagtacgat aagtcacaaa acgagttcca ttgtgctgta | 840 |
| gagtacaaga tctgggaaaa gttaggaatt gatgagtggc tagctgaggt ctggaaacaa | 900 |
| ggtgagttcc taagttccat tttttttgtaa tccttcaatg ttattttaac ttttcagatc | 960 |
| aacatcaaaa ttaggttcaa ttttcatcaa ccaaataata tttttcatgt atatataggt | 1020 |
| cacagaaaaa cgaccttgaa agattatacg gccggaatca aaacatgtct ttggtatcaa | 1080 |
| aggaaaagtg gtgatgtgac aacctttatt ggtaatacca tcatcattgc cgcatgtttg | 1140 |

```
agctcaatga tccccatgg                                                 1159
```

<210> SEQ ID NO 6
<211> LENGTH: 774
<212> TYPE: DNA
<213> ORGANISM: Artificial Sequence
<220> FEATURE:
<223> OTHER INFORMATION: fragment of pICH15477

<400> SEQUENCE: 6

```
gttttagttt tattgcaaca acaacaacaa attacaataa caacaaacaa aatacaaaca     60
acaacaacat ggcacaattt caacaaacaa ttgacatgca aactctccaa gccgctgcgg    120
gacgcaacag cttggtgaat gatttggcat ctcgtcgcgt ttacgataat gcagtcgagg    180
agctgaatgc tcgttccaga cgtcccaagg taaaacaaca tttcattcac atatatgaat    240
acttttgtca ttgagtacga agaagacact tactacttgt tgatgaaagt ttccgccttt    300
atacttatct atatcatttt catcatttca aactagtatg aaattaggtg atgtttatat    360
gatatcatgg aacattaatc tatagggaaa ctgttttgag ttagttttgt ataatatttt    420
tccctgtttg atgttaggtt catttctcca aggcagtgtc tacggaacag acactgattg    480
caacaaacgc atatccggag ttcgagattt cctttactca tacgcaatcc gctgtgcact    540
ccttggccgg aggccttcgg tcacttgagt tggagtatct catgatgcaa gttccgttcg    600
gctctctgac ctacgacatc ggcggaaact tctccgcgca cctcttcaaa ggtaattttc    660
tttctctact caattttctc caagatccaa tatttgaaga ctgatctata gttaaaatta    720
atctctactc cattcttgtt acctcaggtc gcgattacgt tcactgctgc atgc          774
```

<210> SEQ ID NO 7
<211> LENGTH: 16
<212> TYPE: DNA
<213> ORGANISM: Artificial Sequence
<220> FEATURE:
<223> OTHER INFORMATION: spacer in construct pICH8543

<400> SEQUENCE: 7

```
taatcgataa ctcgag                                                     16
```

<210> SEQ ID NO 8
<211> LENGTH: 9573
<212> TYPE: DNA
<213> ORGANISM: Artificial Sequence
<220> FEATURE:
<223> OTHER INFORMATION: T-DNA region of pICH12691

<400> SEQUENCE: 8

```
tggcaggata tattgtggtg taaacaaatt gacgcttaga caacttaata acacattgcg     60
gacgttttta atgtactggg gtggatgcag gtcgatctag taacatagat gacaccgcgc    120
gcgataattt atcctagttt gcgcgctata ttttgttttc tatcgcgtat taatgtata     180
attgcgggac tctaatcata aaaacccatc tcataaataa cgtcatgcat tacatgttaa    240
ttattacatg cttaacgtaa ttcaacagaa attatatgat aatcatcgca agaccggcaa    300
caggattcaa tcttaagaaa ctttattgcc aaatgtttga acgatctgct tgactctaga    360
tccagagtcc cgctcagaag aactcgtcaa gaaggcgata gaaggcgatg cgctgcgaat    420
cgggagcggc gataccgtaa agcacgagga agcggtcagc ccattcgccg ccaagctctt    480
cagcaatatc acgggtagcc aacgctatgt cctgatagcg gtccgccaca cccagccggc    540
```

-continued

```
cacagtcgat gaatccagaa aagcggccat tttccaccat gatattcggc aagcaggcat      600
cgccatgagt cacgacgaga tcctcgccgt cgggcatacg cgccttgagc ctggcgaaca      660
gttcggctgg cgcgagcccc tgatgctctt cgtccagatc atcctgatcg acaagaccgg      720
cttccatccg agtacgtgct cgctcgatgc gatgtttcgc ttggtggtcg aatgggcagg      780
tagccggatc aagcgtatgc agccgccgca ttgcatcagc catgatggat actttctcgg      840
caggagcaag gtgagatgac aggagatcct gccccggcac ttcgcccaat agcagccagt      900
cccttcccgc ttcagtgaca acgtcgagca cagctgcgca aggaacgccc gtcgtggcca      960
gccacgatag ccgcgctgcc tcgtcctgga gttcattcag gcaccggac aggtcggtct      1020 tgacaaaaag aaccgggcgc ccctgcgctg acagccggaa cacggcggca tcagagcagc     1080
cgattgtctg ttgtgcccag tcatagccga atagcctctc cacccaagcg gccgagaac     1140 ctgcgtgcaa tccatcttgt tcaatcatgc gaaacgatcc agatccggtg cagattattt    1200
ggattgagag tgaatatgag actctaattg gataccgagg ggaatttatg gaacgtcagt    1260
ggagcatttt tgacaagaaa tatttgctag ctgatagtga ccttaggcga cttttgaacg    1320
cgcaataatg gtttctgacg tatgtgctta gctcattaaa ctccagaaac ccgcggctga    1380
gtggctcctt caacgttgcg gttctgtcag ttccaaacgt aaaacggctt gtcccgcgtc    1440
atcggcgggg gtcataacgt gactcccttaa attctccgct catggtacca gcttctcgag    1500
cgaccctacg cccccaactg agagaactca aaggttaccc cagttgggc acaacaaaaa     1560 tcaaatctaa atttgtgtaa ttatgaaaat gaaacttacc tttgaagagg tgcgcggaga    1620
agtttccgcc gatgtcgtag gtcagagagc cgaacgaaac ttgcatcatg agatactcca    1680
actcaagtga ccgaaggcct ccggccaagg agtgcacagc ggattgcgta tgagtaaagg    1740
aaatctcgaa ctccggatat gcgtttgttg caatcagtgt ctgttccgta gacactgcct    1800
tggagaaatg aaccttggga cgtctggaac gagcattcag ctcctcgact gcattatcgt    1860
aaacgcgacg agatgccaaa tcattcacca agctgttgcg tcccgcagcg gcttggagag    1920
tttgcatgtc aattgtttgt tgaaattgtg ccatgttgtt gttgtttgta ttttgtttgt    1980
tgttattgta atttgttgtt gttgttgcaa taaaactaaa acttcaaagc ggagaggaaa    2040
atatatgaat ttatataggc gggtttatct cttacaactt tattttcggc cttttcaaaaa    2100 aataattaaa atcgacagac acgaatcatt tcgaccacag gtaaagataa cgtgacctgg    2160
ctgtcagaca gccttttccc tcgtgttaac taattttaa actaattaat catctcagcc    2220
cttggattag ttcttttgct ttgatggctt catgactgtg acctgctcga tccgcgtgtt    2280
acatgacagc tccgtttttt tagtggttaa cttaaaccga gtcaatccag caacgttag    2340 tcgtcgtcgt ggttggcttg ttcaattaga tttcatacaa ttcaacgtaa tttaattcgt    2400
tttctattag aattgtatca taattaattc agaccgtgaa agaaagtgtc tttcatgatg    2460 tgttatgga tatttataca ataagataca atgtttcatc atattcacta ttcacgatta    2520
gtatgtacat taaataatgg ctactactac atccgaactc gtcaaaacga ttctgaatca    2580
attatacata tgctgactct tgcatacata aaaaatagtt gtttaaattt tgtctaacta    2640
atgtttggta taagtataat gttgagttga gataccaatt acatcgagtc tagccatttt    2700
gtcgtgccat attcgtcaaa actttcttac ataatgataa cctagatcta gatgagatat    2760
gtatcaatgt atttgagatc ataattaagt tcgttctaaa ttttgtcgaa acgcgtggta    2820
cgctgcagaa ttgctcgaag ccgcggtgcg ggtgccaggg cgtgcccttg ggctccccgg    2880
gcgcgtactc cacctcaccc atctttttatt acatgtttga acttcaacaa tttatgactt    2940
```

```
tttgttctta ttgttgcagg tcgcgattac gttcactgct gcatgcctaa tctggatgta   3000
cgtgacattg ctcgccatga aggacacaag gaagctattt acagttatgt gaatcgtttg   3060
aaaaggcagc agcgtcctgt gcctgaatac cagagggcag ctttcaacaa ctacgctgag   3120
aacccgcact tcgtccattg cgacaaacct ttccaacagt gtgaattgac gacagcgtat   3180
ggcactgaca cctacgctgt agctctccat agcatttatg atatccctgt tgaggagttc   3240
ggttctgcgc tactcaggaa gaatgtgaaa acttgtttcg cggccttca tttccatgag    3300 aatatgcttc tagattgtga tacagtcaca ctcgatgaga ttggagctac ttttcagaag   3360
tccggtgata atttaagttt tttctttcat aatgagagca ctctcaatta cacccacagt   3420
tttagtaata taattaagta tgtgtgtaaa acgttcttc ctgctagtca acggtttgtg    3480
tatcataagg agttttagt tactagagtc aacacttggt actgtaagtt tacgagagtg    3540
gatactttta ctcttttccg tggtgtgtac cataataatg tggattgcga agagttttac   3600
aaggctatgg acgatgcgtg gcactacaaa agacgttag caatgcttaa tgccgagagg    3660
accatcttca aggataacgc tgcgttaaac ttttggttcc cgaaagtgag agacatggtt   3720
atcgtccctc tctttgacgc ttctatcaca actggtagga tgtctaggag agagattatg   3780
gtgaacaagg atttcgttta tacggtccta aatcacataa aaacgtatca agctaaggct   3840
ttaacttacg caaatgttct gtcctttgtg gagtctatta ggtctagagt gataattaac   3900
ggtgtcactg ccaggtctga atgggacaca gacaaggcaa ttctaggtcc attagcaatg   3960
acatttttcc ttataacaaa gttgggtcat gtgcaggatg aaataatcct gaaaaagttc   4020
cagaagttcg acagaaccac caatgagctg atttggacaa gtctctgcga tgccctgatg   4080 gggttattc cctcggtcaa ggagacgctt gtgcgcggtg gttttgtgaa agtagcagaa    4140
caagccttag agataaaggt tcccgagcta tactgtacct tgccgacag attggtacta    4200 cagtacaaga aggcggagga gttccaatcg tgtgatcttt ccaaacctct agaagagtca   4260
gagaagtact acaacgcatt atccgagcta tcagtgcttg agaatctcga ctcttttgac   4320
ttagaggcgt ttaagacttt atgtcagcag aagaatgtgg acccggatat ggcagcaaag   4380
gtggtcgtag caatcatgaa gtcagaattg acgttgcctt tcaagaaacc tacagaagag   4440
gaaatctcgg agtcgctaaa accaggagag gggtcgtgtg cagagcataa ggaagtgttg   4500
agcttacaaa atgatgctcc gttcccgtgt gtgaaaaatc tagttgaagg ttccgtgccg   4560
gcgtatggaa tgtgtcctaa gggtggtggt ttcgacaaat tggatgtgga cattgctgat   4620
ttccatctca agagtgtaga tgcagttaaa aagggaacta tgatgtctgc ggtgtacaca   4680
gggtctatca agttcaaca aatgaagaac tacatagatt acttaagtgc gtcgctggca    4740
gctacagtct caacctctg caaggtgctt agagatgttc acggcgttga cccagagtca    4800
caggagaaat ctggagtgtg ggatgttagg agaggacgtt ggttacttaa acctaatgcg   4860
aaaagtcacg cgtggggtgt ggcagaagac gccaaccaca agttggttat tgtgttactc   4920
aactgggatg acggaaagcc ggtttgtgat gagacatggt tcagggtggc ggtgtcaagc   4980
gattccttga tatattcgga tatgggaaaa cttaagacgc tcacgtcttg cagtccaaat   5040
ggtgagccac cggagcctaa cgccaaagta attttggtcg atggtgttcc cggttgtgga   5100
aaaacgaagg agattatcga aaaggtaaac ttctctgaag acttgatttt agtccctggg   5160
aaggaagctt ctaagatgat catccggagg gccaaccaag ctggtgtgat aagagcggat   5220
aaggacaatg ttagaacggt ggattccttc ttgatgcatc cttctagaag ggtgtttaag   5280
```

```
aggttgttta tcgatgaagg actaatgctg catacaggtt gtgtaaattt cctactgctg    5340
ctatctcaat gtgacgtcgc atatgtgtat ggggacacaa agcaaattcc gttcatttgc    5400
agagtcgcga actttccgta tccagcgcat tttgcaaaac tcgtcgctga tgagaaggag    5460
gttagaagag ttacgctcag gtgcccggct gatgttacgt atttccttaa caagaagtat    5520 gacgggcgg tgatgtgtac cagcgcggta gagagatccg tgaaggcaga agtggtgaga     5580
ggaaagggtg cattgaaccc aataaccta ccgttggagg gtaaaattt gaccttcaca      5640 caagctgaca agttcgagtt actggagaag ggttacaagg atgtgaacac tgtgcacgag    5700
gtgcaagggg agacgtacga gaagactgct attgtgcgct tgacatcaac tccgttagag    5760
atcatatcga gtgcgtcacc tcatgttttg gtggcgctga aagacacac aacgtgttgt     5820 aaatattaca ccgttgtgtt ggacccgatg gtgaatgtga tttcagaaat ggagaagttg    5880
tccaatttcc ttcttgacat gtatagagtt gaagcggggg tccaatagca attacagatc    5940
gatgcagtat tcagggacag caacttgttt gttcagacgc ccaagtcagg agattggcga    6000
gatatgcaat tttactatga cgctcttctt cccggaaaca gtactattct caatgaattt    6060
gatgctgtta cgatgaattt gagggatatt tccttaaacg tcaaagattg cagaatcgac    6120
ttctccaaat ccgtgcaact tcctaaagaa caacctattt tcctcaagcc taaaataaga    6180
actgcggcag aaatgccgag aactgcaggt ttgctggaaa atttggttgc aatgatcaaa    6240
agaaacatga atgcgccgga tttgacaggg acaattgaca ttgaggatac tgcatctctg    6300
gtggttgaaa agtttggga ttcgtatgtt gacaaggaat ttagtggaac gaacgaaatg     6360
accatgacaa ggggaaagttt ttctagatgg ctttcgaaac aagagtcatc tacagttggt   6420
cagttagcgg actttaactt tgtggatttg ccggcagtag atgagtacaa gcatatgatc    6480
aagagtcaac caaagcaaaa gttagacttg agtattcaag acgaatatcc tgcattgcag    6540
acgatagtct accattcgaa aaagatcaat gcgattttcg gtccaatgtt ttcagaactt    6600
acgaggatgt tactcgaaag gattgactct tcgaagtttc tgttctacac cagaaagaca    6660
cctgcacaaa tagaggactt cttttctgac ctagactcaa cccaggcgat ggaaattctg    6720
gaactcgaca tttcgaagta cgataagtca caaaacgagt tccattgtgc tgtagagtac    6780
aagatctggg aaaagttagg aattgatgag tggctagctg aggtatggaa acaaggacac    6840
agaaaaacga ccttgaaaga ttatacggcc ggagtcaaaa catgtctttg gtatcaaagg    6900
aaaagtggtg atgtgacaac ctttattggt aataccatca tcattgcagc ctgtttgagc    6960
tcaatgatcc ccatggacaa agtgataaag gcagctttt gtggagacga tagcctgatt     7020
tacattccta aaggtttaga cttgcctgat attcaggcgg gcgcgaaccct catgtggaac   7080 ttcgaggcca aactcttcag gaagaagtat ggttacttct gtggtcgtta tgttattcac    7140
catgatagag gagccattgt gtattacgat ccgcttaaac taatatctaa gttaggttgt    7200
aaacatatta gagatgttgt tcacttagaa gagttacgcg agtctttgtg tgatgtagct    7260
agtaacttaa ataattgtgc gtatttttca cagttagatg aggccgttgc cgaggttcat    7320
aagaccgcgg taggcggttc gtttgctttt tgtagtataa ttaagtattt gtcagataag    7380
agattgttta gagatttgtt cttttgtttga taatgtcgat agtctcgtac gaacctaagg   7440
tgagtgattt cctcaatctt tcgaagaagg aagagatctt gccgaaggct ctaacgaggt    7500
taaaaaccgt gtctattagt actaaagata ttatatctgt caaggagtcg gagactttgt    7560
gtgatataga tttgttaatc aatgtgccat tagataagta tagatatgtg ggtatcctag    7620
gagctgtttt taccggagag tggctagtgc cagacttcgt taaaggtgga gtgacgataa    7680
```

-continued

```
gtgtgataga taagcgtctg gtgaactcaa aggagtgcgt gattggtacg tacagagccg    7740
cagccaagag taagaggttc cagttcaaat tggttccaaa ttactttgtg tccaccgtgg    7800
acgcaaagag gaagccgtgg caggttcatg ttcgtataca agacttgaag attgaggcgg    7860
gttggcagcc gttagctctg gaagtagttt cagttgctat ggtcaccaat aacgttgtca    7920
tgaagggttt gagggaaaag gtcgtcgcaa taaatgatcc ggacgtcgaa ggtttcgaag    7980
gtgtggttga cgaattcgtc gattcggttg cagcatttaa agcggttgac aactttaaaa    8040
gaaggaaaaa gaaggttgaa gaaaagggtg tagtaagtaa gtataagtac agaccggaga    8100
agtacgccgg tcctgattcg tttaatttga aagaagaaaa cgtcttacaa cattacaaac    8160
ccgaataatc gataactcga gtatttttac aacaattacc aacaacaaca aacaacaaac    8220
aacattacaa ttacatttac aattatcatg gtgagcaagg gcgaggagct gttcaccggg    8280
gtggtgccca tcctggtcga gctggacggc gacgtaaacg gccacaagtt cagcgtgtcc    8340
ggcgagggcg agggcgatgc cacctacggc aagctgaccc tgaagttcat ctgcaccacc    8400
ggcaagctgc ccgtgccctg gcccaccctc gtgaccacct cagctacgg cgtgcagtgc    8460
ttcagccgct accccgacca catgaagcag cacgacttct tcaagtccgc catgcccgaa    8520
ggctacgtcc aggagcgcac catcttcttc aaggacgacg gcaactacaa gacccgcgcc    8580
gaggtgaagt tcgagggcga caccctggtg aaccgcatcg agctgaaggg catcgacttc    8640
aaggaggacg gcaacatcct ggggcacaag ctggagtaca actacaacag ccacaacgtc    8700
tatatcatgg ccgacaagca gaagaacggc atcaaggtga acttcaagat ccgccacaac    8760
atcgaggacg gcagcgtgca gctcgccgac cactaccagc agaacacccc catcggcgac    8820
ggccccgtgc tgctgcccga caaccactac ctgagcaccc agtccgccct gagcaaagac    8880
cccaacgaga gcgcgatca catggtcctg ctggagttcg tgaccgccgc cgggatcact    8940
cacggcatgg acgagctgta caagtaaagc ggcccctaga gcgtggtgcg cacgatagcg    9000
catagtgttt ttctctccac ttgaatcgaa gagatagact tacggtgtaa atccgtaggg    9060
gtggcgtaaa ccaaattacg caatgttttg ggttccattt aaatcgaaac cccttatttc    9120
ctggatcacc tgttaacgca cgtttgacgt gtattacagt gggaataagt aaaagtgaga    9180
ggttcgaatc ctccctaacc ccgggtaggg gcccagcggc cgctctagct agagtcaagc    9240
agatcgttca aacatttggc aataaagttt cttaagattg aatcctgttg ccggtcttgc    9300
gatgattatc atataattttc tgttgaatta cgttaagcat gtaataatta acatgtaatg    9360
catgacgtta tttatgagat gggttttat gattagagtc ccgcaattat acatttaata    9420
cgcgatagaa aacaaaatat agcgcgcaaa ctaggataaa ttatcgcgcg cggtgtcatc    9480
tatgttacta gatcgaccag cttagatcag attgtcgttt cccgccttca gtttaaacta    9540
tcagtgtttg acaggatata ttggcgggta aac                                 9573
```